United States Patent
Pfeifer et al.

(10) Patent No.: US 9,221,900 B2
(45) Date of Patent: Dec. 29, 2015

(54) METHODS FOR IDENTIFYING SAFE AND FUNCTIONAL HUMANIZED ANTIBODIES

(75) Inventors: Andrea Pfeifer, St-Legier (CH); Andreas Muhs, Pully (CH); Oskar Adolfsson, Bercher (CH); Ryan J. Watts, San Mateo, CA (US)

(73) Assignees: AC IMMUNE S.A. (CH); GENENTECH, INC., San Francisco, CA (US)

( * ) Notice: Subject to any disclaimer, the term of this patent is extended or adjusted under 35 U.S.C. 154(b) by 244 days.

(21) Appl. No.: 13/136,435

(22) Filed: Jul. 29, 2011

(65) Prior Publication Data

US 2012/0064065 A1  Mar. 15, 2012

Related U.S. Application Data

(60) Provisional application No. 61/400,650, filed on Jul. 30, 2010.

(51) Int. Cl.
*G01N 33/50* (2006.01)
*G01N 33/577* (2006.01)
*G01N 33/68* (2006.01)
*C07K 14/47* (2006.01)
*C07K 16/18* (2006.01)

(52) U.S. Cl.
CPC .............. *C07K 16/18* (2013.01); *C07K 14/4711* (2013.01); *G01N 33/5058* (2013.01); *C07K 2317/24* (2013.01); *G01N 33/5055* (2013.01); *G01N 2333/4709* (2013.01); *G01N 2500/10* (2013.01); *G01N 2800/2821* (2013.01)

(58) Field of Classification Search
CPC .......... G01N 2500/10; G01N 2500/00; G01N 2333/4709; G01N 33/5058
See application file for complete search history.

(56) References Cited

U.S. PATENT DOCUMENTS

| | | |
|---|---|---|
| 4,666,829 A | 5/1987 | Glenner et al. |
| 4,895,841 A | 1/1990 | Sugimoto et al. |
| 5,218,100 A | 6/1993 | Muller-Hill et al. |
| 5,225,539 A | 7/1993 | Winter |
| 5,231,000 A | 7/1993 | Majocha et al. |
| 5,231,170 A | 7/1993 | Averback |
| 5,234,814 A | 8/1993 | Card et al. |
| 5,262,332 A | 11/1993 | Selkoe |
| 5,441,870 A | 8/1995 | Seubert et al. |
| 5,538,845 A | 7/1996 | Knops et al. |
| 5,567,720 A | 10/1996 | Averback |
| 5,589,154 A | 12/1996 | Anderson |
| 5,593,846 A | 1/1997 | Schenk et al. |
| 5,602,179 A | 2/1997 | Makovec et al. |
| 5,605,811 A | 2/1997 | Seubert et al. |
| 5,624,821 A | 4/1997 | Winter et al. |
| 5,665,355 A | 9/1997 | Primi |
| 5,679,531 A | 10/1997 | Konig |
| 5,688,651 A | 11/1997 | Solomon |
| 5,693,753 A | 12/1997 | Konig |
| 5,705,401 A | 1/1998 | Masters et al. |
| 5,721,130 A | 2/1998 | Seubert et al. |
| 5,750,349 A | 5/1998 | Suzuki et al. |
| 5,766,846 A | 6/1998 | Schlossmacher et al. |
| 5,773,218 A | 6/1998 | Gallatin et al. |
| 5,786,180 A | 7/1998 | Konig |
| 5,837,822 A | 11/1998 | Gallatin et al. |
| 5,859,205 A | 1/1999 | Adair et al. |
| 5,955,285 A | 9/1999 | Averback |
| 5,955,317 A | 9/1999 | Suzuki et al. |
| 6,018,024 A | 1/2000 | Seubert et al. |
| 6,080,588 A | 6/2000 | Glick et al. |
| 6,114,133 A | 9/2000 | Seubert et al. |
| 6,180,370 B1 | 1/2001 | Queen et al. |
| 6,214,973 B1 | 4/2001 | Ohtomo et al. |
| 6,218,506 B1 | 4/2001 | Krafft et al. |
| 6,274,603 B1 | 8/2001 | Poirier |
| 6,284,221 B1 | 9/2001 | Schenk et al. |
| 6,287,793 B1 | 9/2001 | Schenk et al. |
| 6,294,171 B2 | 9/2001 | McMichael |
| 6,303,567 B1 | 10/2001 | Findeis et al. |
| 6,309,892 B1 | 10/2001 | Averback |
| 6,387,674 B1 | 5/2002 | Trasciatti et al. |
| 6,582,945 B1 | 6/2003 | Raso |
| 6,610,493 B1 | 8/2003 | Citron et al. |
| 6,664,442 B2 | 12/2003 | McConlogue et al. |
| 6,737,056 B1 | 5/2004 | Presta |
| 6,743,427 B1 | 6/2004 | Schenk |
| 6,750,324 B1 | 6/2004 | Schenk |

(Continued)

FOREIGN PATENT DOCUMENTS

| | | |
|---|---|---|
| CL | 2006-3485 | 12/2006 |
| CL | 2007-2070 | 7/2007 |
| CL | 2008-1741 | 6/2008 |
| CL | 2008-1742 | 6/2008 |
| CN | 1396183 | 2/2003 |
| DE | 3805744 | 2/1988 |
| EP | 0296560 | 6/1988 |
| EP | 0613007 | 8/1994 |
| EP | 0620276 A1 | 10/1994 |
| EP | 0623675 | 11/1994 |

(Continued)

OTHER PUBLICATIONS

Delgado, M et al. (2008) Vasoactive intestinal peptide protects against beta-amyloid-induced neurodegeneration by inhibiting microglia activation at multiple levels. Glia, 56:1091-1103.*

(Continued)

*Primary Examiner* — Kimberly A Ballard
(74) *Attorney, Agent, or Firm* — Jones Day

(57) ABSTRACT

The present invention is related to safe and functional antibodies for the therapeutic and diagnostic use in the treatment of an amyloidosis, a group of disorders and abnormalities associated with amyloid protein, such as Alzheimer's disease.

26 Claims, 16 Drawing Sheets

Figure 1D:
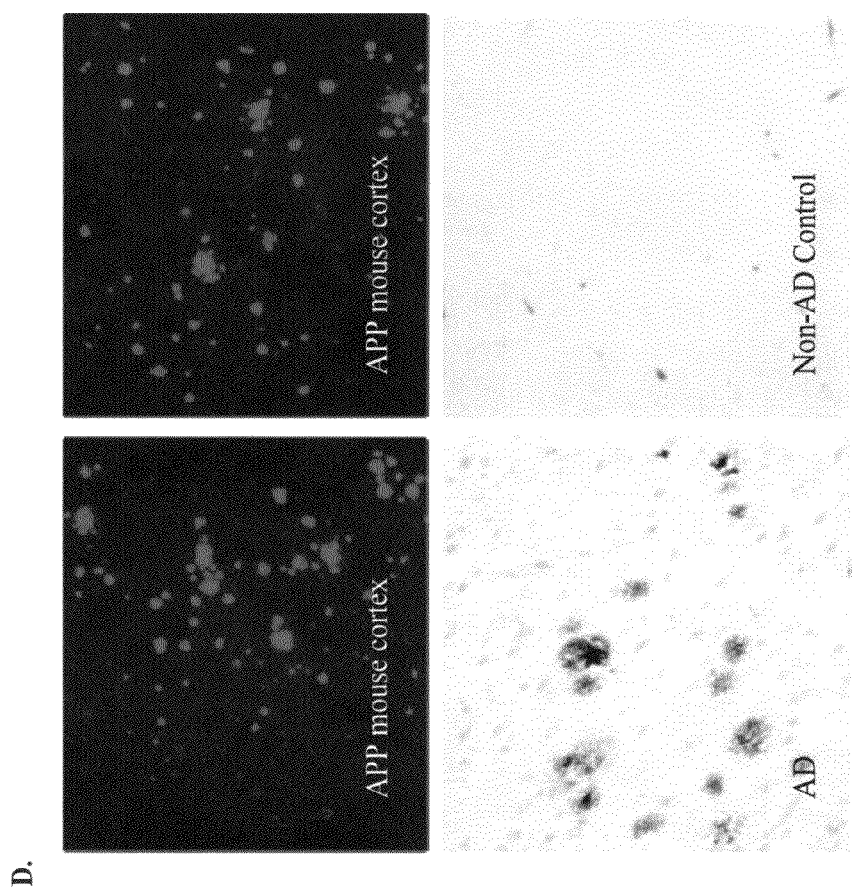

(9 of 16 Drawing Sheet(s) Filed in Color)

(56) References Cited

U.S. PATENT DOCUMENTS

| | | |
|---|---|---|
| 6,761,888 B1 | 7/2004 | Schenk |
| 6,787,138 B1 | 9/2004 | Schenk |
| 6,787,139 B1 | 9/2004 | Schenk |
| 6,787,140 B1 | 9/2004 | Schenk |
| 6,787,144 B1 | 9/2004 | Schenk |
| 6,787,523 B1 | 9/2004 | Schenk |
| 6,787,637 B1 | 9/2004 | Schenk |
| 6,815,175 B2 | 11/2004 | Weksler |
| 6,849,416 B2 | 2/2005 | Wiltfang et al. |
| 6,866,849 B2 | 3/2005 | Schenk |
| 6,866,850 B2 | 3/2005 | Schenk |
| 6,872,554 B2 | 3/2005 | Raso |
| 6,875,434 B1 | 4/2005 | Schenk |
| 6,905,686 B1 | 6/2005 | Schenk |
| 6,913,745 B1 | 7/2005 | Schenk |
| 6,936,698 B2 | 8/2005 | Taylor |
| 6,972,127 B2 | 12/2005 | Schenk |
| 6,998,124 B1 | 2/2006 | Erickson-Miller et al. |
| 7,014,855 B2 | 3/2006 | Schenk |
| 7,022,500 B1 | 4/2006 | Queen et al. |
| 7,060,270 B2 | 6/2006 | Nicolau et al. |
| 7,067,133 B2 | 6/2006 | Nicolau |
| 7,129,084 B2 | 10/2006 | Bulow et al. |
| 7,179,892 B2 | 2/2007 | Basi et al. |
| 7,189,819 B2 | 3/2007 | Basi et al. |
| 7,195,761 B2 | 3/2007 | Holtzman et al. |
| 7,256,273 B2 | 8/2007 | Basi et al. |
| 7,318,923 B2 | 1/2008 | Tsurushita et al. |
| 7,320,790 B2 | 1/2008 | Hinton et al. |
| 7,332,581 B2 | 2/2008 | Presta |
| 7,335,491 B2 | 2/2008 | Drapeau et al. |
| 7,339,035 B2 | 3/2008 | Yanagisawa et al. |
| 7,355,008 B2 | 4/2008 | Stavenhagen et al. |
| 7,371,365 B2 | 5/2008 | Poduslo et al. |
| 7,390,885 B2 | 6/2008 | Watkins et al. |
| 7,413,884 B2 | 8/2008 | Raso |
| 7,427,342 B2 | 9/2008 | Barber |
| 7,575,747 B2 | 8/2009 | Davies et al. |
| 7,625,560 B2 | 12/2009 | Basi et al. |
| 7,635,473 B2 | 12/2009 | Warne et al. |
| 7,732,568 B2 | 6/2010 | Mattner |
| 7,763,249 B2 | 7/2010 | Sugimura et al. |
| 7,763,250 B2 | 7/2010 | Rosenthal et al. |
| 7,771,722 B2 | 8/2010 | Holtzman et al. |
| 7,772,375 B2 | 8/2010 | Greferath et al. |
| 7,780,963 B2 | 8/2010 | Acton et al. |
| 7,794,719 B2 | 9/2010 | Bardroff et al. |
| 7,807,157 B2 | 10/2010 | Yamaguchi et al. |
| 7,820,799 B2 | 10/2010 | Godavarti et al. |
| 7,871,615 B2 | 1/2011 | Basi et al. |
| 7,892,544 B2 | 2/2011 | Pfeifer et al. |
| 7,902,328 B2 | 3/2011 | Hillen et al. |
| 7,906,626 B2 | 3/2011 | Raso |
| 7,927,594 B2 | 4/2011 | Rosenthal et al. |
| 7,932,048 B2 | 4/2011 | Mendez |
| 8,034,339 B2 | 10/2011 | Schenk |
| 8,048,420 B2 | 11/2011 | Pfeifer et al. |
| 8,106,164 B2 | 1/2012 | Gellerfors et al. |
| 8,124,353 B2 | 2/2012 | Pfeifer et al. |
| 8,246,954 B2 | 8/2012 | Pfeifer et al. |
| 8,329,886 B2 | 12/2012 | Bardroff et al. |
| 8,613,923 B2 | 12/2013 | Pfeifer et al. |
| 8,796,439 B2 | 8/2014 | Pfeifer et al. |
| 2001/0029293 A1 | 10/2001 | Gallatin et al. |
| 2002/0009445 A1 | 1/2002 | Du et al. |
| 2002/0062009 A1 | 5/2002 | Taylor |
| 2002/0086847 A1 | 7/2002 | Chain |
| 2002/0094335 A1 | 7/2002 | Chalifour et al. |
| 2002/0146750 A1 | 10/2002 | Hoogenboom et al. |
| 2002/0182660 A1 | 12/2002 | Fong |
| 2002/0197258 A1 | 12/2002 | Ghanbari et al. |
| 2003/0068316 A1 | 4/2003 | Klein et al. |
| 2003/0147882 A1 | 8/2003 | Solomon et al. |
| 2003/0190689 A1 | 10/2003 | Crosby et al. |
| 2003/0232758 A1 | 12/2003 | St. George-Hyslop et al. |
| 2004/0013647 A1 | 1/2004 | Solomon et al. |
| 2004/0043416 A1 | 3/2004 | Ji et al. |
| 2004/0043418 A1 | 3/2004 | Holtzman et al. |
| 2004/0058414 A1 | 3/2004 | Queen et al. |
| 2004/0087777 A1 | 5/2004 | Basi et al. |
| 2004/0142872 A1 | 7/2004 | Poduslo et al. |
| 2004/0146512 A1 | 7/2004 | Rosenthal et al. |
| 2004/0175394 A1 | 9/2004 | Schenk et al. |
| 2004/0181042 A1 | 9/2004 | Yanagisawa et al. |
| 2004/0191264 A1 | 9/2004 | Nielsen et al. |
| 2004/0192898 A1 | 9/2004 | Jia et al. |
| 2004/0213800 A1 | 10/2004 | Seubert et al. |
| 2004/0223912 A1 | 11/2004 | Montalto et al. |
| 2004/0241164 A1 | 12/2004 | Bales et al. |
| 2004/0242845 A1 | 12/2004 | Nicolau et al. |
| 2004/0260068 A1 | 12/2004 | Tsurushita et al. |
| 2004/0265919 A1 | 12/2004 | Vanderstichele et al. |
| 2005/0013815 A1 | 1/2005 | Schenk |
| 2005/0031651 A1 | 2/2005 | Gervais et al. |
| 2005/0037000 A1 | 2/2005 | Stavenhagen et al. |
| 2005/0097625 A1 | 5/2005 | Meade et al. |
| 2005/0124016 A1 | 6/2005 | LaDu et al. |
| 2005/0129691 A1 | 6/2005 | Gerlai |
| 2005/0129695 A1 | 6/2005 | Mercken et al. |
| 2005/0130947 A1 | 6/2005 | Biggadike et al. |
| 2005/0175626 A1 | 8/2005 | Delacourte et al. |
| 2006/0008458 A1 | 1/2006 | Solomon |
| 2006/0057646 A1 | 3/2006 | Wiltfang et al. |
| 2006/0073149 A1 | 4/2006 | Bales et al. |
| 2006/0115477 A1 | 6/2006 | Unger et al. |
| 2006/0127954 A1 | 6/2006 | Mercken et al. |
| 2006/0160161 A1 | 7/2006 | Pavliakova et al. |
| 2006/0198851 A1 | 9/2006 | Basi et al. |
| 2006/0246075 A1 | 11/2006 | Mercken et al. |
| 2006/0280733 A1 | 12/2006 | Kayed et al. |
| 2007/0010435 A1 | 1/2007 | Frangione et al. |
| 2007/0015218 A1 | 1/2007 | Cao et al. |
| 2007/0031416 A1 | 2/2007 | Shoji et al. |
| 2007/0110750 A1 | 5/2007 | Glabe et al. |
| 2007/0128191 A1 | 6/2007 | Barrio |
| 2007/0190046 A1 | 8/2007 | DeMattos et al. |
| 2007/0213512 A1 | 9/2007 | Krafft et al. |
| 2007/0218499 A1 | 9/2007 | Lambert et al. |
| 2008/0107601 A1 | 5/2008 | Lauwereys et al. |
| 2008/0121422 A1 | 5/2008 | Karasawa et al. |
| 2008/0199879 A1 | 8/2008 | Takayama et al. |
| 2008/0292639 A1 | 11/2008 | Shen et al. |
| 2009/0005257 A1 | 1/2009 | Jespers et al. |
| 2009/0017040 A1 | 1/2009 | Pfeifer et al. |
| 2009/0017041 A1 | 1/2009 | Pfeifer et al. |
| 2009/0022728 A1 | 1/2009 | Lin |
| 2009/0035295 A1 | 2/2009 | Hillen et al. |
| 2009/0035307 A1 | 2/2009 | Barghorn et al. |
| 2009/0074775 A1 | 3/2009 | Holtzman et al. |
| 2009/0093002 A1 | 4/2009 | Pfeifer et al. |
| 2009/0155249 A1 | 6/2009 | Pfeifer et al. |
| 2009/0155256 A1* | 6/2009 | Black et al. ............... 424/133.1 |
| 2009/0156471 A1 | 6/2009 | Gazit et al. |
| 2009/0162362 A1 | 6/2009 | Sarasa |
| 2009/0162878 A1 | 6/2009 | Kim et al. |
| 2009/0175847 A1 | 7/2009 | Barghorn et al. |
| 2009/0191190 A1 | 7/2009 | Barghorn et al. |
| 2009/0214515 A1 | 8/2009 | Holzman et al. |
| 2009/0232801 A1 | 9/2009 | Hillen et al. |
| 2009/0238831 A1 | 9/2009 | Hillen et al. |
| 2010/0080800 A1 | 4/2010 | Pfeifer et al. |
| 2010/0291097 A1 | 11/2010 | Pfeifer et al. |
| 2010/0297012 A1 | 11/2010 | Pfeifer et al. |
| 2010/0297013 A1 | 11/2010 | Pfeifer et al. |
| 2010/0297132 A1 | 11/2010 | Greferath et al. |
| 2011/0070613 A1 | 3/2011 | Greferath et al. |
| 2011/0142824 A1 | 6/2011 | Burbidge et al. |
| 2011/0212109 A1 | 9/2011 | Barghorn et al. |
| 2012/0064065 A1 | 3/2012 | Pfeifer et al. |
| 2012/0171216 A1 | 7/2012 | Pfeifer et al. |
| 2012/0244165 A1 | 9/2012 | Greferath et al. |
| 2012/0288896 A1 | 11/2012 | Greferath et al. |
| 2012/0329149 A1 | 12/2012 | Pfeifer et al. |

(56) References Cited

U.S. PATENT DOCUMENTS

| | | | |
|---|---|---|---|
| 2013/0164278 A1 | 6/2013 | Pfeifer et al. | |
| 2014/0199323 A1 | 7/2014 | Pfeifer et al. | |

FOREIGN PATENT DOCUMENTS

| | | |
|---|---|---|
| EP | 0304013 | 6/1996 |
| EP | 0783104 | 7/1997 |
| EP | 1130032 | 9/2001 |
| EP | 1420032 | 5/2004 |
| EP | 05027092.5 | 12/2005 |
| EP | 06014729.5 | 7/2006 |
| EP | 06014730.3 | 7/2006 |
| EP | 06020765.1 | 10/2006 |
| EP | 06020766.9 | 10/2006 |
| EP | 1741783 | 1/2007 |
| EP | 1861422 | 12/2007 |
| EP | 1954718 | 8/2008 |
| EP | 1963363 | 9/2008 |
| EP | 1976877 | 10/2008 |
| JP | 2007238096 | 9/1995 |
| JP | 2003509020 | 3/2003 |
| JP | 2003-523764 | 8/2003 |
| JP | 2004-500354 | 1/2004 |
| JP | 2005185281 | 7/2005 |
| JP | 2005-527199 | 9/2005 |
| JP | 2007077103 | 3/2007 |
| JP | 2009-519711 | 5/2009 |
| WO | WO 89/07657 | 8/1989 |
| WO | WO 90/12871 | 1/1990 |
| WO | WO 90/05746 | 5/1990 |
| WO | WO 90/07861 A2 | 7/1990 |
| WO | WO 91/18983 | 12/1991 |
| WO | WO 92/11018 | 7/1992 |
| WO | WO 94/17197 | 8/1994 |
| WO | WO 95/11994 | 5/1995 |
| WO | WO 96/01359 | 1/1996 |
| WO | WO 96/03631 | 2/1996 |
| WO | WO 96/28187 | 9/1996 |
| WO | WO 96/29605 | 9/1996 |
| WO | WO 96/36361 | 11/1996 |
| WO | WO 96/40731 | 12/1996 |
| WO | WO 97/10505 | 3/1997 |
| WO | WO 97/18476 | 5/1997 |
| WO | WO 97/21728 | 6/1997 |
| WO | WO 98/06403 | 2/1998 |
| WO | WO 99/05175 | 2/1999 |
| WO | WO 99/27944 | 6/1999 |
| WO | WO 99/40837 | 8/1999 |
| WO | WO 99/40909 | 8/1999 |
| WO | WO 99/59571 | 11/1999 |
| WO | WO 00/42072 A2 | 7/2000 |
| WO | WO 00/56771 | 9/2000 |
| WO | WO 00/72880 | 12/2000 |
| WO | WO 01/16364 | 3/2001 |
| WO | WO 01/18169 | 3/2001 |
| WO | WO 01/39796 | 6/2001 |
| WO | WO 01/62801 | 8/2001 |
| WO | WO 01/85093 | 11/2001 |
| WO | WO 02/46237 | 6/2002 |
| WO | WO 02/096937 | 12/2002 |
| WO | WO 03/014162 | 2/2003 |
| WO | WO 03/016466 | 2/2003 |
| WO | WO 03/031475 | 4/2003 |
| WO | WO 03/039467 A2 | 5/2003 |
| WO | WO 03/070760 | 8/2003 |
| WO | WO 03/076006 | 9/2003 |
| WO | WO 03/077858 | 9/2003 |
| WO | WO 03/090772 | 11/2003 |
| WO | WO 2004/024090 | 3/2004 |
| WO | WO 2004/029093 | 4/2004 |
| WO | WO 2004/029630 A1 | 4/2004 |
| WO | WO 2004/031400 | 4/2004 |
| WO | WO 2004/032868 A2 | 4/2004 |
| WO | WO 2004/050707 | 6/2004 |
| WO | WO 2004/058258 | 7/2004 |
| WO | WO 2004/065569 | 8/2004 |
| WO | WO 2004/067561 | 8/2004 |
| WO | WO 2004/071408 | 8/2004 |
| WO | WO 2004/108895 | 12/2004 |
| WO | WO 2005/005638 | 1/2005 |
| WO | WO 2005/011599 A2 | 2/2005 |
| WO | WO 2005/018424 | 3/2005 |
| WO | WO 2005/025516 | 3/2005 |
| WO | WO 2005/053604 | 6/2005 |
| WO | WO 2005/058941 | 6/2005 |
| WO | WO 2005/081872 | 9/2005 |
| WO | WO 2005/105998 | 11/2005 |
| WO | WO 2005/120571 | 12/2005 |
| WO | WO 2006/014478 A1 | 2/2006 |
| WO | WO 2006/016644 | 2/2006 |
| WO | WO 2006/029879 A2 | 3/2006 |
| WO | WO 2006/036291 | 4/2006 |
| WO | WO 2006/037604 | 4/2006 |
| WO | WO 2006/039327 | 4/2006 |
| WO | WO 2006/055178 | 5/2006 |
| WO | WO 2006/066049 | 6/2006 |
| WO | WO 2006/066089 | 6/2006 |
| WO | WO 2006/066171 | 6/2006 |
| WO | WO 2006/081171 | 8/2006 |
| WO | WO 2006/083533 | 8/2006 |
| WO | WO 2006/083689 | 8/2006 |
| WO | WO 2006/094724 | 9/2006 |
| WO | WO 2006/103116 | 10/2006 |
| WO | WO 2006/118959 | 11/2006 |
| WO | WO 2006/121656 | 11/2006 |
| WO | WO 2006/138737 A2 | 12/2006 |
| WO | WO 2007/011639 | 1/2007 |
| WO | WO 2007/017686 | 2/2007 |
| WO | WO 2007/022416 | 2/2007 |
| WO | WO 2007/042261 | 4/2007 |
| WO | WO 2007/050359 | 5/2007 |
| WO | WO 2007/062088 | 5/2007 |
| WO | WO 2007/062852 | 6/2007 |
| WO | WO 2007/064917 | 6/2007 |
| WO | WO 2007/064919 | 6/2007 |
| WO | WO 2007/064972 | 6/2007 |
| WO | WO 2007/068412 | 6/2007 |
| WO | WO 2007/068429 | 6/2007 |
| WO | WO 2007/070432 A2 | 6/2007 |
| WO | WO 2007/106617 | 9/2007 |
| WO | WO 2007/108756 | 9/2007 |
| WO | WO 2007/113172 | 10/2007 |
| WO | WO 2007/123345 | 11/2007 |
| WO | WO 2008/002893 | 1/2008 |
| WO | WO 2008/011348 | 1/2008 |
| WO | WO 2008/012101 | 1/2008 |
| WO | WO 2008/030251 | 3/2008 |
| WO | WO 2008/045962 | 4/2008 |
| WO | WO 2008/060364 | 5/2008 |
| WO | WO 2008/061795 | 5/2008 |
| WO | WO 2008/067464 | 6/2008 |
| WO | WO 2008/070229 | 6/2008 |
| WO | WO 2008/071394 | 6/2008 |
| WO | WO 2008/104385 | 9/2008 |
| WO | WO 2008/104386 | 9/2008 |
| WO | WO 2008/110885 | 9/2008 |
| WO | WO 2008/143708 | 11/2008 |
| WO | WO 2008/150946 | 12/2008 |
| WO | WO 2008/150949 | 12/2008 |
| WO | WO 2008/156621 | 12/2008 |
| WO | WO 2008/156622 | 12/2008 |
| WO | WO 2009/048537 | 4/2009 |
| WO | WO 2009/048538 | 4/2009 |
| WO | WO 2009/048539 | 4/2009 |
| WO | WO 2009/074583 A1 | 6/2009 |
| WO | WO 2012/016173 | 2/2012 |

OTHER PUBLICATIONS

Morgan D. (2009) The role of microglial in antibody-mediated clearance of amyloid-beta from the brain. CNS & Neurological Disorders—Drug Targets, 8:7-15.*
Vickers JC. Drugs Aging. 2002; 19(7):487-494.*

(56) References Cited

OTHER PUBLICATIONS

Koistinaho M & Koistinaho J. (2002) Role of p38 and p44/42 mitogen-activated protein kinases in microglia. Glia, 40:175-183.*
Sondag CM et al. (2009) Beta amyloid oligomers and fibrils stimulate differential activation of primary microglia. J. Neuroinflammation, 6:1 (13 pages).*
Lue LF & Walker DG (2002) Modeling Alzheimer's disease immune therapy mechanisms: Interactions of human postmortem microglia with antibody-opsonized amyloid beta peptide. J. Neurosci. Res. 70:599-610.*
Wilcock DM et al. (2004) Passive amyloid immunotherapy clears amyloid and transiently activates microglia in a transgenic mouse model of amyloid deposition. J. Neurosci. 24(27):6144-6151.*
Zhu Y et al. (2008) CD45RB is a novel molecular therapeutic target to inhibit A__peptide-induced microglial MAPK activation. PLoS ONE, 3(5):e2135.*
U.S. Appl. No. 13/461,658, filed May 1, 2012, Greferath et al.
U.S. Appl. No. 13/558,256, filed Jul. 25, 2012, Greferath et al.
Acha-Orbea et al., 1993, "Anti-T-cell receptor V beta antibodies in autoimmunity", Immunol Ser; 59:193-202.
Anderson et al., 2004, "Characterization of beta amyloid assemblies in drusen: the deposits associated with aging and age-related macular degeneration", Experimental Eye Research; 78:243-256.
Bard et al., 2000, "Peripherally administered antibodies against amyloid bipeptide enter the central nervous system and reduce pathology in a mouse model of Alzheimer disease", Nature Med.; 6:916-919.
Bard et al., 2003, "Epitope and isotype specificities of antibodies to beta-amyloid peptide for protection against Alzheimer's disease-like neuropathology", Proc Natl Acad Sci USA; 100(4): 2023-2028.
Barghorn et al., 2005, "Globular amyloid beta-peptide 1-42 oligomer—a homogeneous and stable neuropatholgical protein in Alzheimer's disease", J Neurochem; 95(31):834-847.
Barrow et al.,1992, "Solution conformations and aggregational properties of synthetic amyloid beta-peptides of Alzheimer's disease. Analysis of circular dichroism spectra", J. Mol. Biol.; 225:1075-1093.
Bateman et al., 2007, "Requirement of aggregation propensity of Alzheimer amyloid peptides for neuronal cell surface binding", BMC Neurosci; 8:29.
Bedzyk et al., 1990, "Active site structure and antigen binding properties of idiotypically cross-reactive anti-fluorescein monoclonal antibodies", J Biol Chem; 265(1):133-138.
Bitan et al., 2003, "Amyloid beta-protein (Abeta) assembly: Abeta 40 and Abeta 42 oligomerize through distinct pathways", Proc Natl Acad Sci USA; 100:330-335.
Blond et al., 1987, "Partly native epitopes are already present on early intermediates in the folding of trytophan synthase", Proc Natl Acad Sci USA; 84:1147-1151.
Brown et al., 1996, "Tolerance of single, but not multiple, amino acid replacements in antibody VH CDR 2: a means of minimizing B cell wastage from somatic hypermutation?", J Immunol; 156(9):3285-3291.
Burdick et al., 1992, "Assembly and aggregation properties of synthetic Alzheimer's A4/beta amyloid peptide analogs", J Biol Chem; 267:546-554.
Campbell et al., 1984, "General properties and applications of monoclonal antibodies", Elsevier Science Publishers B.V., pp. 1-32.
Casset et al., 2003, "A peptide mimetic of an anti-CD4 monoclonal antibody by rational design", Biochemical and Biophysical Research Communications; 307:198-205.
Celli et al., 1998, "Origin and pathogenesis of antiphospholipid antibodies", Braz J Med Biol Res; 31(6):723-732.
Chen et al., 1999, "Selection and analysis of an optimized anti-VEGF antibody: crystal structure of an affinity-matured Fab in complex with antigen", J Mol Biol; 293:865-881.
Clackson et al., 1991, "Making antibody fragments using phage display libraries", Nature; 352(15):624-328.

Cuenda et al., 2007, "p38 MAP-kinases pathway regulation, function and role in human diseases", Biochimica et Biophysica Acta; 1773:1358-1375.
Culbert et al., 2006, "MAPK-activated protein kinase 2 deficiency in microglia inhibits pro-inflammatory mediator release and resultant neurotoxicity", J Biol Chem; 281(33):23658-23667.
Database EMBL [Online], 1988, "Mouse innunoglobulin rearranged kappa-chain V-region V105 gene from C.AL20-TEPC-105 myeloma, exons 1 and 2", retrieved from EBI accession No. EMBL:M12183 Database accession No. M12183.
Database EMBL[Online], 1999, "Mus musculus F5.20G3 low-affinity anti-phosphorylcholine IgG antibody mRNA, partial cds", retrieved from EBI accession No. EMBL:AF044238 Database accession No. AF044238.
Database Geneseq [Online], 1988, "L chain subunit of FAS specific antibody coding sequence", retrieved from EBI accession No. GSN:AAT88870 Database accession No. AAT88870.
Database Geneseq [Online], 1999, "Anti-human FAS monoclonal antibody CH11 light chain cDNA", retrieved from EBI accession No. GSN:AAV66736 Database accession No. AAV66736.
Database Geneseq [Online], 2003, "Mouse DNA encoding antibody 3D8 heavy chain variable region", retrieved from EBI accession No. GSN:ABX16569 Database accession No. ABX16569.
Database Geneseq [Online], 2005, "Humanized monoclonal antibody Hu4785-2 heavy chain", retrieved from EBI accession No. GSP:ADX39139 Database accession No. ADX39139.
Database Geneseq [Online], 2005, "Humanized monoclonal antibody Hu4785-2 VH region", retrieved from EBI accession No. GSP:ADX39143 Database accession No. ADX39143.
Database Geneseq [Online], 2005, "Humanized monoclonal antibody Hu4785-2 partial protein", retrieved from EBI accession No. GSP:ADX39104 Database accession No. ADX39104.
Database Geneseq [Online], 2005, "Mouse monoclonal antibody 4785 heavy chain SEQ ID 38", retrieved from EBI accession No. GSP:ADX39137 Database accession No. ADX39137.
Database Geneseq [Online], 2005, "Mouse monoclonal antibody 4785 heavy chain SEQ ID 1", retrieved from EBI accession No. GSP:ADX39100 Database accession No. ADX39100.
Database NCBI Protein [Online] dated Apr. 11, 1996, accession No. AAA96779.
Database NCBI Protein [Online] dated Aug. 30, 1993, accession No. AAA38584.
Database NCBI Protein [Online] dated Mar. 23, 2002, accession No. AAL92941.
Database NCBI Protein [Online] dated Mar. 23, 2002, accession No. AAL92933.
David et al., 1991, "A significant reduction in the incidence of collagen induced arthritis in mice treated with anti-TCRV-beta antibodies", J Cell Biochem; p. 179.
Davies et al., 1995, "Antibody VH domains as small recognition units", Biotechnology; 13:475-479.
Davies et al., 1996, "Affinity improvement of single antibody VH domains: residues in all three hypervariable regions affect antigen binding", Inununotechnology; 2(3):169-179.
De Giorgi et al., 1993, "Induction of foetal lethality in AKR offspring after repeated inoculations into AKR females of anti-TCR/V beta 6 monoclonal antibody", Res Immunol; 144(4):245-255.
De Giorgi et al., 1993, "Murine hybridomas secreting monoclonal antibodies reacting with MIsa antigens", Exp Clin Immunogenet; 10(4):219-223.
De Pascalis et al., 2002, "Grafting of "Abbreviated" complementarity-determining regions contains specificity-determining residues essential for ligand contact to engineer a less immunogenic humanized monoclonal antibody", J Immunol; 169:3076-3084.
Dematttos et al., 2001, "Peripheral anti-Aβ antibody alters CNS and plasma Aβ clearance and decreases brain Aβ burden in a mouse model of Alzheimer's disease", Proc Natl Acad Sci USA; 98:8850-8855.
Dewachter et al., 2000, "Aging increased amyloid peptide and caused amyloid plaques in brain of old APP/V717I transgenic mice by a different mechanism than mutant presenilin 1", J Neurosci; 20:6452-6458.

(56) References Cited

OTHER PUBLICATIONS

Dewachter et al., 2002, "Neuronal deficiency of presenilin 1 inhibits amyloid plaque formation and corrects hippocampal long-term potentiation but not a cognitive defect of amyloid precursor protein [V717I] transgenic mice", J Neurosci; 22:3445-3453.
Ding et al., 2007, "Targeting age-related macular degeneration with Alzheimer's disease based immunotherapies: anti-amyloid-beta antibody attenuates pathologies in an age-related macular degeneration mouse model", Vision Research, Pergamon Press, Oxford, GB; 48(3)339-345.
Dorronsoro et al., 2003, "Peripheral and dual binding site inhibitors of acetylcholinesterase as neurodegenerative disease-modifying agents", Expert Opin Ther Pat; 13(11):1725-1732.
Doyle et al., 2004, "Toll-like receptors induce a phagocytic gene program through p38", J Exp Med; 199:81-90.
Dumoulin et al., 2002, "Single-domain antibody fragments with high conformational stability", Protein Sci; 11:500-515.
Ewert et al., 2003, "Biophysical properties of human antibody variable domains", J Mol Biol; 325:531-553.
Frenkel et al., 1999, "High affinity binding of monoclonal antibodies to the sequential epitope EFRH of beta-amyloid peptide is essential for modulation of fibrillar aggregation"; J Neuroimmunol; 95(1-2):136-142.
Frenkel et al., 2000, "Modulation of Alzheimer's beta-amyloid neurotoxicity by site-directed single-chain antibody", J Neuroimmunol; 106(1-2): 23-31.
Frenkel et al., 2001, "Generation of auto-antibodies towards Alzheimer's disease vaccination", Vaccine; 19(17-19):2615-2619.
Fujimuro et al, 1994, "Production and characterization of monoclonal antibodies specific to multi-ubiquitin chains of polyubiquitinated proteins", FEBS; 349:173-180.
Fujimuro et al, 2005, "Production of antipolyubiquitin monoclonal antibodies and their use for characterization and isolation of polyubiquitinated proteins", Meth Enzymol; 399:75-86.
Fukuchi et al., 2006, "Amelioration of amyloid load by anti-Abeta single-chain antibody in Alzheimer mouse model", Biochem Biophys Res Commun; 344(1):79-86.
GenBank accession No. BAE71460.1, Furkawa et al., data updated Jan. 6, 2006 (retrieved online Aug. 8, 2012).
GenBank accession No. CAA80022.1, Tillman et al, data updated Nov. 5, 1994 (retrieved online Aug. 8, 2012.
Gessner et al., 1998, "The IgG Fc receptor family", Aim Hematol; 76:231-248.
Glenner et al., 1984, "Alzheimer's disease: initial report of the purification and characterization of a novel cerebrovascular amyloid protein", Biochem Biophys Res Comm; 129:885-890.
Gouras et al., 2000, "Intraneuronal Abeta42 accumulation in human brain", Am J. Pathol; 156:15-20.
Guo et al., 2007, "Targeting amyloid-beta in glaucoma treatment", Proc Natl Acad Sci USA; 104(33):13444-13449.
Haass et al, 2007, "Soluble protein oligomers in neurodegeneration: lessons from the Alzheimer's amyloid beta-peptide", Nature Reviews; 8:101-112.
Hanan et al., 1996, "Inhibitory effect of monoclonal antibodies on Alzheime's β-amyloid peptide aggregation", Amyloid: Int J Exp Clin Invest; 3:130-133.
Heneka et al., 2005, "Focal glial activation coincides with increased with increased BACE1 activation and precedes amyloid plaque deposition in APP[V717I] transgenic mice", J Neuroinflammation; 2:22.
Hensley et al., 1999, "p38 kinase is activated in the Alzheimer's disease brain", J Neurochem; 72:2053-2058.
Hermanson ed, 1995, "Antibody modification and conjugation", Bioconjugate Techniques; Ch. 10:456-457.
Hicke, 2001, "Protein regulation by monoubiquitin", Nat Rev; 2:196-201.
Holm et al., 2007, "Functional mapping and single chain construction of the anti-cytokeratin 8 monoclonal antibody TS1", Mol Immunol; 44:1075-1084.
Holmes et al., 2008, "Long-term effects of Abeta42 immunisation in Alzheimer's disease: follow-up of a randomized, placebo-controlled phase I trial", Lancet; 372:216-223.
Holt et al., 2003, "Domain antibodies: proteins for therapy", Trends in Biotechnology; 21(11):484-490.
Hu et al., 2003, "Monoclonal antibody induced liver injury in transgenic mice harbouring HBV genes", Academic Journal of Second Military Medical University; 24(2):164-167.
International Search Report, dated Apr. 3, 2012 of International application No. PCT/US11/45948.
Johnson-Wood et al.,1997, "Amyloid precursor protein processing and a beta42 deposition in a transgenic mouse model of Alzheimer disease", Proc. Natl. Acad. Sci. USA; 94(4):1550-1555.
Jung et al., 1996, "Alzheimer's beta-amyloid precursor protein is expressed on the surface of immediately ex vivo brain cells: a flow cytometric study", J. Neurosci. Res.; 46(3):336-348.
Kabat et al.., 1991, "Sequences of proteins of immunological interest", U.S. Department of Health and Human Services, National Institutes of Health, NIH Publication No. 91-3242, pp. xv-xvi.
Khaw et al., 1982, "Teclmetium-99m labeling of antibodies to cardiac myosin Fab and to human fibrinogen", J Nucl Med; 23:1011-1019.
Kim et al., 2004, "Development of conformation-specific antibodies for neutralization of beta-amyloid oligomers", Neurobiol Aging; 25(1):S145, P1-175 Abstract.
Kirschner et al., 1986, "X-ray diffraction from intraneuronal paired helical filaments and extraneuronal amyloid fibers in Alzheimer disease indices cross-beta conformation", Proc Natl Acad Sci USA; 83:503-507.
Kisilevsky et al., 1995, "Arresting amyloidosis in vivo using small-molecule anionic sulphonates or sulphates: Implications for Alzheimer's disease", Nat Med; 1(2):143-148.
Kisilevsky, 1996, "Anti-amyloid drugs potential in the treatment of diseases associated with aging", Drugs Aging; 8(2):75-83.
Klein et al., 2002, "Abeta toxicity in Alzheimer's disease: globular oligomers (ADDLs) as new vaccine and drug targets", Neurochem Int; 41(5):345-352.
Klimka et at, 2000, "Human anti-CD30 recombinant antibodies by guided phage antibody selection using cell panning", Brit J Cancer; 83(2):252-260.
Koenigsknecht-Talboo et al., 2008, "Rapid microglial response around amyloid pathology after systemic anti-Aβ antibody administration in PDAPP mice", Neurobiology of Disease; 28(52):14156-14164.
Lambert et al., 2007, "Monoclonal antibodies that target pathological assemblies of Abeta", J Neurochem; 100(1): 23-35.
Langdon et al., 2000, "Germline sequences of $V_H$7183 gene family members in C57BL/6 mice demonstrate natural selection of particular sequences during recent evolution", Immunogen; 51:241-245.
Lee et al, 2002, "Molecular cloning of agonistic and antagonistic monoclonal antibodies against human 4-1BB", Eur J Immunogenet; 29(5):449-452.
Lee et al, 2006, "Targeting amyloid-beta peptide (Abeta) oligomers by passive immunization with a conformation-selective monoclonal antibody improves learning and memory in Abeta precursor protein (APP) transgenic mice", J Biol Chem; 281:4292-4299.
Levine, 1993, "Thioflavine T interaction with synthetic Alzheimer's disease beta-amyloid peptides: detection of amyloid aggregation in solution", Protein Sci; 2:404-410.
Levine et al., 2002, "4,4'-dianilino-1,1'-binaphthyl-5-disulfonate (bis-ANS) reports on non-β-sheet conformers of Alzheimer's peptide β (1-40)", Arch Biochem Biophys; 404:106-115.
Li et al., 2003, "Interleukin-1 mediates pathological effects of microglia on tau phosphorylation and on synaptophysin synthesis in cortical neurons through a p38-MAPK pathway", J Neuroscience; 23(5):1605-1611.
Liu Ruitian et al., 2004, "Single chain variable fragments against beta-amyloid (Abeta) can inhibit Abeta aggregation and prevent Abeta-induced neurotoxicity", Biochem; 43(22):6959-6967.
Lund et al., 1995, "Oligosaccaride-protein interactions in IgG can modulate recognition by Fc-gamma receptors", FASEB J; 9(1):115-119.

(56) References Cited

OTHER PUBLICATIONS

MacCallum et al., 1996, "Antibody-antigen interactions: contact analysis and binding site topography", J Mol Biol; 262:732-745.
Mamikonyan et al., 2007, "Amelioration of amyloid load by anti-Aβ-11 antibody binds to different β-amyloid species, inhibits fibril formation, and disaggregates preformed fibrils but not the most toxic oligomers", J Biol Chem; 282(31):22376-22386.
Marks et al., 1992, "By-passing immunization—Building high affinity human antibodies by chain shuffling", Biotechnology; 10:779-783.
Matrone et al., 2008, "NGF and BDNF signaling control amyloidogenic route and Aβ produciton in hippocampal neurons", Proc Natl Acad Sci USA; 105(35):13139-13144.
Maynard et al., 2000, "Antibody engineering", Annu Rev Biomed Eng; 2:339-376.
McGreer et al., 1994, "Pathological proteins in senile plaques", Tohoku J Exp Med; 174:269-277.
McKinnon et al, 2002, "Caspase activation and amyloid precursor protein cleavage in rat ocular hypertension", Invest Ophthamol & Vis Sci; 43(4):1077-1087.
McLaurin et al., 2002, "Therapeutically effective antibodies against amyloid-beta peptide target amyloid-beta residues 4-10 and inhibit cytotoxicity and fibrillogenesis", Nat Med; 8(11):1263-1269.
Mitchell et al., 2007, "Prevention of intracerebral haemorrhage", Current Drug Targets; 8:832-838.
Moechars et al., 1999, "Early phenotypic changes in transgenic mice that overexpress differenct mutants of amyloid precursor protein in brain", J Biol Chem; 274:6483-6492.
Mohajeri et al., 2004, "Assessment of the bioactivity of antibodies against β-amyloid peptide in vitro and in vivo", Neurodegenerative Disease; 1:160-167.
Moretto et al., 2007, "Conformation-sensitive antibodies against Alzheimer amyloid-beta by immunization with a thioredoxin-constrained B-cell epitope peptide", J Biol Chem; 282(15):11436-11445.
Moils et al., 2007, "Liposomal vaccines with conformation-specific amyloid peptide antigens define immune response and efficacy in APP transgenic mice", Proc Natl Acad Sci USA; 104(23):9810-9815.
Munoz et al.., 2007, "A novel p38α MAPK inhibitor suppresses brain proinflammatory cytokine up-regulation and attenuates synaptic dysfunction and behavioral deficits in an Alzheimer's disease mouse model", J Neuroinflammation; 4(21):1-14.
Munoz et al., 2010, "Targeting p38 MAPK pathway for the treatment of Alzheimer's disease", Neuropharmacology; 5(3):561-568.
Nelson et al., 2006, "Recent atomic models of amyloid fibril structure", Curr Opin Struct Biol; 16:260-265.
Nemes et al., 2004, "Cross-linking of ubiquitin, HSP27, parkin, and α-synuclein by γ-glutamyl-ε-lysine bonds in Alzheimer's neurofibrillary tangles", FASEB J; 18:1135-37.
Nicolau et al., 2002, "A liposome-based therapeutic vaccine against beta-amyloid plaques on the pancreas of transgenic norba mice", Proc Natl Acad Sci USA; 99(4): 2332-2337.
Nemmerjahn et al., 2006, "Fc gamma receptors: old friends and new family members", Immunity; 24:19-28.
Ohno et al., 1985, "Antigen binding specificities of antibodies are primarily determined by seven residues of VH", Proc Natl Acad Sci USA; 82(9):abstract.
Origlia et al., 2008, "Receptor for advanced glycation end product-dependent activation of p38 mitogen-activated protein kinase contributes to amyloid-β-mediated cortical synaptic dysfuntion", J Neurosci; 28(13):3521-3530.
Ozawa et al., 2002, "Enhanced $Aβ_{40}$ deposition was associated with increased $Aβ_{42/43}$ in cerebral vasculature with dutch-type hereditary cerebral hemorrhage with amyloidosis (HCHWA-D)", Ann NY Acad Sci; 977:149-154.
Padlan et al., 1989, "Structure of an antibody-antigen complex: crystal structure of the HyHEL-10 Fab-lysozyme complex", Proc Natl Acad Sci USA; 86(15):5938-42.
Pakula et al., 1989, "Genetic analysis of protein stability and function", Annu Rev Genet; 23:summary.

Paul eds., 1993, "Fv structure and diversity in three dimensions", Fundamental Immunology; 292-295.
Pereira et al., 1998, "Cardiolipin binding a light chain from lupus-prone mice", Biochemistry; 37(5):1430-1437.
Petkova et al., 2002, "A structural model for Alzheimer's β-amyloid fibrils based on experimental constraints from solid state NMR", Proc Natl Acad Sci USA; 99:16742-16747.
Petkova et al., 2004, "Solid state NMR reveals a pH-dependent antiparallel β-sheet registry in fibrils formed by a β-amyloid peptide", J Mol Biol; 335:247-260.
Pini et al, 1998, "Design and use of a phage display library. Human antibodies with subnanomolar affinity against a marker of angiogenesis eluted from a two-dimensional gel", J Biol Chem; 273(34):21769-21776.
Poduslo et al., 2010, "HH domain of Alzheimer's disease Aβ provides structural basis for neuronal binding in PC12 and mouse cortical/hippocampal neurons", PLoS One; 5:e8813.
Poling et al, 2008, "Oligomers of the amyloid-beta protein disrupt working memory: confirmation with two behavioral procedures", Behav Brain Res; 193(2):230-234.
Portolano et al., 1993, Lack of promiscuity in autoantigen-specific H and L chain combination as revealed by human H and L chain "roulette", J Immunol; 150(3):880-887.
Racke et al., 2005, "Exacerbation of cerebral amyloid angiopathy-associated microhemorrhage in amyloid precursor protein transgenic mice by immunotherapy is dependent on antibody recognition of deposited forms of amyloid beta", J. Neurosci.; 25(3):629-636.
Rader et al., 1998, "A phage display approach for rapid antibody humanization:designed combinatorial V gene libraries", Proc Natl Acad Sci USA; 95:8910-8915.
Ransohoff et al., 2009, "Microglial physiology: unique stimuli, specialized responses", Annu Rev Immunol, 27:119-145.
Rebe et al., 2005, "Deglycosylation of anti-β amyloid antibodies inhibits microglia activation in BV-2 cellular model", American Journal of Alzheimer's Disease and Other Dimentias; 20(5):303-313.
Roitt et al., 2000, "Humanized antibodies to amyloid beta", Immunology (translation from English, Moscow, Mir, 2000, p. 110).
Rudikoff et al, 1982, "Single amino acid substitution altering antigen-binding specificity", Proc Natl Acad Sci USA; 79(6):1979-1983.
Rzepecki et al., 2004, "Prevention of Alzheimer's disease-associated Aβ aggregation by rationally designed non-peptide β-sheet ligands", J Biol Chem; 279(46):47497-47505.
Schable et al., 1999, "Characteristics of the immunoglobulin V kappa genes, pseudogenes, relics and orphons in the mouse genome", Eur J Immunol; 29:2082-2086.
Schenk et al., 1999, "Immunization with amyloid-beta attenuates Alzheimer-disease-like pathology in the PDAPP mouse", Nature; 400:173-177.
Sergeant, 2003, "Truncated beta-amyloid peptide species in preclinical Alzheimer's disease as new targets for the vaccination approach", J Neurochem; 85(6):1581-91.
Seubert et al., 1992, "Isolation and quantification of soluble Alzheimer's beta-peptide from biological fluids", Nature 359(6393):325-327.
Smith et al., 1995, "Determination of helix-helix interactions in membranes by rotational resonance NMR", Proc Natl Acad Sci USA; 92:488-491.
Solomon et al., 1996, "Monoclonal antibodies inhibit in vitro fibrillar aggregation of the Alzheimer beta-amyloid peptide", Proc Natl Acad Sci USA;93:452-455.
Solomon et al., 1997, "Disaggregation of Alzheimer β-amyloid by site-directed mAb", Proc Natl Acad Sci USA; 94:4109-4112.
Solomon, 2007, "Beta-amyloid based immunotherapy as a treatment of Alzheimer's disease", Drugs of Today; 43(5):333-342.
Soto et al., 1995, "The alpha-helical to beta-strand transition in the amino-terminal fragment of the amyloid beta-peptide modulates amyloid formation", J. Biol. Chem.; 270(7)1063-3067.
Tenno et al., 1994, "Structural basis for distinct roles of Lys63- and Lys48-linked polyubiquitin chains", Genes to Cells; 9:865-875.
Vajdos et al., 2002, "Comprehensive functional maps of the antigen-binding site of an anti-ErbB2 antibody obtained with shotgun scanning mutagenesis", J Mol Biol; 320(2):415-428.

(56) References Cited

OTHER PUBLICATIONS

Van Den Beucken et al., 2001, "Building novel binding ligands to B7.1 and B7.2 based on human antibody single variable light chain domains", J Mol Biol; 310:591-601.

Van Der Auwera et al., 2005, "A ketogenic diet reduces amyloid beta 40 and 42 in a mouse model of Alzheimer's disease", Nutr Metab (Lond); 2:28.

Van Gool et al., 1994, "Concentrations of amyloid-beta protein in cerebrospinal fluid increase with age in patients free from neurodegenerative disease", Neurosci Let; 172(1-2):122-124.

Varisco et al., 2010, "MABT5102A is an effector-reduced anti-AB antibody with unique binding properties that promotes neuroprotection and glial engulfment of AB", Abstract presented at the 3rd Conference Clinical Trials on Alzheimer's Disease, Nov. 3-5, 2010, Toulouse, France. The Journal of Nutrition, Health, & Aging; 14(Suppl. 2):S5.

Vickers, 2002, "A vaccine against Alzheimer's disease", Drugs Aging; 19(7):487-494.

Ward et al., 1989, "Binding activities of a repertoire of single immunoglobulin variable domains secreted from *Escherichia coli*", Letters to Nature; 341(12):544-546.

Weaver-Feldhaus et al., 2004, "Yeast mating for combinatorial Fab library generation and surface display", FEBS Letters; 564(2):24-34.

Wikipedia, The Free Encyclopedia, 2012, "Glaucoma," [on-line], Jan. 30, 2012 [retrieved on Jan. 30, 2012], pp. 1-18, Retrieved from the Internet:< en.wikipedia.org/wiki/Glaucoma>.

Wirths et al., 2001, "Intraneuronal Abeta accumulation precedes plaque formation in beta-amyloid precursor protein and presenilin-1 double-transgenic mice", Neurosci Left; 306:116-120.

Written Opinion, dated Apr. 3, 2012 of International application No. PCT/US11/45948.

Wu et al., 1999, "Humanization of a murine monoclonal antibody by simultaneous optimization of framework and CDR residues", J Mol Biol; 294:151-162.

U.S. Appl. No. 13/568,896, filed Aug. 7, 2012, Pfeifer et al.

Abuchowski et al., 1977, "Effect of covalent attachment of polyethylene glycol on immunogenicity and circulating life of bovine liver catalase", J Biol Chem; 252(11):3582-3586.

Adolfsson et al., 2012, "An effector-reduced anti-β-amyloid (Aβ) antibody with unique aβ binding properties promotes neuroprotection and glial engulfment of Aβ", J Neurosci; 32(28):9677-9689.

Bandyopadhyay et al., 2006, "Interleukin-1alpha stimulates non-amyloidogenic pathway by alpha-secretase (ADAM-10 and ADAM-17) cleavage of APP in human astrocytic cells involving p38 MAP kinase", J Neurosci Res; 84:106-118.

Bateman et al., 2007, "Requirement of aggregation propensity of Alzheimer amyloid peptides for neuronal cell surface binding", BMC Neurosci; 8:29 pp. 1-13.

Bitan et al., 2003, "Amyloid beta-protein (Abeta) assembly: Abeta 40 and Abeta42 oligomerize through distinct pathways", Proc Natl Acad Sci USA; 100:330-335.

Campbell, 2001, "Beta-amyloid: friend or foe", Med Hypotheses; 56(3):388-391.

Casas et al., 2004, "Massive CA1/2 neuronal loss with intraneuronal and N-terminal truncated Abeta42 accumulation in a novel Alzheimer transgenic model", Am J Pathol; 165:1289-1300.

Clark, 1997, "IgG effector mechanisms", Chem Immuol; 65:88-110.

Cleary et al., 2005, "Natural oligomers of the amyloid-beta protein specifically disrupt cognitive function", Nat Neurosci; 8:79-84.

Cox et al., 1994, "A directory of human germ-line V kappa segments reveals a strong bias in their usage", Eur J Immunol; 24:827-836.

Delgado et al., 2008, "Vasoactive intestinal peptide protects against beta-amyloid-induced neurodegeneration by inhibiting microglia activation at multiple levels", Glia; 56:1091-1103.

Doyle et al., 2004, "Toll-like receptors induce a phagocytic gene program through p38", J Exp Med; 199:81-90.

Esler et al., 1996, "Point substitution in the central hydrophobic cluster of a human beta-amyloid congener disrupts peptide folding and abolishes plaque competence", Biochemistry; 35:13914-13921.

Gallagher et al., 1997, "Regulation of stress-induced cytokine production by pyridinylimidazoles; inhibition of CSBP kinase", Bioorg Med Chem; 5:49-64.

Gessner et al., 1998, "The IgG Fc receptor family", Ann Hematol; 76:231-248.

Gouras et al., 2000, "Intraneuronal Abeta42 accumulation in human brain", Am J Pathol; 156:15-20.

Haass et al., 1992, "Amyloid beta-peptide is produced by cultured cells during normal metabolism", Nature; 359:322-327.

Haass et al., 2007, "Soluble protein oligomers in neurodegeneration: lesions from the Alzheimer's amyloid beta-peptide", Nature Reviews; 8:101-112.

Hickman et al., 2008, "Microglial dysfunction and defective beta-amyloid clearance pathways in aging Alzheimer's disease mice", J Neurosci; 28:8354-8360.

Hieter et al., 1980, "Cloned human and mouse kappa immunoglobulin constant and J region genes conserve homology in functional segments", Cell; 22(1 Pt 1):197-207.

Holmes et al., 2008, "Long-tell' effects of Abeta42 immunisation in Alzheimer's disease: follow-up of a randomized, placebo-controlled phase I trial", Lancet; 372:216-223.

Kabat et al., 1991, "Sequences of proteins of immunological interest", U.S. Department of Health and Human Services; pp. XV-XVI.

Kayed et al., 2003, "Common structure of soluable amyloid oligomers implies common mechanism of pathogenesis", Science; 300:486-489.

Lambert et al., 1998, "Diffusable, nonfibrillar ligands derived from Abeta1-42 are potent central nervous system neurotoxins", Proc Natl Acad Sci USA; 95:6448-6453.

Lee et al., 1994, "A protein kinase involved in the regulation of inflammatory cytokine biosynthesis", Nature; 372:739-746.

Lee et al., 2000, "p38 map kinase regulate TNF-alpha production in huma strocytes and microglia by multiple mechanisms", Cytokine; 12:874-880.

Lee et al., 2005, "Meningoencephalitis associated with passive immunization of a transgenic murine model of Alzheimer's amyloidosis", FEBS Lett; 579:2564-2568.

Lee et al., 2006, "Targeting amyloid-beta peptide (Abeta) oligomers by passive immunization with a conformation-selective monoclonal antibody improves learning and memory in Abeta precursor protein (APP) transgenic mice", J Biol Chem; 281:4292-4299.

Legleiter et al., 2004, "Effect of different anti-Abeta antibodies on Abeta fibrillogenesis as assessed by atomic force microscopy", J Mol Biol; 335:997-1006.

Levine et al., 1993, "Thioflavine T interaction with synthetic Alzheimer's disease beta-amyloid peptides: detection of amyloid aggregation in solution", Protein Sci; 2:404-410.

Li et al., 2004, "Tumor necrosis factor death receptor signaling cascade is required for amyloid-beta protein-induced neuron death", J Neurosci; 24:1760-1771.

Ling et al., 2003, "Amyloid precursor protein (APP) and the biology of proteolytic processing: relevance to Alzheimer's disease", Int J Biochem Cell Biol; 35:1505-1535.

Liu et al., 1998, "Amyloid beta peptide alters intracellular vesicle trafficking and cholesterol homeostasis", Proc Natl Acad Sci USA; 95:13266-13271.

Liu et al., 2009, "A novel nicotinic acetylcholine receptor subtype in basal forebrain cholinergic neurons with high sensitivity to amyloid peptides", J Neurosci; 29:918-929.

Meberg et al., 2003, "Culturing hippocampal and cortical neurons", Methods Cell Biol; 71:111-127.

Morgan, 2009, "The role of microglial in antibody-mediated clearance of amyloid-beta from the brain", CNS & Neurological Disorders—Drug Targets; 8:7-15.

Muhs et al., 2007, "Liposomal vaccines with conformation-specific amyloid peptide antigens define immune response and efficacy in APP transgenic mice", Proc Natl Acad Sci USA; 104:9810-9815.

Mulligan et al., 1980, "Expression of a bacterial gene in mammalian cells", Science; 209:1422-1427.

Nimmerjahn et al., 2006, "Fc gamma receptors: old friends and new family members", Immunity; 24:19-28.

(56) References Cited

OTHER PUBLICATIONS

Oddo et al., 2003, "Triple-transgenic model of Alzheimer's disease with plaques and tangles: intracellular Abeta and synaptic dysfunction", Neuron; 39:409-421.
Orgogozo et al., 2003, "Subacute meningoencephalitis in a subset of patients with AD after Abeta immunization", Neurology; 61:46-54.
Perry et al., 2001, "The role of TNF and its receptors in Alzheimer's disease", Neurobiol Aging; 22:873-883.
Pike et al., 1993, "Neurodegeneration induced by beta-amyloid peptides in vitro: the role of peptide assembly state", J Neurosci; 13:1676-1687.
Plant et al., 2003, "The production of amyloid beta peptide is a critical requirement for the viability of central neurons", J Neurosci; 23(13):5531-5535.
Poduslo et al., 2010, "HH domain of Alzheimer's disease Abeta provides structural basis for neuronal binding in PC12 and mouse cortical/hippocampal neurons", PLoS One; 5:e8813.
Poling et al., 2008, "Oligomers of the amyloid-beta protein disrupt working memory: confirmation with two behavioral procedures", Behav Brain Res; 193:230-234.
Ransohoff et al., 2009, "Microglial physiology: unique stimuli, specialized responses", Annu Rev Immunol; 27:119-145.
Riechmann et al., 1988, "Reshaping human antibodies for therapy", Nature; 332:323-327.
Salloway et al., 2009, "A phase 2 multiple ascending dose trial of bapineuzumab in mild to moderate Alzheimer's disease", Neurology; 73:2061-2070.
Selkoe, 2002, "Alzheimer's disease is a synaptic failure", Science; 298(5594):789-791.
Shankar et al., 2007, "Natural oligomers of the Alzheimer amyloid-beta protein induce reversible synapse loss by modulating an NMDA-type glutamate receptor-dependent signaling pathway", J Neurosci; 27:2866-2875.
Shields et al., 2001, "High resolution mapping of the binding site on human IgG1 for Fc gamma RI, Fc gamma RII, Fc gamma RIII, and FcRn and design of IgG1 variants with improved binding to the Fc gamma R", J Biol Chem; 276:6591-6604.
Simon et al., 1985, "A modified assay for interleukin-1 (IL-1)", J Immunol Methods; 84:85-94.
Spires-Jones et al., 2009, "Passive immunotherapy rapidly increases structural plasticity in a mouse model of Alzheimer disease", Neurobiol Dis; 33:213-220.
Strittmatter et al., 1993, "Apolipoprotein E: high-avidity binding to beta-amyloid and increased frequency of type 4 allele in late-onset familial Alzheimer disease", Proc Natl Acad Sci USA; 90:1977-1981.
The International Federation of Alzheimer's Disease and Related Disorders Societies I, 2009, World Alzheimer Report—2009 Executive Summary, pp. 1-21.
The Merck Index, 2006, "An Encyclopedia of Chemicals, Drugs, and Biological", 14th Edition; pp. 1422-1423, 578, and 746.
Tomlinson et al., 1992, "The repertoire of human germline VH sequences reveals about 50 groups of VH segments with different hypervariable loops", J Mol Biol; 227:776-798.
Townsend et al., 2006, "Effects secreted oligomers of amyloid beta-protein on hippocampal synaptic plasticity: a potent role for trimers", J Physiol; 572:477-492.
Turner et al., 2003, "Roles of amyloid precursor protein and its fragments in regulating neural activity, plasticity and memory", Prog Neurobiol; 70:1-32.
Vellas et al., 2009, "Long-term follow-up of patients immunized with AN1792: reduced functional decline in antibody responders", Curr Alzheimer Res; 6:144-151.
Walsh et al., 2002, "Naturally secreted oligomers of amyloid beta protein potently inhibit hippocampal long-term potentiation in vivo", Nature; 416:535-539.
Walsh et al., 2005, "The role of cell-derived oligomers of Abeta in Alzheimer's disease and avenues for therapeutic intervention", Biochem Soc Trans; 33:1087-1090.
Wang et al., 2004, "Block of long-term potentiation by naturally secreted and synthetic amyloid beta-peptide in hippocampal slices is mediated via activation of the kinases c-Jun N-terminal kinase, cyclin-dependent kinase5, and p38 mitogen-activated protein kinase as well as metabotropic glutamate receptor type 5", J Neurosci; 24:3370-3378.
Wirths et al., 2001, "Intraneuronal Abeta accumulation precedes plaque formation in beta-amyloid precursor protein and presenilin-1 double-transgenic mice", Neurosci Lett; 306:116-120.
"Comparison of 8F5 and FP12H3-C2/ACI-01-Ab-7-C2 antibodies", AC Immune, Aug. 2009, pp. 1-3.
"Staining of human Brain Sections with AC Immune's humanized ACI-01-Ab7 Antibody", Study ACI-Bonn-01, AC Immune, Sep. 26, 2006, pp. 1-4.
"Studies of Influence of Passive Vaccination with ACI-01-Ab7 on Memory Capacity in single transgenic hAPP Mice" AC Immune, 2006, pp. 1-3.
"Studies to map the Epitope of AC Immune's monoclonal Antibody ACI-01-Ab7", AC Immune, 2006, pp. 1-5.
"Study to analyze the Binding of AC Immune's monoclonal Antibody ACI-01-Ab7 to Amyloid Species in Western Blot and Dot Blot", AC Immune, 2006, pp. 1-4.
"Study to analyze the Binding of AC Immune's murine monoclonal Antibody ACI-01-Ab7 to Amyloid Species in ELISA", AC Immune, 2006, pp. 1-2.
Du et al., 2003, "Human anti-β-amyloid antibodies block beta-amyloid fibril foiation and prevent β- amyloid-induced neurotoxicity", Brain; 126(9):1935-1939.
Gelinas et al., 2004, "Immunotherapy for Alzheimer's disease", Proc Natl Acad Sci; 101(suppl. 2):14657-14662.
Hazenberg et al., 2004, "Diagnostic and therapeutic approach of systemic amyloidosis", The Netherlands Journal of Medicine; 62(4):121-128.
Kakimura et al., 2002, "Microglial activation and amyloid-β clearance induced by exogenous heat-shock proteins", FASEB J; 16(6):601-603 (express article 10.1096/fj.01-0530fje, published online Feb. 25, 2002).
Pihlgren, M., "Binding of the murine monoclonal anti-Abeta antibody ACI-01-Ab7 to Abeta1-42 monomers, oligomers, and fibers", AC Immune, 2006, pp. 1-4.
Pihlgren, M., "Study ACI-ACI-2009.03 Disaggregation of Abeta1-42 fibers by ACI-01-Ab-7C2", AC Immune, 2009, pp. 1-4.
Piorkowska and Pihlgren, "Study ACI-ACI-2009.02, Binding of ACI-01-Ab-7C2 to plaques", AC Immune, 2009, pp. 1-3.
Roher et al., 1993, "β-Amyloid-(1-42) is a major component of cerebrovascular amyloid deposits: implications for the pathology of Alzheimer disease", Proc Natl Acad Sci USA; 90:10836-10840.
Shinoda et al., 1981, "Complete amino acid sequence of the Fc region of a human delta chain", Proc Natl Acad Sci USA; 78(2):785-789.
Zhu et al., 2008, "CD45RB is a novel molecular therapeutic target to inhibit Aβ peptide-induced microglial MAPK activation", PLoS ONE; 3(5)e2135:1-12.
U.S. Appl. No. 14/494,477, filed Sep. 23, 2014, Greferath et al.
U.S. Appl. No. 60/740,866, filed Nov. 30, 2005, Holzman et al.
U.S. Appl. No. 60/778,950, filed Mar. 3, 2006, Hillen et al.
U.S. Appl. No. 60/943,499, filed Jun. 12, 2007, Watts.
Bacskai et al., 2002, "Non-Fc-mediated mechanisms are involved in clearance of amyloid-β in vivo by immunotherapy", J Neurosci, 22(18):7873-7878.
Document No. 05 submitted with the European Opposition filed Oct. 15, 2014 against EP 1976877: Extract from ATCC catalog from PTA-7243 dated Oct. 9, 2014.
Document No. 10 submitted with the European Opposition filed Oct. 15, 2014 against EP 1976877: submission dated Jan. 12, 2006 in EP 05027092.5.
Document No. 11 submitted with the European Opposition filed Oct. 15, 2014 against EP 1976877 B1: pp. 3 to 5 of the sequence listing in WO 2007/068412.
Document No. 12 submitted with the European Opposition filed Oct. 15, 2014 against EP 1976877: Declaration from Andreas Muhs dated Oct. 10, 2014.

(56) References Cited

OTHER PUBLICATIONS

Document No. 13 submitted with the European Opposition filed Oct. 15, 2014 against EP 1976877: Declaration of Hartmut Engelmann dated Oct. 14, 2014.

Document No. 18 submitted with the European Opposition filed Oct. 15, 2014 against EP 197877: International Search Report for PCTUS2006046148.

Foote and Winter, 1992, "Antibody framework residues affecting the conformation of the hypervariable loops", J Mol Biol; 224:487-499.

Giusti et al., 1987, "Somatic diversification of S107 from an antiphosphocholine to an anti-DNA autoantibody is due to a single base change in its heavy chain variable region", Proc Natl Acad Sci USA, 84:2926-2930.

Ii et al., 1996, "Beta-amyloid protein-dependent nitric oxide production from microglial cells and neurotoxicity", Brain Research; 720:93-100.

Koistinaho and Koistinaho, 2002, "Role of p38 and p44/42 mitogen-activated protein kinases in microglia", Glia, 40:175-183.

Kussie et al., 1994, "A single engineered amino acid substitution changes antibody fine specificity", J Immunol, 152:146-152.

Liu et al., 1998, "Fine mapping of the antigen-antibody interaction of scFv215, a recombinant antibody inhibiting RNA polymerase II from *Drosophila metanogaster*", Journal of Molecular Recognition, 12:103-111.

Martin, 2001, "Protein sequence and structure analysis of antibody variable domains", Kontermann & Dübel (eds.), Antibody Engineering, ch. 31, pp. 422-439.

Mesa-Gutierrez et al., 2008, "Primary localized conjunctival amyloidosis: a case report with a ten-year follow-up period", Clinical Ophthalmology, 2(3):685-687.

Muhs et al., 2006, "Improved memory capacity of amyloid precursor protein transgenic mice through passive administration of a monoclonal antibody inducing a conformational shift of amyloid-beta", Alzheimer's & Dementia: The Journal of the Alzheimer's Association; 2(3):S21.

Nelson et al., 1999, "Ocular amyloidosis and secondary glaucoma", Ophthalmology, 106(7):1363-1366.

Qiu et al., 2003, "6$\beta$-acetoxy nortropane regulated processing of amyloid precursor protein in CHOm1 cells and rat brain", European J Pharmacol, 468(1):1-8.

Queen et al., 1989, "A humanized antibody that binds to the interleukin 2 receptor.", Proc Natl Acad Sci. USA; 86(24):10029-10033.

Schildbach et al., 1993, "Heavy chain position 50 is a determinant of affinity and specificity for the anti-digoxin antibody 26-10", J Biol Chem, 268(29):21739-21747.

Schildbach et al., 1994, "Contribution of a single heavy chain residue to specificity of an anti-digoxin monoclonal antibody", Protein Science, 3:737-749.

Sri et al., 2006, "Quantitative determination of the topological propensities of amyloidogenic peptides", Biophysical Chemistry, 120:55-61.

Solomon, 2003, "Immunological approach for the treatment of Alzheimer's disease", Journal of Molecular Neuroscience; 20(3):283-286.

Sondag et al., 2009, "Beta amyloid oligomers and fibrils stimulate differential activation of primary microglia", Journal of Neuroinflammation; 6(1):1-13.

Tamura et al., 2000, "Structural correlates of an anticarcinoma antibody: identification of specificity-determining residues (SDRs) and development of a minimally immunogenic antibody variant by retention of SDRs only", J Immunol, 164(3):1432-1441.

Tomlinson et al., 1995, "The structural repertoire of the human V kappa domain", EMBO J; 14(18):4628-4638.

Winter and Harris, 1993, "Humanized antibodies", Immunology Today; 14(6):243-246.

Xiang et al., 2000, "Study of B72.3 combining sites by molecular modeling and site directed mutagenesis", Protein Eng, 13(5):339-344.

Franciosi et al., 2006, "Broad-Spectrum Effects of 4-Aminopyridine to Modulate Amyloid $\beta_{1-42}$—Induced Cell Signaling and Functional Responses in Human Microglia," J Neurosci, 26(45):11652-64.

SG201300518-6 Search Report issued on Apr. 7, 2015.

SG0201300518-6 Written Opinion issued on Apr. 7, 2015.

* cited by examiner

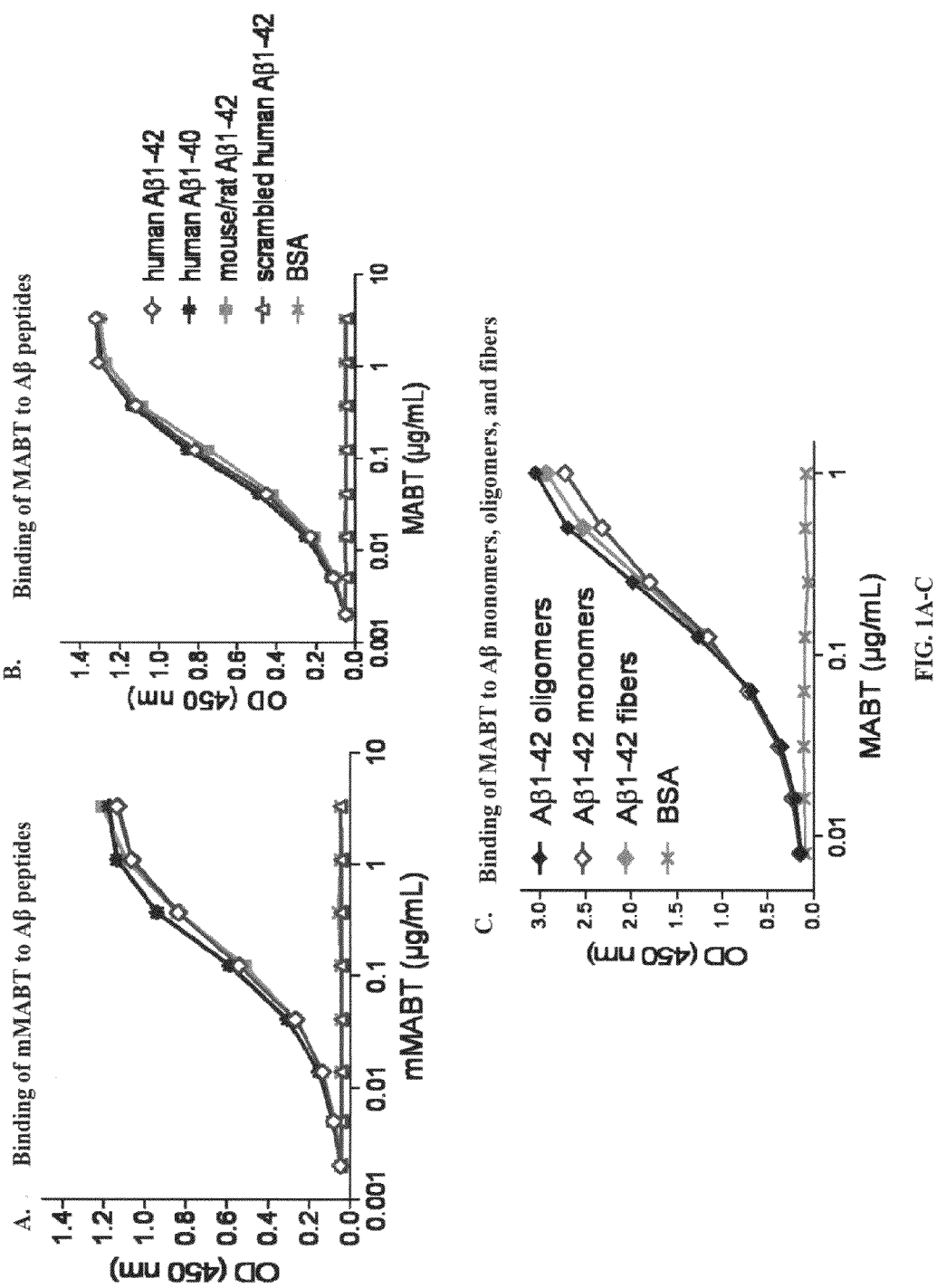
FIG. 1A-C

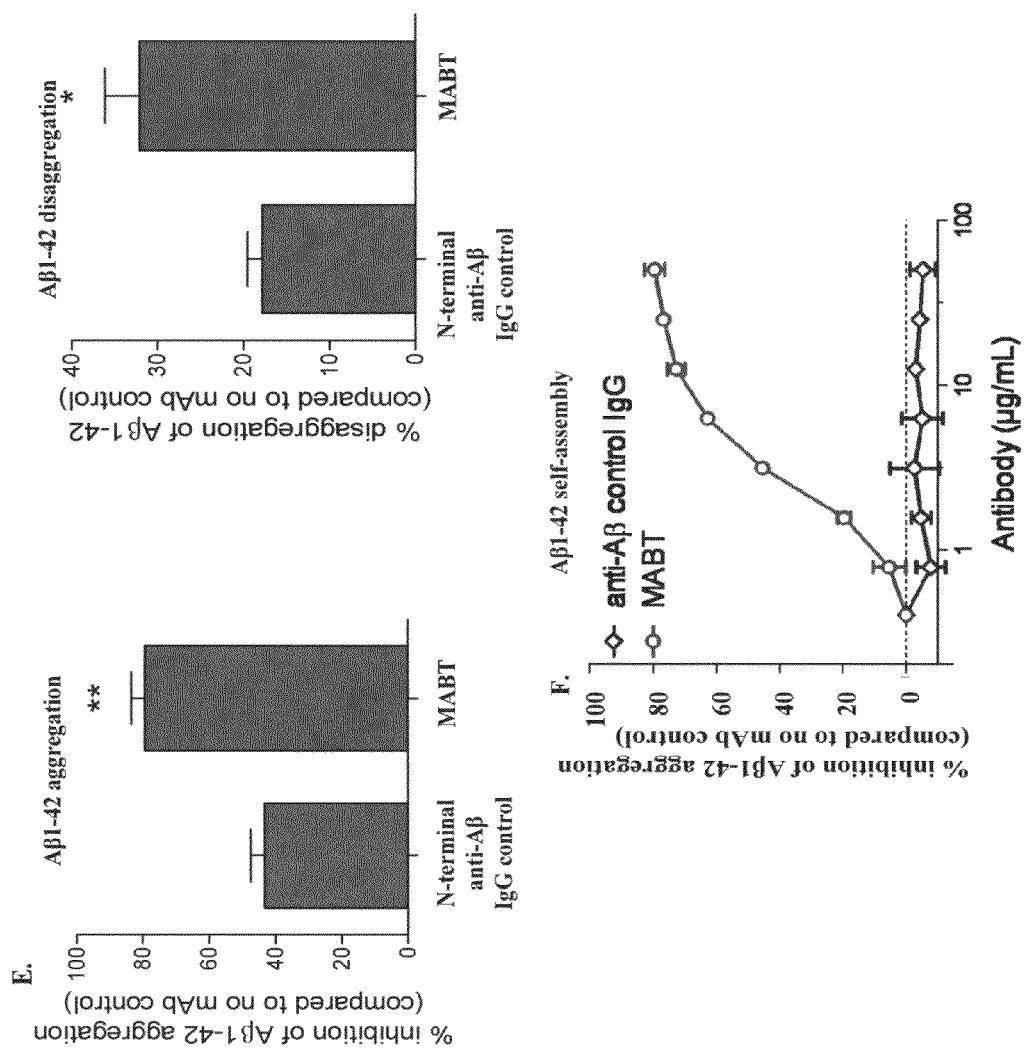
FIG. 1E-F

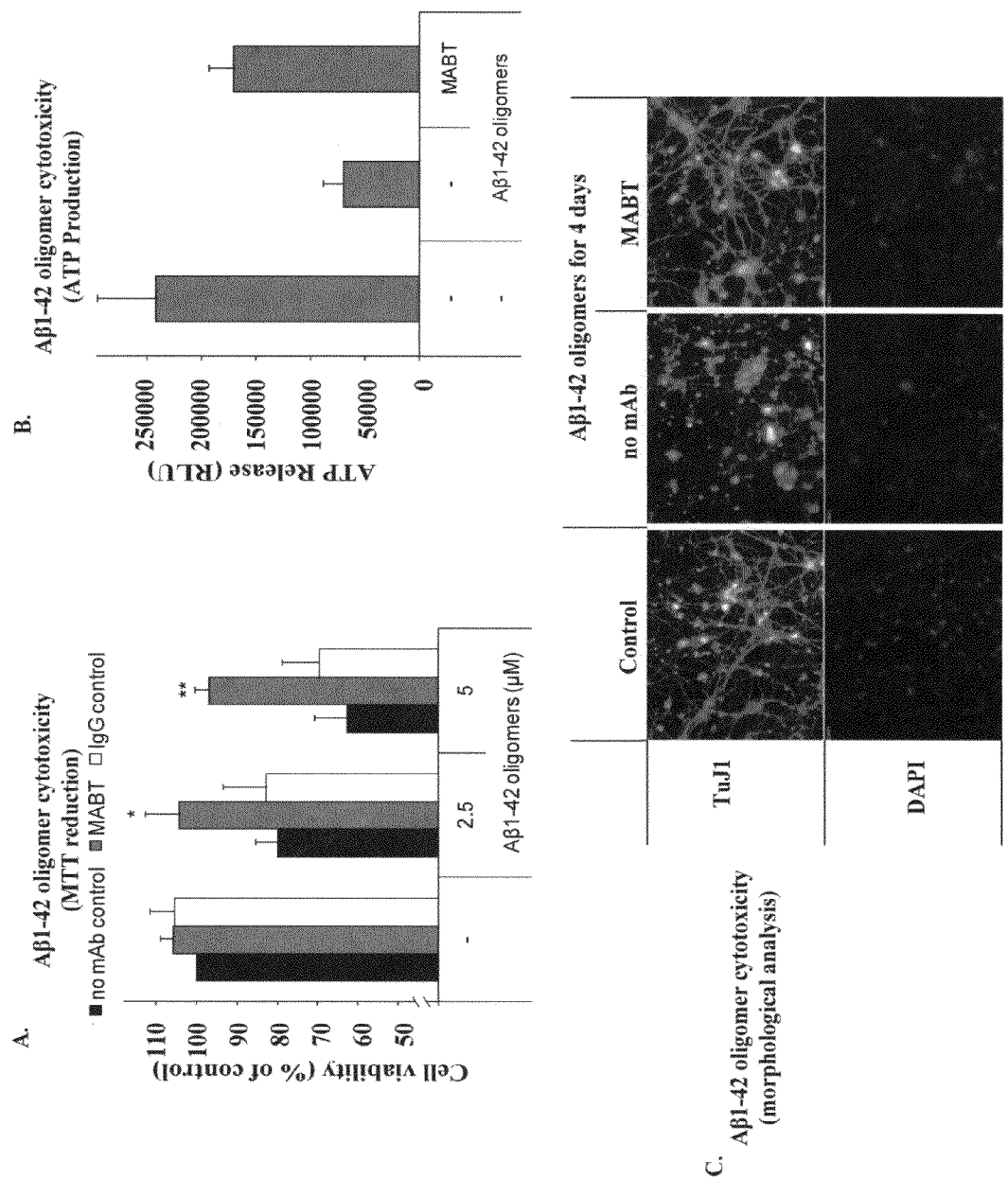
FIG. 2A-C

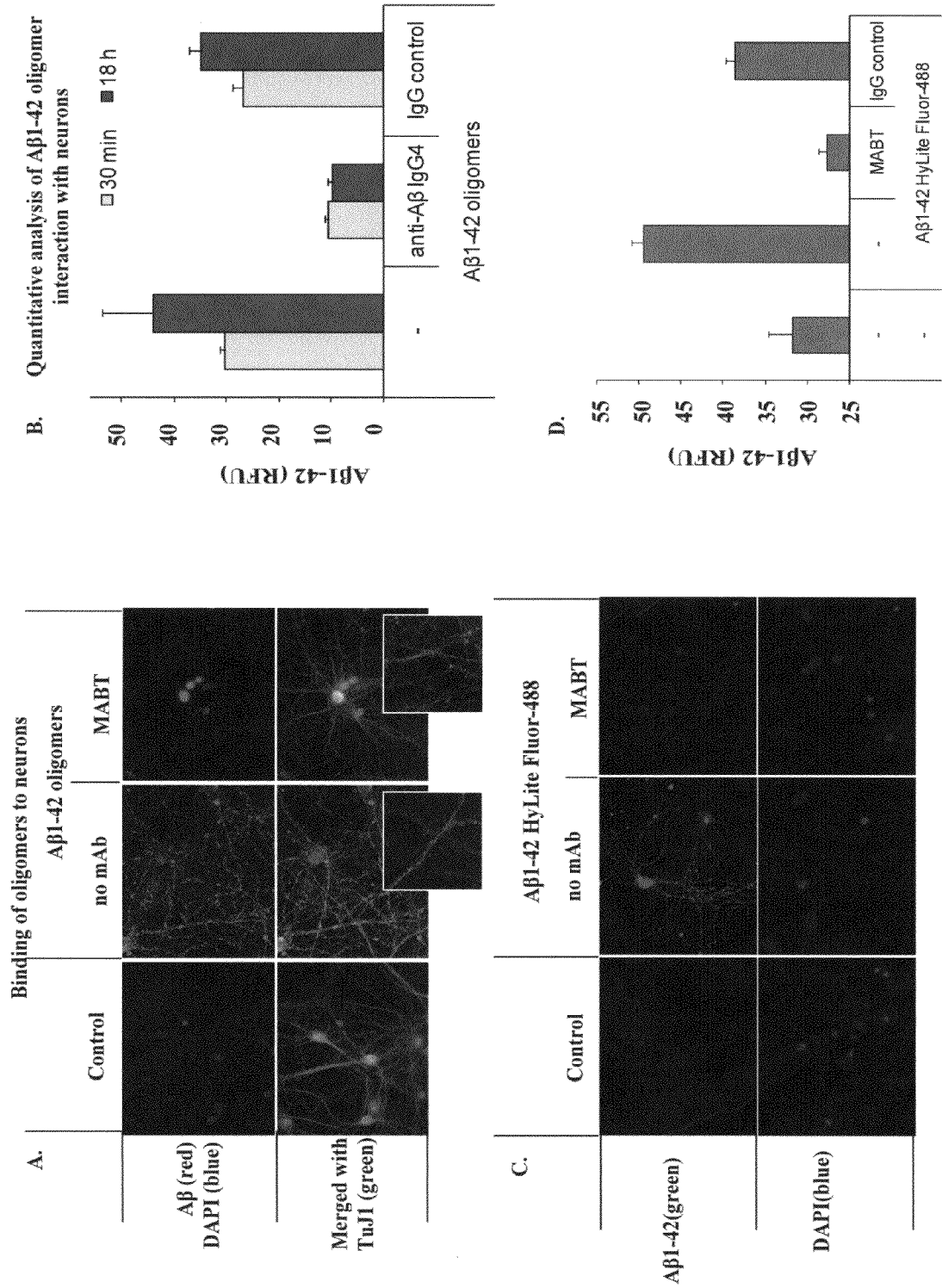
FIG. 3A-D

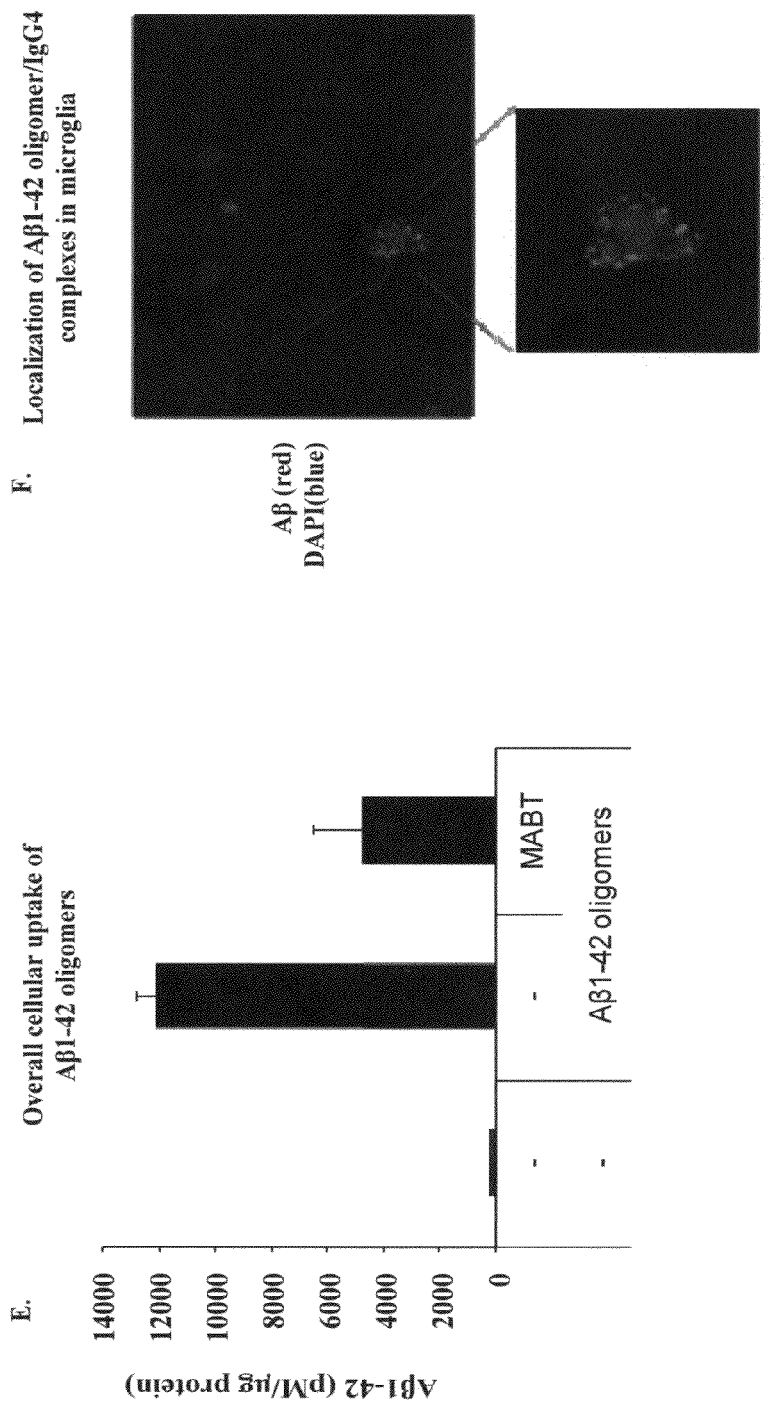
FIG. 3E-F

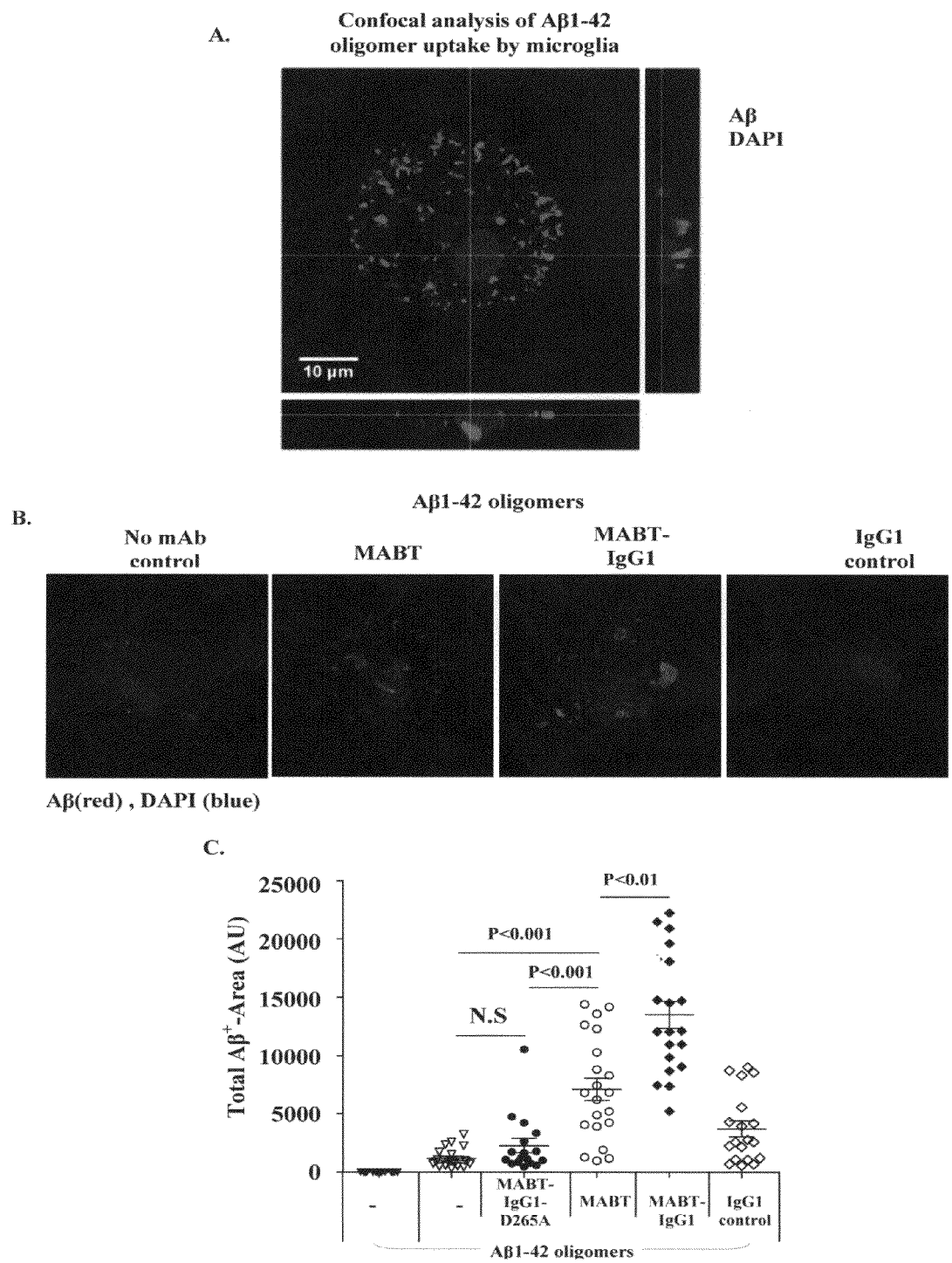
FIG. 4A-C

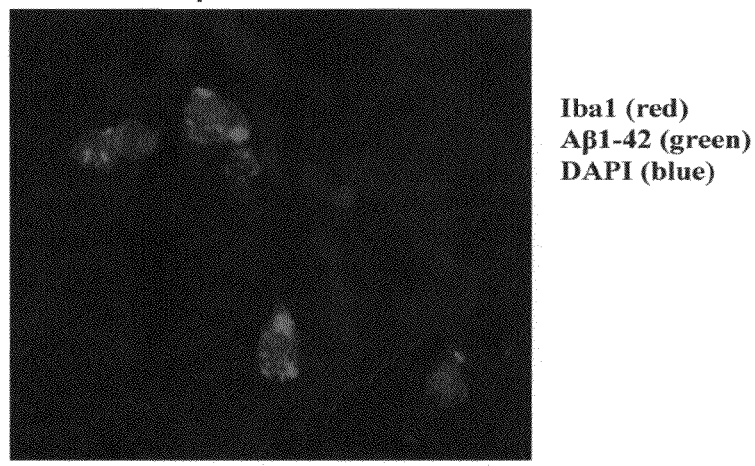
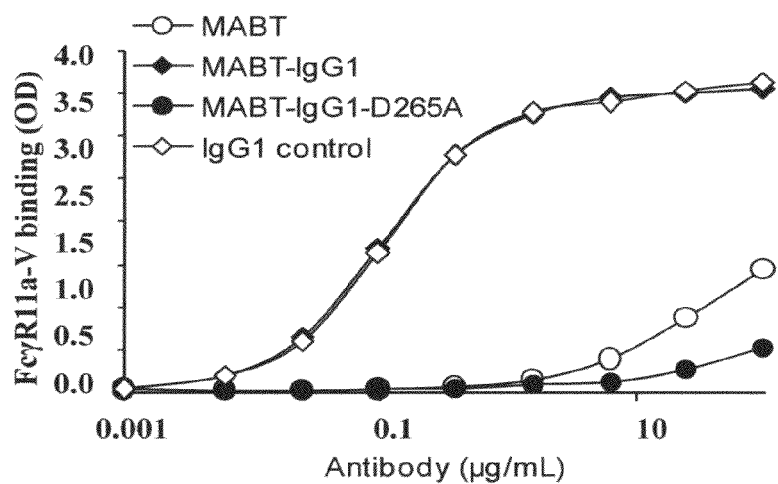
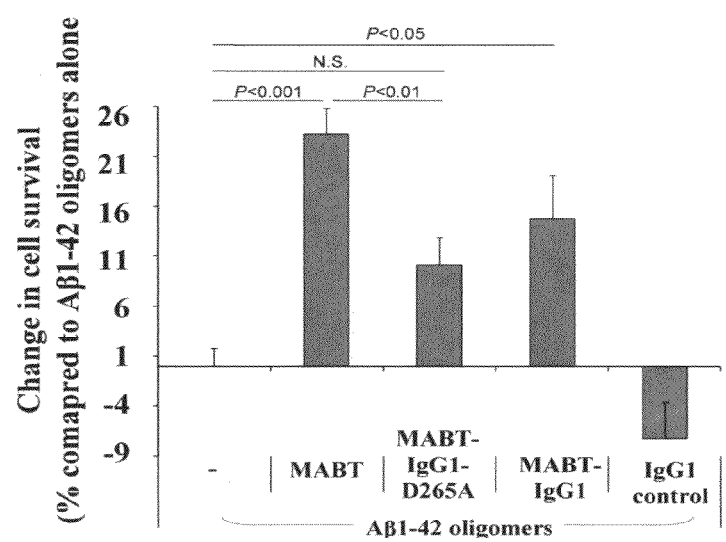
FIG. 4D-F

Figure 5
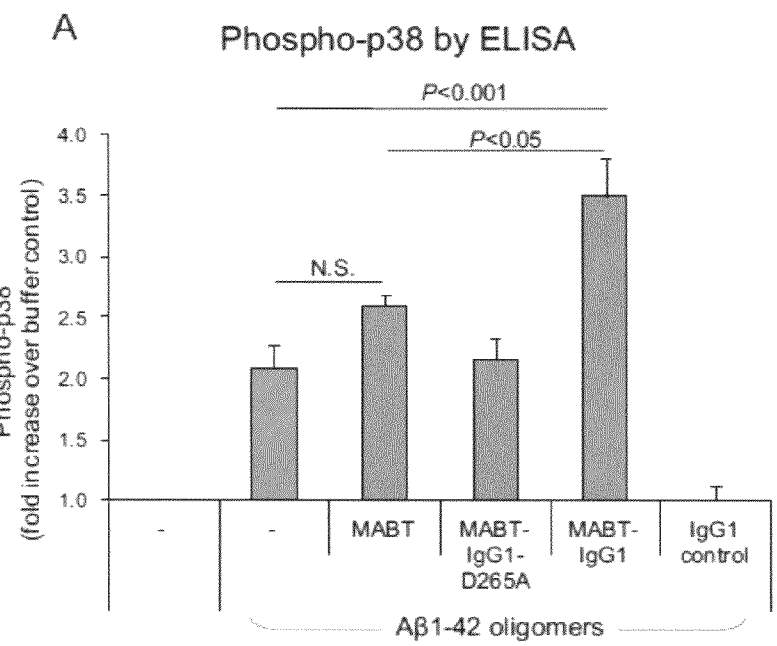
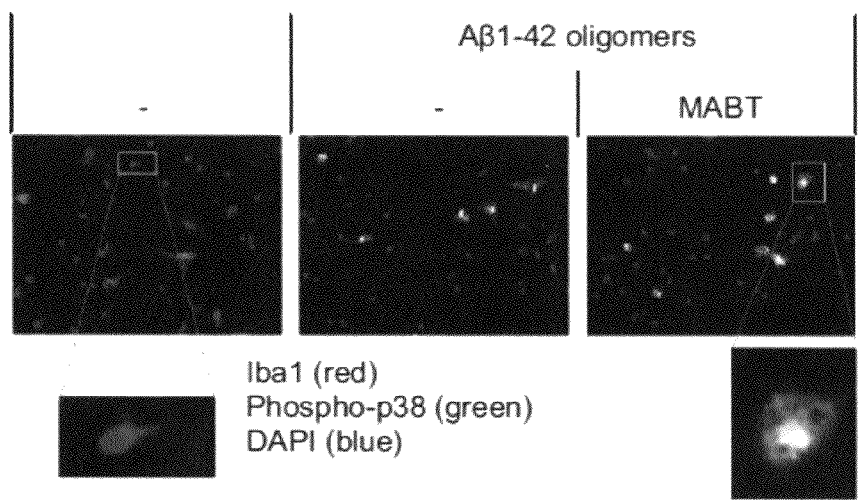

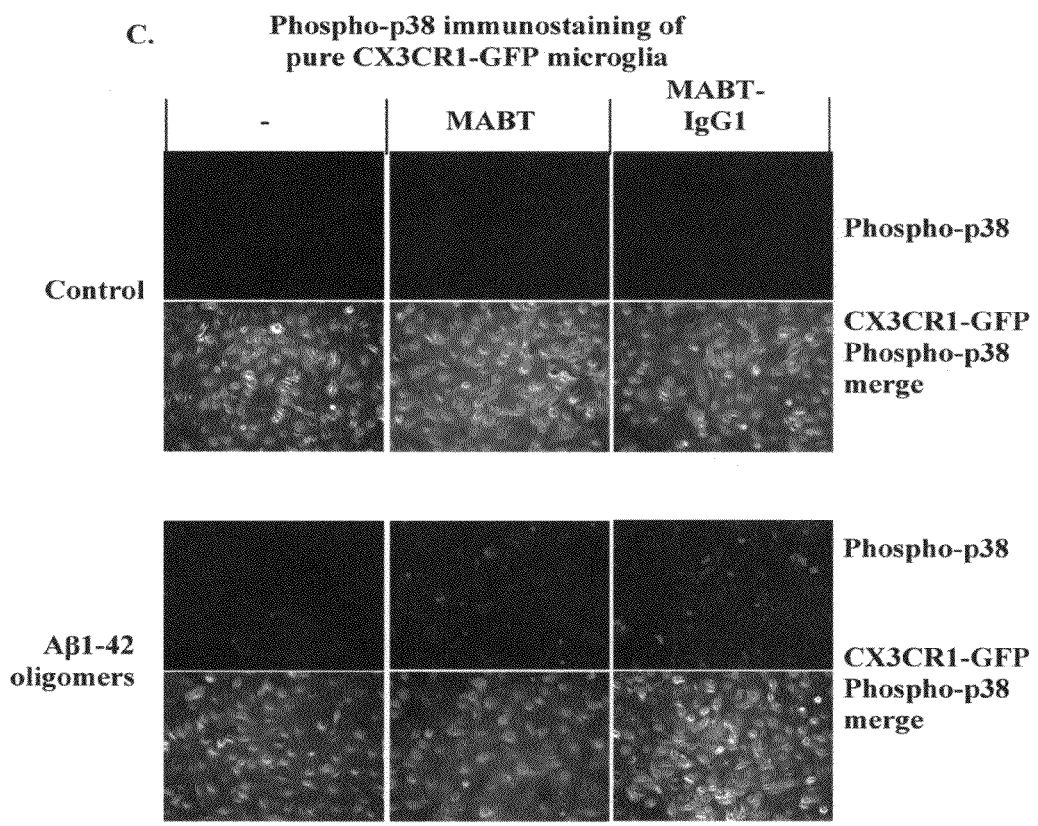
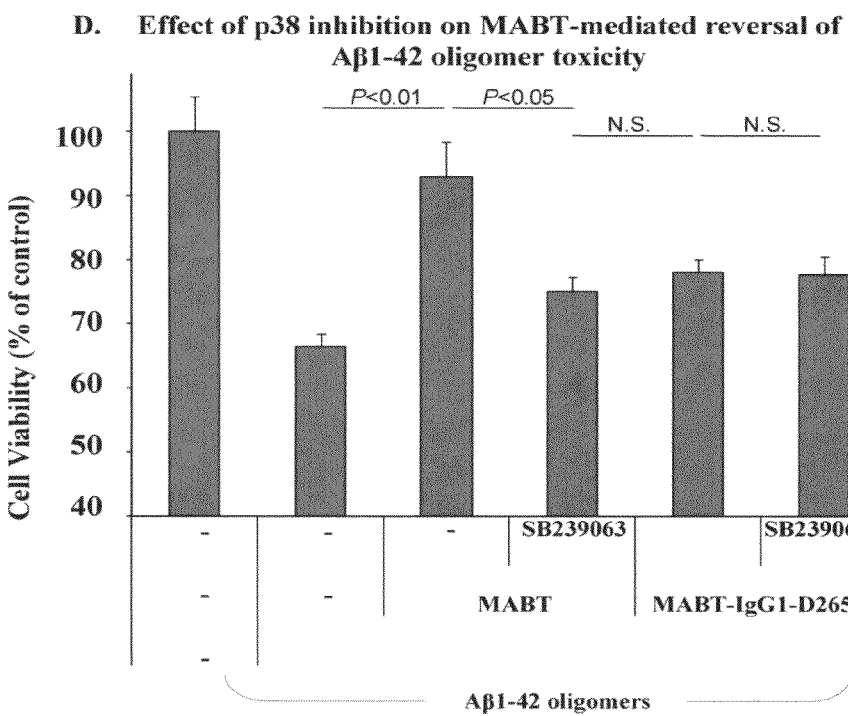
FIG. 5C-D

SEQUENCE LISTING

```
<160> NUMBER OF SEQ ID NOS: 24

<210> SEQ ID NO 1
<211> LENGTH: 10
<212> TYPE: PRT
<213> ORGANISM: Mus musculus
<220> FEATURE:
<223> OTHER INFORMATION: MABT humanised heavy chain variable region
      (CDR1)

<400> SEQUENCE: 1

Gly Phe Thr Phe Ser Ser Tyr Gly Met Ser
1               5                   10

<210> SEQ ID NO 2
<211> LENGTH: 17
<212> TYPE: PRT
<213> ORGANISM: Mus musculus
<220> FEATURE:
<223> OTHER INFORMATION: MABT humanised heavy chain variable region
      (CDR2)

<400> SEQUENCE: 2

Ser Ile Asn Ser Asn Gly Gly Ser Thr Tyr Tyr Pro Asp Ser Val Lys
1               5                   10                  15

Gly

<210> SEQ ID NO 3
<211> LENGTH: 3
<212> TYPE: PRT
<213> ORGANISM: Mus musculus
<220> FEATURE:
<223> OTHER INFORMATION: MABT humanised heavy chain variable region
      (CDR3)
```

-continued

```
<400> SEQUENCE: 3

Gly Asp Tyr
1

<210> SEQ ID NO 4
<211> LENGTH: 16
<212> TYPE: PRT
<213> ORGANISM: Mus musculus
<220> FEATURE:
<223> OTHER INFORMATION: MABT humanised light chain variable region
      (CDR1)

<400> SEQUENCE: 4

Arg Ser Ser Gln Ser Leu Val Tyr Ser Asn Gly Asp Thr Tyr Leu His
1               5                   10                  15

<210> SEQ ID NO 5
<211> LENGTH: 7
<212> TYPE: PRT
<213> ORGANISM: Mus musculus
<220> FEATURE:
<223> OTHER INFORMATION: MABT humanised light chain variable region
      (CDR2)

<400> SEQUENCE: 5

Lys Val Ser Asn Arg Phe Ser
1               5

<210> SEQ ID NO 6
<211> LENGTH: 9
<212> TYPE: PRT
<213> ORGANISM: Mus musculus
<220> FEATURE:
<223> OTHER INFORMATION: MABT humanised light chain variable region
      (CDR3)

<400> SEQUENCE: 6

Ser Gln Ser Thr His Val Pro Trp Thr
1               5

<210> SEQ ID NO 7
<211> LENGTH: 112
<212> TYPE: PRT
<213> ORGANISM: Artificial sequence
<220> FEATURE:
<223> OTHER INFORMATION: artificial humanized MABT variable light chain

<400> SEQUENCE: 7

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110
```

```
<210> SEQ ID NO 8
<211> LENGTH: 219
<212> TYPE: PRT
<213> ORGANISM: artificial sequence
<220> FEATURE:
<223> OTHER INFORMATION: artificial humanized MABT light chain

<400> SEQUENCE: 8

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 9
<211> LENGTH: 107
<212> TYPE: PRT
<213> ORGANISM: artificial sequence
<220> FEATURE:
<223> OTHER INFORMATION: artificial humanized MABT light chain constant
      region

<400> SEQUENCE: 9

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80
```

Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105

<210> SEQ ID NO 10
<211> LENGTH: 112
<212> TYPE: PRT
<213> ORGANISM: artificial sequence
<220> FEATURE:
<223> OTHER INFORMATION: artificial humanized MABT variable heavy chain

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ala Ser Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Ser Gly Asp Tyr Trp Gly Gln Gly Thr Thr Val Thr Val Ser Ser
            100                 105                 110

<210> SEQ ID NO 11
<211> LENGTH: 439
<212> TYPE: PRT
<213> ORGANISM: artificial sequence
<220> FEATURE:
<223> OTHER INFORMATION: artificial humanized MABT heavy chain

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ala Ser Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Ser Gly Asp Tyr Trp Gly Gln Gly Thr Thr Val Thr Val Ser Ser
            100                 105                 110

Ala Ser Thr Lys Gly Pro Ser Val Phe Pro Leu Ala Pro Cys Ser Arg
            115                 120                 125

Ser Thr Ser Glu Ser Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
            165                 170                 175

```
Leu Ser Ser Val Val Thr Val Pro Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Pro Cys Pro Ala Pro
    210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
            245                 250                 255

Asp Val Ser Gln Glu Asp Pro Glu Val Gln Phe Asn Trp Tyr Val Asp
        260                 265                 270

Gly Val Glu Val His Asn Ala Lys Thr Lys Pro Arg Glu Glu Gln Phe
    275                 280                 285

Asn Ser Thr Tyr Arg Val Val Ser Val Leu Thr Val Leu His Gln Asp
        290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
            325                 330                 335

Glu Pro Gln Val Tyr Thr Leu Pro Pro Ser Gln Glu Glu Met Thr Lys
        340                 345                 350

Asn Gln Val Ser Leu Thr Cys Leu Val Lys Gly Phe Tyr Pro Ser Asp
    355                 360                 365

Ile Ala Val Glu Trp Glu Ser Asn Gly Gln Pro Glu Asn Asn Tyr Lys
370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
            405                 410                 415

Cys Ser Val Met His Glu Ala Leu His Asn His Tyr Thr Gln Lys Ser
        420                 425                 430

Leu Ser Leu Ser Leu Gly Lys
            435

<210> SEQ ID NO 12
<211> LENGTH: 326
<212> TYPE: PRT
<213> ORGANISM: Homo sapiens
<220> FEATURE:
<223> OTHER INFORMATION: IG GAMMA-4 CHAIN C REGION modified

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95
```

```
Arg Val Glu Ser Lys Tyr Gly Pro Pro Cys Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 13
<211> LENGTH: 51
<212> TYPE: DNA
<213> ORGANISM: Mus musculus
<220> FEATURE:
<223> OTHER INFORMATION: MABT humanised heavy chain variable region
      (CDR2)

<400> SEQUENCE: 13
agcatcaata gtaatggtgg tagcacctat tatccagaca gtgtgaaggg c          51

<210> SEQ ID NO 14
<211> LENGTH: 9
<212> TYPE: DNA
<213> ORGANISM: Mus musculus
<220> FEATURE:
<223> OTHER INFORMATION: MABT humanised heavy chain variable region
      (CDR3)

<400> SEQUENCE: 14 ggtgactac                                                          9

<210> SEQ ID NO 15
<211> LENGTH: 49
<212> TYPE: DNA
<213> ORGANISM: Mus musculus
<220> FEATURE:
<223> OTHER INFORMATION: MABT humanised light chain variable region
      (CDR1)
```

<400> SEQUENCE: 15
agatctagtc agagccttgt atatagtaat ggagacacct atttacatt        49

<210> SEQ ID NO 16
<211> LENGTH: 336
<212> TYPE: DNA
<213> ORGANISM: artificial sequence
<220> FEATURE:
<223> OTHER INFORMATION: artificial humanized MABT variable light chain

<400> SEQUENCE: 16
gatattgtga tgacccaatc tccactctcc ctgcctgtca ctcctggtga gcctgcctcc        60
atctcttgca gatctagtca gagccttgta tatagtaatg gagacaccta tttacattgg       120
tacctgcaga agccaggcca gtctccacag ctcctgatct acaaagtttc caaccgattt       180
tctggggtcc cagacaggtt cagtggcagt ggatcaggga cagatttcac actcaagatc       240
agcagagtgg aggctgagga tgtgggagtt tattactgct ctcaaagtac acatgttcct       300
tggacgttcg gccaaggcac caaggtggaa atcaaa                                 336

<210> SEQ ID NO 17
<211> LENGTH: 657
<212> TYPE: DNA
<213> ORGANISM: artificial sequence
<220> FEATURE:
<223> OTHER INFORMATION: artificial humanized MABT light chain

<400> SEQUENCE: 17
gatattgtga tgacccaatc tccactctcc ctgcctgtca ctcctggtga gcctgcctcc        60
atctcttgca gatctagtca gagccttgta tatagtaatg gagacaccta tttacattgg       120
tacctgcaga agccaggcca gtctccacag ctcctgatct acaaagtttc caaccgattt       180
tctggggtcc cagacaggtt cagtggcagt ggatcaggga cagatttcac actcaagatc       240
agcagagtgg aggctgagga tgtgggagtt tattactgct ctcaaagtac acatgttcct       300
tggacgttcg gccaaggcac caaggtggaa atcaaaagga ctgtggctgc accatctgtc       360
ttcatcttcc cgccatctga tgagcagttg aaatctggaa ctgcctctgt tgtgtgcctg       420
ctgaataact tctatcccag agaggccaaa gtacagtgga aggtggataa cgccctccaa       480
tcgggtaact cccaggagag tgtcacagag caggacagca aggacagcac ctacagcctc       540
agcagcaccc tgacgctgag caaagcagac tacgagaaac acaaagtcta cgcctgcgaa       600
gtcacccatc agggcctgag ctcgcccgtc acaaagagct tcaacagggg agagtgt         657

<210> SEQ ID NO 18
<211> LENGTH: 321
<212> TYPE: DNA
<213> ORGANISM: Homo sapiens
<220> FEATURE:
<223> OTHER INFORMATION: artificial humanized MABT light chain constant
      region

<400> SEQUENCE: 18
aggactgtgg ctgcaccatc tgtcttcatc ttcccgccat ctgatgagca gttgaaatct        60
ggaactgcct ctgttgtgtg cctgctgaat aacttctatc ccagagaggc caaagtacag       120
tggaaggtgg ataacgccct ccaatcgggt aactcccagg agagtgtcac agagcaggac       180
agcaaggaca gcacctacag cctcagcagc accctgacgc tgagcaaagc agactacgag       240

```
aaacacaaag tctacgcctg cgaagtcacc catcagggcc tgagctcgcc cgtcacaaag      300
agcttcaaca ggggagagtg t                                                321

<210> SEQ ID NO 19
<211> LENGTH: 336
<212> TYPE: DNA
<213> ORGANISM: artificial sequence
<220> FEATURE:
<223> OTHER INFORMATION: artificial humanized MABT variable heavy chain

<400> SEQUENCE: 19
gaggtgcagc tggtcgagtc tggggggaggc ttagtgcagc tggagggtc cctgagactc       60 tcctgtgcag cctctggatt cactttcagt agctatggca tgtcttgggt tcgccaggct      120
ccaggcaagg gtctcgaatt ggtcgcaagc atcaatagta atggtggtag cacctattat      180
ccagacagtg tgaagggccg attcaccatc tccagagaca atgccaagaa ctccctgtac      240
ctgcaaatga acagtctgag agctgaggac accgccgtgt attactgtgc aagtggtgac      300
tactggggcc aaggcaccac tgtcacagtc tcctca                                336

<210> SEQ ID NO 20
<211> LENGTH: 1317
<212> TYPE: DNA
<213> ORGANISM: artificial sequence
<220> FEATURE:
<223> OTHER INFORMATION: artificial humanized MABT heavy chain

<400> SEQUENCE: 20
gaggtgcagc tggtcgagtc tggggggaggc ttagtgcagc tggagggtc cctgagactc       60 tcctgtgcag cctctggatt cactttcagt agctatggca tgtcttgggt tcgccaggct      120
ccaggcaagg gtctcgaatt ggtcgcaagc atcaatagta atggtggtag cacctattat      180
ccagacagtg tgaagggccg attcaccatc tccagagaca atgccaagaa ctccctgtac      240
ctgcaaatga acagtctgag agctgaggac accgccgtgt attactgtgc aagtggtgac      300
tactggggcc aaggcaccac tgtcacagtc tcctcagctt ccaccaaggg cccatccgtc      360
ttccccctgg cgccctgctc cagatcgacc tccgagagca cagccgccct gggctgcctg      420
gtcaaggact acttccccga accggtgacg gtgtcgtgga actcaggcgc cctgaccagc      480
ggcgtgcaca ccttcccggc tgtcctacag tcctcaggac tctactccct cagcagcgtg      540
gtgaccgtgc cctccagcag cttgggcacg aagacctaca cctgcaacgt agatcacaag      600
cccagcaaca ccaaggtgga caagagagtt gagtccaaat atggtccccc gtgtccccca      660
tgcccagcac ctgagttcct ggggggacca tcagtcttcc tgttcccccc aaaacccaag      720
gacactctca tgatctcccg gacccctgag gtcacgtgcg tggtggtgga cgtgagccag      780
gaagaccccg aggtccagtt caactggtac gtggatggcg tggaggtgca taatgccaag      840
acaaagccgc gggaggagca gttcaacagc acgtaccgtg tggtcagcgt cctcaccgtc      900
ctgcaccagg actggctgaa cggcaaggag tacaagtgca aggtctccaa caaaggcctc      960
ccgtcctcca tcgagaaaac catctccaaa gccaaagggc agccccgaga gccacaggtg     1020
tacaccctgc ccccatccca ggaggagatg accaagaacc aggtcagcct gacctgcctg     1080
gtcaaaggct tctaccccag cgacatcgcc gtggagtggg agagcaatgg gcagccggag     1140
aacaactaca agaccacgcc tcccgtcctc gattccgacg gctccttctt cctctacagc     1200
aggctaaccg tggacaagag caggtggcag gaggggaatg tcttctcatg ctccgtgatg     1260
catgaggctc tgcacaacca ctacacacag aagagcctct ccctgtctct gggtaaa        1317
```

```
<210> SEQ ID NO 21
<211> LENGTH: 981
<212> TYPE: DNA
<213> ORGANISM: Homo sapiens
<220> FEATURE:
<223> OTHER INFORMATION: artificial humanized MABT heavy chain constant
      region

<400> SEQUENCE: 21
gcttccacca agggcccatc cgtcttcccc ctggcgccct gctccagatc gacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccgtgtcc cccatgccca gcacctgagt tcctgggggg accatcagtc     360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt cctcgattcc     840
gacggctcct tcttcctcta cagcaggcta accgtggaca agagcaggtg gcaggagggg     900
aatgtcttct catgctccgt gatgcatgag gctctgcaca accactacac acagaagagc     960
ctctccctgt ctctgggtaa a                                              981

<210> SEQ ID NO 22
<211> LENGTH: 5
<212> TYPE: PRT
<213> ORGANISM: Homo sapiens
<220> FEATURE:
<223> OTHER INFORMATION: Typical amino acid sequence preceding HCDR2

<400> SEQUENCE: 22

Leu Glu Trp Ile Gly
1               5

<210> SEQ ID NO 23
<211> LENGTH: 7
<212> TYPE: PRT
<213> ORGANISM: Artificial Sequence
<220> FEATURE:
<223> OTHER INFORMATION: alternative CDRL2 sequence

<400> SEQUENCE: 23

Arg Val Ser Asn Arg Phe Ser
1               5

<210> SEQ ID NO 24
<211> LENGTH: 7
<212> TYPE: PRT
<213> ORGANISM: Artificial Sequence
<220> FEATURE:
<223> OTHER INFORMATION: alternative CDRL2 sequence
```

```
<400> SEQUENCE: 24

Lys Val Ser Ser Arg Phe Ser
1               5
```

METHODS FOR IDENTIFYING SAFE AND FUNCTIONAL HUMANIZED ANTIBODIES

The present application claims benefit of priority from U.S. provisional patent application No. 61/400,650 filed on Jul. 30, 2010 which is incorporated herein by reference in its entirety.

SEQUENCE LISTING

The present specification contains a Sequence Listing, which has been submitted in electronic format via EFS-Web and is hereby incorporated by reference in its entirety. The Sequence Listing is provided as a computer readable format (CRF) file entitled Substitute Seqlisting12593-020-999 which was created on Apr. 23, 2015, and is 20,941 bytes in size.

1. INTRODUCTION

The present invention is related to methods and compositions for the safe and functional treatment of amyloidosis, a group of disorders and abnormalities associated with amyloid protein, such as Alzheimer's disease.

2. BACKGROUND OF THE INVENTION

Amyloidosis is not a single disease entity but rather a diverse group of progressive disease processes characterized by extracellular tissue deposits of a waxy, starch-like protein called amyloid, which accumulates in one or more organs or body systems. As the amyloid deposits accumulate, they begin to interfere with the normal function of the organ or body system. There are at least fifteen different types of amyloidosis. The major forms are primary amyloidosis without known antecedent, secondary amyloidosis following some other condition, and hereditary amyloidosis.

Secondary amyloidosis occurs during chronic infection or inflammatory disease, such as tuberculosis, a bacterial infection called familial Mediterranean fever, bone infections (osteomyelitis), rheumatoid arthritis, inflammation of the small intestine (granulomatous ileitis), Hodgkin's disease, and leprosy.

Amyloid deposits include amyloid P (pentagonal) component (AP), a glycoprotein related to normal serum amyloid P (SAP), and sulphated glycosaminoglycans (GAG), complex carbohydrates of connective tissue. Amyloid protein fibrils, which account for about 90% of the amyloid material, comprise one of several different types of proteins. These proteins are capable of folding into so-called "beta-pleated" sheet fibrils, a unique protein configuration which exhibits binding sites for Congo red resulting in the unique staining properties of the amyloid protein.

Many diseases of aging are based on or associated with amyloid-like proteins and are characterized, in part, by the buildup of extracellular deposits of amyloid or amyloid-like material that contribute to the pathogenesis, as well as the progression of the disease. These diseases include, but are not limited to, neurological disorders such as Alzheimer's Disease (AD), Lewy body dementia, Down's syndrome, hereditary cerebral hemorrhage with amyloidosis (Dutch type); the Guam Parkinson-Dementia complex. Other diseases which are based on or associated with amyloid-like proteins are progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including ocular disorders such as macular degeneration.

Although pathogenesis of these diseases may be diverse, their characteristic deposits often contain many shared molecular constituents. To a significant degree, this may be attributable to the local activation of pro-inflammatory pathways thereby leading to the concurrent deposition of activated complement components, acute phase reactants, immune modulators, and other inflammatory mediators (McGeer et al., 1994).

Alzheimer's Disease (AD) is a neurological disorder primarily thought to be caused by amyloid plaques, an accumulation of abnormal deposit of proteins in the brain. The most frequent type of amyloid found in the brain of affected individuals is composed primarily of Aβ fibrils. Scientific evidence demonstrates that an increase in the production and accumulation of beta-amyloid protein in plaques leads to nerve cell death, which contributes to the development and progression of AD. Loss of nerve cells in strategic brain areas, in turn, causes reduction in the neurotransmitters and impairment of memory. The proteins principally responsible for the plaque build up include amyloid precursor protein (APP) and two presenilins (presenilin I and presenilin II). Sequential cleavage of the amyloid precursor protein (APP), which is constitutively expressed and catabolized in most cells by the enzymes β and γ secretase, leads to the release of a 39 to 43 amino acid Aβ peptide. The degradation of APPs likely increases their propensity to aggregate in plaques. It is especially the Aβ(1-42) fragment that has a high propensity of building aggregates due to two very hydrophobic amino acid residues at its C-terminus. The Aβ(1-42) fragment is therefore believed to be mainly involved in, and responsible for, the initiation of neuritic plaque formation in AD and to have, therefore, a high pathological potential.

There is therefore a need for therapeutic agents that prevent the formation of amyloid plaques and/or diffuse existing plaques in patients with AD. In particular what is needed are agents capable of counteracting the physiological manifestations of the disease such as the formation of plaques associated with aggregation of fibers of the amyloid or amyloid-like peptide.

Passive immunization against beta-amyloid has become an increasingly desirable strategy as a therapeutic treatment for AD. The effectiveness of passive immunization has been demonstrated in transgenic animal models of AD, where anti-Ab therapies have been shown to reduce plaque burden and reverse behavioral deficits. In spite of overcoming hyper-activation of cytotoxic T-cells, a risk of active immunization with Ab, passive immunization still carries the risk of Fg receptor-mediated over-activation of microglia cells and complement activation, which may contribute to an inappropriate pro-inflammatory response and vasogenic edema.

Anti-amyloid beta antibodies have been described, for example, in WO 2007/068412 published Jun. 21, 2007; WO 2008/060364 published May 22, 2008; WO 2007/068412 published Jun. 21, 2007; WO 2007/068412 published Jun. 21, 2007; WO 2007/068412 published Jun. 21, 2007; WO 2007/068412 published Jun. 21, 2007; WO 2008/156621 published Dec. 24, 2008; WO 2008/156621 published Dec. 24, 2008; WO 2008/156621 published Dec. 24, 2008 (see also Table 2).

Side effects observed during treatment of patients having amyloidosis such as AD with anti-beta amyloid antibodies include inflammatory side effects, such as meningitis and meningoencephalitis, and fluid build up in the brain (cerebral edema). Therapies that reduce or eliminate the complications associated with an amyloidosis are needed.

3. SUMMARY OF THE INVENTION

The novel compositions and methods of the invention provide a safer therapeutic alternative for passive immunotherapy for amyloidosis such as Alzheimer's Disease (AD). The invention is based, in part, on the discovery of that an anti-Aβ antibody that possesses an effective neutralizing capability as well as a reduced effector function, reduces Aβ toxicity while avoiding harmful side effects as compared to previously known Aβ monoclonal antibody (mAb) therapeutics. In particular, the inventor's discovered that a humanized anti-Aβ monoclonal antibody (mAb) of an IgG4 isotype, known as MABT, was found to reduce the risk of Fcγ-receptor-mediated over-activation of microglia and to avoid complement activation. MABT binds with high affinity to multiple forms of Aβ1-42 and Aβ1-40, protected against Aβ1-42 oligomer-induced cytotoxicity, mediated uptake of neurotoxic Aβ by microglia both in vitro and in vivo. When compared to a human IgG1 wild-type subclass containing the same antigen-binding variable domains and with equal binding avidity to Aβ, MABT showed reduced activation of the stress-activated p38 mitogen-activated protein kinase (p38MAPK) in microglia, and induced less release of pro-inflammatory mediators.

The present invention is also based in part on the unexpected role of p38MAP kinase activation in microglia cells for anti-Aβ antibody-mediated neuroprotection in AD. p38MAP kinase activity is generally thought to be pro-inflammatory and thus would have been thought to contribute to the pathogenic inflammatory state of amyloidosis, such as AD. Surprisingly, however, intermediate p38MAP kinase activation in microglia cells contributes to anti-Aβ antibody-mediated neuroprotection without generation of a pathogenic inflammatory state.

Provided herein are methods and compositions for the safe treatment and/or prevention of an amyloidosis, including but not limited to Alzheimer's Disease. Amyloidosis includes, but is not limited to, neurological disorders such as Alzheimer's Disease (AD), Lewy body dementia, Down's syndrome, hereditary cerebral hemorrhage with amyloidosis (Dutch type), the Guam Parkinson-Dementia complex, as well as other diseases which are based on or associated with amyloid-like proteins such as progressive supranuclear palsy, multiple sclerosis, Creutzfeld Jacob disease, Parkinson's disease, HIV-related dementia, ALS (amyotropic lateral sclerosis), Adult Onset Diabetes, senile cardiac amyloidosis, endocrine tumors, and others, including ocular disorders such as macular degeneration, cortical visual deficits, glaucoma, optic nerve drusen, optic neuropathy, optic neuritis, cataract, ocular amyloidosis and lattice dystrophy.

In particular, provided herein are anti-Aβ antibodies with effector regions that have been selected or modified to trigger an intermediate activation of p38MAP kinase in microglia cells. Further provided herein are methods for the treatment and prevention of an amyloidosis, including but not limited to Alzheimer's Disease, wherein the dose and/or administration regimen are selected such that p38MAP kinase is activated at an intermediate level in microglia cells. In specific embodiments, a safe and functional anti-Aβ antibody has the effector region of an IgG4 antibody. In certain more specific embodiments, a safe and functional anti-Aβ antibody has the CH2 region of an IgG4 antibody. In certain specific embodiments, an intermediate level of p38 MAP kinase activation is a level above the level of p38 MAP kinase activation by toxic beta-amyloid oligomers alone but less than the level of p38 MAP kinase activation by an IgG1 anti-Aβ antibody in conjunction with the toxic beta-amyloid oligomers. In certain embodiments, the effector region of the anti-Aβ antibody is modified such that its effector function is reduced. In certain embodiments the modification can be any genetic alteration resulting in an amino acid substitution and/or a deletion.

Further provided are methods for improving the safety of an anti-Aβ antibody. In one embodiment, method is provided for improving the safety of a non-IgG4 anti-Aβ antibody comprising replacing the constant region of said non-IgG4 anti-Aβ antibody with a constant region derived from an IgG4 antibody. In another embodiment, a method is provided for improving the safety of a non-IgG4 anti-Aβ antibody comprising replacing the constant region of said non-IgG4 antibody with a constant region derived from an non IgG1 antibody. In a specific embodiment, the method for improving the safety of a non-IgG4 anti-beta-amyloid antibody is for improving the safety of an IgG1 anti-Aβ antibody.

Further provided herein is a cell culture-based assay system to test anti-Aβ antibodies for their safety and functionality to treat and/or prevent an amyloidosis, including, but not limited to Alzheimer's Disease. In certain embodiments, microglia cells are incubated with toxic beta-amyloid oligomers and the test anti-Aβ antibody. Anti-Aβ antibody-mediated uptake of beta amyloid into the microglia cells demonstrates functionality of the antibody, e.g., in mediating the clearance of beta amyloid. Anti-Aβ antibody-mediated p38 MAP kinase activation at intermediate levels in microglia cells indicates both the antibody is functional and safe. In certain embodiments, an intermediate level of p38 MAP kinase activation is a level above the level of p38 MAP kinase activation by toxic beta-amyloid oligomers alone but less than level of p38 MAP kinase activation by an IgG1 anti-Aβ antibody having the level of effector function of the wild type (i.e., unmodified IgG1 constant region). This cell culture-based assay system can be used to test anti-Aβ antibodies for their ability to protect neurons from the neurotoxic effects of Aβ. Further, this cell culture-based assay system can be used to test anti-Aβ antibodies for their ability to trigger p38 MAP kinase activation at intermediate levels.

In certain embodiments, the cell culture-based assay system further includes neurons. The survival rate of the neurons upon co-incubation with toxic beta-amyloid oligomers, the test anti-Aβ antibody, and microglia cells demonstrates the functionality of the test anti-Aβ antibody.

In certain embodiments, the cell culture-based assay system is a primary cortical cell culture. The primary cortical cell culture is incubated with toxic beta-amyloid oligomers and the test anti-Aβ antibody. Anti-Aβ antibody-mediated uptake of beta amyloid into the microglia cells indicates functionality of the antibody, e.g., in mediating the clearance of beta amyloid. Anti-Aβ antibody-mediated p38 MAP kinase activation at intermediate levels in microglia cells demonstrates both the functionality and safety of the antibody.

Further provided herein are safe and functional antibodies for the treatment and/or prevention of an amyloidosis, including, but not limited to Alzheimer's Disease. In certain embodiments, the variable region of a non-IgG4 humanized antibody which binds to Aβ is combined with the constant region of a human IgG4 antibody. In other embodiments, the variable region of an IgG1 humanized antibody which binds to Aβ is combined with the constant region of a human IgG4 antibody. In certain embodiments, the CH2 domain of a non-IgG4 humanized antibody which binds to Aβ is replaced with the CH2 domain of a human IgG4 antibody. In other embodiments, the CH2 domain of an IgG1 humanized antibody which binds to Aβ is replaced with the CH2 domain of a human IgG4 antibody. In certain embodiments, the constant region of the constant region is derived from an IgG1 antibody wherein the constant region of the IgG1 antibody is modified such that the modified constant region has a reduced or eliminated effector function.

In other embodiments, methods are provided for the treatment and/or prevention of an amyloidosis, including but not limited to Alzheimer's Disease, wherein an IgG1 anti-Aβ antibody is administered in combination with an anti-inflammatory agent such that p38 MAP kinase is activated at an intermediate level in microglia cells. In certain specific embodiments, intermediate levels of p38 MAP kinase activation are levels above the levels of p38 MAP kinase activation by toxic beta-amyloid oligomers alone but less than levels of p38 MAP kinase activation by an IgG1 anti-Aβ antibody having normal levels of effector function in the presence of oligomers alone without the anti-inflammatory agent.

3.1 Terminology

The terms "polypeptide", "peptide", and "protein", as used herein, are interchangeable and are defined to mean a biomolecule composed of amino acids linked by a peptide bond.

The terms "a", "an" and "the" as used herein are defined to mean "one or more" and include the plural unless the context is inappropriate.

The term "amyloidosis" refers to a group of diseases and disorders caused by or associated with amyloid or amyloid-like proteins and includes, but is not limited to, diseases and disorders caused by the presence or activity of amyloid-like proteins in monomeric, fibril, or polymeric state, or any combination of the three, including by amyloid plaques. Such diseases include, but are not limited it, secondary amyloidosis and age-related amyloidosis such as diseases including, but not limited to, neurological disorders such as Alzheimer's Disease (AD), diseases or conditions characterized by a loss of cognitive memory capacity such as, for example, mild cognitive impairment (MCI), Lewy body dementia, Down's syndrome, hereditary cerebral hemorrhage with amyloidosis (Dutch type), the Guam Parkinson-Dementia complex and other diseases which are based on or associated with amyloid-like proteins such as progressive supranuclear palsy, multiple sclerosis, Creutzfeld Jacob disease, Parkinson's disease, HIV-related dementia, ALS (amyotropic lateral sclerosis), inclusion-body myositis (IBM), adult onset diabetes, endocrine tumor and senile cardiac amyloidosis; and various eye diseases including macular degeneration, drusen-related optic neuropathy, and cataract due to beta-amyloid deposition.

The terms "detecting" or "detected" as used herein mean using known techniques for detection of biologic molecules such as immunochemical or histological methods and refer to qualitatively or quantitatively determining the presence or concentration of the biomolecule under investigation.

"Amyloid β," "amyloid beta," "Aβ," "β-amyloid," or "beta amyloid" is an art-recognized term and refers to amyloid β proteins and peptides, as well as modifications, fragments and any functional equivalents thereof, which may be produced by proteolytic cleavage of amyloid precursor protein (APP), and include those fragments of APP which are involved in or associated with the amyloid pathologies including, but not limited to, Aβ1-38, Aβ1-39, Aβ1-40, Aβ1-41 Aβ1-42 and Aβ1-43.

The structure and sequences of the amyloid β peptides as mentioned above are well known to one of ordinary skill in the art and methods of producing said peptides or of extracting them from brain and other tissues are described, for example, in Glenner and Wong, Biochem Biophys Res Comm 129, 885-890 (1984). Moreover, amyloid β peptides are also commercially available in various forms.

The term "isolated" means a biological molecule free from at least some of the components with which it naturally occurs.

The terms "antibody" or "antibodies" as used herein are art-recognized terms and are understood to refer to molecules or active fragments of molecules that bind to known antigens, and are used interchangeably with the terms "immunoglobulin" or "immunoglobulin molecules" and immunologically active portions of immunoglobulin molecules, i.e., portions of an immunoglobulin that contain a binding site that specifically binds an antigen. An immunoglobulin is a protein comprising one or more polypeptides substantially encoded by the immunoglobulin kappa and lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Also subclasses of the heavy chain are known. For example, IgG heavy chains in humans can be any of the IgG1, IgG2, IgG3 and IgG4 subclasses.

As used herein "specifically binds" in reference to an antibody means that the antibody binds to its target antigen with greater affinity that it does to a structurally different antigen(s).

A typical immunoglobulin structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these portions of the light and heavy chains, respectively.

Antibodies exist as full length intact antibodies or as a number of well-characterized fragments produced by digestion with various peptidases or chemicals. Thus, for example, pepsin digests an antibody below the disulfide linkages in the hinge region to produce F(ab')$_2$, a dimer of Fab which itself is a light chain joined to VH-CH1 by a disulfide bond. The F(ab')$_2$ may be reduced under mild conditions to break the disulfide linkage in the hinge region thereby converting the F(ab')$_2$ dimer into an Fab' monomer. The Fab' monomer is essentially a Fab fragment with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of ordinary skill in the art will appreciate that any of a variety of antibody fragments may be synthesized de novo either chemically or by utilizing recombinant DNA methodology. Thus, the term antibody, as used herein also includes antibody fragments either produced by the modification of whole antibodies or synthesized de novo or antibodies and fragments obtained by using recombinant DNA methodologies.

The term "antibodies" includes monoclonal antibodies, polyclonal antibodies, chimeric, single chain, bispecific, simianized, human and humanized antibodies as well as active fragments thereof. Examples of active fragments of molecules that bind to known antigens include separated light and heavy chains, Fab, Fab/c, Fv, Fab', and F(ab')$_2$ fragments, including the products of an Fab immunoglobulin expression library and epitope-binding fragments of any of the antibodies and fragments mentioned above. These active fragments can be derived by a number of techniques. For example, monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

Recombinantly made antibodies may be conventional full length antibodies, active antibody fragments known from proteolytic digestion, unique active antibody fragments such as Fv or single chain Fv (scFv), domain deleted antibodies, and the like. An Fv antibody is about 50 Kd in size and comprises the variable regions of the light and heavy chain. A single chain Fv ("scFv") polypeptide is a covalently linked VH::VL heterodimer which may be expressed from a nucleic acid including VH- and VL-encoding sequences either joined directly or joined by a peptide-encoding linker. See Huston, et al. (1988) Proc. Nat. Acad. Sci. USA, 85:5879-5883. A number of structures for converting the naturally aggregated, but chemically separated light and heavy polypeptide chains from an antibody V region into an scFv molecule which will fold into a three dimensional structure substantially similar to the structure of an antigen-binding site. See, e.g., U.S. Pat. Nos. 5,091,513, 5,132,405 and 4,956,778.

The combining site refers to the part of an antibody molecule that participates in antigen binding. The antigen binding site is formed by amino acid residues of the N-terminal variable ("V") regions of the heavy ("H") and light ("L") chains. The antibody variable regions comprise three highly divergent stretches referred to as "hypervariable regions" or "complementarity determining regions" (CDRs) which are interposed between more conserved flanking stretches known as "framework regions" (FRs). In an antibody molecule, the three hypervariable regions of a light chain (LCDR1, LCDR2, and LCDR3) and the three hypervariable regions of a heavy chain (HCDR1, HCDR2 and HCDR3) are disposed relative to each other in three dimensional space to form an antigen binding surface or pocket. The antibody combining site therefore represents the amino acids that make up the CDRs of an antibody and any framework residues that make up the binding site pocket.

The identity of the amino acid residues in a particular antibody that make up the combining site can be determined using methods well known in the art. For example, antibody CDRs may be identified as the hypervariable regions originally defined by Kabat et al. (see, "Sequences of Proteins of Immunological Interest," E. Kabat et al., U.S. Department of Health and Human Services; Johnson, G and Wu, T T (2001) Kabat Database and its applications: future directions. Nucleic Acids Research, 29: 205-206; http://immuno.bme.nwa.edu). The positions of the CDRs may also be identified as the structural loop structures originally described by Chothia and others (see Chothia and Lesk, J. Mol. Biol. 196, 901 (1987), Chothia et al., Nature 342, 877 (1989), and Tramontano et al., J. Mol. Biol. 215, 175 (1990)). Other methods include the "AbM definition" which is a compromise between Kabat and Chothia and is derived using Oxford Molecular's AbM antibody modeling software (now Accelrys) or the "contact definition" of CDRs by Macallum et al., ("Antibody-antigen interactions: contact analysis and binding site topography," J Mol Biol. 1996 Oct. 11; 262(5):732-45).

Chimeric antibodies are those in which one or more regions of the antibody are from an antibody derived from a first species and one or more regions of the antibody are from an antibody derived from a second, different species. In one embodiment, a chimeric antibody is one which includes regions from a primate immunoglobulin. A chimeric antibody for human clinical use is typically understood to have variable regions from a non-human animal, e.g. a rodent, with the constant regions from a human antibody. In contrast, a humanized antibody uses CDRs from the non-human antibody with most or all of the variable framework regions from and all the constant regions from a human antibody. A human chimeric antibody is typically understood to have the variable regions from a rodent antibody. A typical human chimeric antibody has human heavy constant regions and human light chain constant regions with the variable regions of both the heavy and light chains derived from a rodent antibody. A chimeric antibody may include some changes to a native amino acid sequence of the human constant regions and the native rodent variable region sequence. Chimeric and humanized antibodies may be prepared by methods well known in the art including CDR grafting approaches (see, e.g., U.S. Pat. Nos. 5,843,708; 6,180,370; 5,693,762; 5,585,089; 5,530,101), chain shuffling strategies (see e.g., U.S. Pat. No. 5,565,332; Rader et al., Proc. Natl. Acad. Sci. USA (1998) 95:8910-8915), molecular modeling strategies (U.S. Pat. No. 5,639,641), and the like.

A "humanized antibody" as used herein in the case of a two or greater chain antibody is one where at least one chain is humanized. A humanized antibody chain has a variable region where one or more of the framework regions are human. A humanized antibody which is a single chain is one where the chain has a variable region where one or more of the framework regions are human. The non-human portions of the variable region of the humanized antibody chain or fragment thereof is derived from a non-human source, particularly a non-human antibody, typically of rodent origin. The non-human contribution to the humanized antibody is typically provided in the form of at least one CDR region which is interspersed among framework regions derived from one (or more) human immunoglobulin(s). In addition, framework support residues may be altered to preserve binding affinity.

A "humanized antibody" may further comprise constant regions (e.g., at least one constant region or portion thereof, in the case of a light chain, and in some embodiments three constant regions in the case of a heavy chain). The constant regions of a humanized antibody, if present, typically are human in origin. Methods to obtain humanized antibodies are well known to those of ordinary skill in the art. (see, e.g., Queen et al., Proc. Natl Acad Sci USA, 86:10029-10032 (1989), Hodgson et al., Bio/Technology, 9:421 (1991)). A humanized antibody may also be obtained by a novel genetic engineering approach that enables production of affinity-matured human-like polyclonal antibodies in large animals such as, for example, rabbits and mice. See, e.g. U.S. Pat. No. 6,632,976.

The term "constant region" or, abbreviated, "CR" as used herein refers to constant regions genes of the immunoglobulin. The constant region genes encode the portion of the antibody molecule which confers effector functions. Chimeric human antibodies and humanized antibodies, typically non-human (e.g., murine), constant regions are substituted by human constant regions. The constant regions of the subject chimeric or humanized antibodies are typically derived from human immunoglobulins. The heavy chain constant region can be selected from any of the five isotypes: alpha, delta, epsilon, gamma or mu. Further, heavy chains of various subclasses (such as the IgG subclasses of heavy chains) are responsible for different effector functions and thus, by choosing the desired heavy chain constant region, antibodies with desired effector function can be produced. Constant regions that may be used within the scope of this invention are gamma 1 (IgG1), particularly an Fc region of the gamma 1 (IgG1) isotype, gamma 3 (IgG3) and especially gamma 4 (IgG4). The light chain constant region can be of the kappa or lambda type, preferably of the kappa type. In one embodiment the light chain constant region is the human kappa constant chain (Heiter et al. (1980) Cell 22:197-207) and the heavy constant chain is the human IgG4 constant chain.

The term "monoclonal antibody" is also well recognized in the art and refers to an antibody that is the product of a single cloned antibody producing cell. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces the antibody.

For the purpose of the present invention, "monoclonal antibody" is also to be understood to comprise antibodies that are produced by a mother clone which has not yet reached full monoclonality.

The antibody according to the invention may be an immunoglobulin or antibody, which is understood to have each of its binding sites identical (if multivalent) or, in the alternative, may be a bispecific antibody or a multispecific antibody.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992). A "multispecific" or "multifunctional antibody" is an artificial hybrid antibody having more than two different heavy/light chain pairs and more than two different binding sites. Multispecific antibodies can be produced using the same variety of methods as bispecific antibodies.

The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')$_2$, Fabc and/or Fv fragments. The term "antigen-binding fragment" refers to a polypeptide fragment of an immunoglobulin or antibody that binds antigen or competes with intact antibody (i.e., with the intact antibody from which they were derived) for antigen binding (i.e., specific binding). Binding fragments can be produced by recombinant DNA techniques, or by enzymatic or chemical cleavage of intact immunoglobulins. Binding fragments include Fab, Fab', F(ab')$_2$, Fabc, Fv, single chains, and single-chain antibodies.

"Fragment" also refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of another polypeptide. In a specific embodiment, a fragment of a polypeptide retains at least one function of the polypeptide.

The term "antigen" refers to an entity or fragment thereof which can bind to an antibody. An immunogen refers to an antigen which can elicit an immune response in an organism, particularly an animal, more particularly a mammal including a human. The term antigen includes regions known as antigenic determinants or epitopes which refers to a portion of the antigen (which are contacted or which play a significant role in supporting a contact reside in the antigen) responsible for antigenicity.

As used herein, the term "soluble" means the ability to partially or completely dissolve in an aqueous solution.

Also as used herein, the term "immunogenic" refers to substances which elicit the production of antibodies, T-cells and other reactive immune cells directed against an antigen of the immunogen.

The term immunogenicity as used herein refers to a measure of the ability of an antigen to elicit an immune response (humoral or cellular) when administered to a recipient. An immune response occurs when an individual produces sufficient antibodies, T-cells and other reactive immune cells against administered immunogenic compositions of the present invention to moderate or alleviate the disorder to be treated.

A humanized antibody having "reduced immunogenicity" refers to a humanized antibody exhibiting reduced immunogenicity relative to the parent antibody, e.g., the murine antibody.

A humanized antibody "substantially retaining the binding properties of the parent antibody" refers to a humanized antibody which retains the ability to specifically bind the antigen recognized by the parent antibody used to produce such humanized antibody. In some embodiments the humanized antibody will exhibit the same or substantially the same antigen-binding affinity and avidity as the parent antibody. In certain embodiments, the affinity of the antibody will not be less than 10% of the parent antibody affinity, not less than about 30% of the parent antibody affinity, or not less than 50% of the parent antibody affinity. Methods for assaying antigen-binding affinity are well known in the art and include half-maximal binding assays, competition assays, and Scatchard analysis. Suitable antigen binding assays are described in this application.

As used herein a "conservative change" refers to alterations that are substantially conformationally or antigenically neutral, producing minimal changes in the tertiary structure of the mutant polypeptides, or producing minimal changes in the antigenic determinants of the mutant polypeptides, respectively, as compared to the native protein. When referring to the antibodies and antibody fragments of the invention, a conservative change means an amino acid substitution that does not render the antibody incapable of binding to the subject receptor. Those of ordinary skill in the art will be able to predict which amino acid substitutions can be made while maintaining a high probability of being conformationally and antigenically neutral. Such guidance is provided, for example in Berzofsky, (1985) Science 229:932 940 and Bowie et al. (1990) Science 247:1306 1310. Factors to be considered that affect the probability of maintaining conformational and antigenic neutrality include, but are not limited to: (a) substitution of hydrophobic amino acids is less likely to affect antigenicity because hydrophobic residues are more likely to be located in a protein's interior; (b) substitution of physiochemically similar amino acids is less likely to affect conformation because the substituted amino acid structurally mimics the native amino acid; and (c) alteration of evolutionarily conserved sequences is likely to adversely affect conformation as such conservation suggests that the amino acid sequences may have functional importance. One of ordinary skill in the art will be able to assess alterations in protein conformation using well-known assays, such as, but not limited to microcomplement fixation methods (Wasserman et al. (1961) J. Immunol. 87:290 295; Levine et al. (1967) Meth. Enzymol. 11:928 936) and binding studies using conformation dependent monoclonal antibodies (Lewis et al. (1983) Biochem. 22:948 954).

The term "therapeutically functional amount" refers to the amount of antibody which, when administered to a human or animal, is sufficient to result in a therapeutic effect in said human or animal. The functional amount is readily determined by one of ordinary skill in the art following routine procedures.

As used herein, the terms "treat," "prevent," "preventing," and "prevention" refer to the prevention of the recurrence or onset of one or more symptoms of a disorder in a subject resulting from the administration of a prophylactic or therapeutic agent.

The term "safe and functional amount" in the context of an anti-beta amyloid antibody refers to that amount of the anti-beta amyloid antibody that, when administered to a patient with Alzheimer's disease, reduces or prevents the formation of new amyloid plaques in the patient, reduces the amyloid plaque load in the patient, and/or reduces or prevents the deterioration of, or improves the cognitive abilities of the patient and wherein no side effects, such as such as inflammatory side effects, e.g., meningitis and meningoencephalitis, and fluid build up in the brain (cerebral edema) are observed or wherein any side effects are not so severe that the treatment of the patient has to be interrupted. In certain embodiments, the formation of new amyloid plaques is reduced by at least 10%, 20%, 30%, 40%, 50%, 60%, 70%, 80%, 90%, 95%, 98%, 99%, or 100% relative to an untreated control. In certain embodiments, the amyloid plaque load is reduced by at least 10%, 20%, 30%, 40%, 50%, 60%, 70%, 80%, 90%, 95%, 98%, 99%, or 100% relative to an untreated control. In certain embodiments, the deterioration of the cognitive abilities of the patient reduced by at least 10%, 20%, 30%, 40%, 50%, 60%, 70%, 80%, 90%, 95%, 98%, 99%, or 100% relative to an untreated control. In certain embodiments, the cognitive abilities of the patient are improved by at least 10%, 20%, 30%, 40%, 50%, 60%, 70%, 80%, 90%, 95%, 98%, 99%, or 100% relative to an untreated control.

The term "non-IgG1 antibody" refers to an antibody with any constant region of one of the following isotypes IgA, IgD, IgE, IgG and IgM except that the non-IgG1 antibody does not have an IgG1 constant region that retains its wild type effector function. In specific embodiments, the non-IgG1 antibody is an IgG4 antibody. In other specific embodiments, the non-IgG1 antibody has a constant region derived from an IgG1 antibody that has been mutated such that the effector function of the resulting antibody is reduced or eliminated relative to the wild type IgG1 antibody.

The term "intermediate levels" in the context of p38 MAP kinase activation refers to levels of activation of p38 MAP kinase above the level of activation of p38 MAP kinase in the absence of a humanized non-IgG1 anti-beta amyloid antibody but below the level of p38 MAP kinase activation in the presence of the same concentration of an IgG1 anti-beta amyloid antibody which binds to beta amyloid with the same Kd as the humanized non-IgG1 anti-beta amyloid antibody.

4. DESCRIPTION OF THE FIGURES

The patent or application file contains at least one drawing executed in color. Copies of this patent or patent application publication with color drawings will be provided by the Office upon request and payment of the necessary fee.

FIG. 1 provides graphs and immunohistochemical images corresponding to the experiments described in Example 6.1 and 6.2. The anti-Aβ MABT monoclonal antibody bound with high affinity to different Aβ peptides and has anti-aggregation properties. An Aβ ELISA was used to compare mMABT (A) and MABT (B) binding to human and murine Aβ1-42 and human Aβ1-40. The MABT was also tested for binding to different Aβ1-42 assembly states (C). The MABT binds Aβ plaques present in brain sections from transgenic APP mice (D top panels) and human AD temporal neocortical sections (D bottom panels). In vitro functionality was shown by the ability of MABT to impede Aβ1-42 aggregation, and to dissemble preformed Aβ1-42 aggregates. Inhibition of Aβ1-42 aggregation, and disaggregation of pre-formed Aβ1-42 aggregates was demonstrated using a 10:1 molar ratio (Aβ1-42 to monoclonal antibody) in a ThT-based assay (E). As a control, an anti-Aβ IgG monoclonal antibody with a N-terminal epitope was used. Results show the mean (±SD) of three independent experiments. *P<0.05, **P<0.01. The MABT was also tested in an Aβ1-42 self-assembly assay that does not rely on ThT fluorescence upon binding to multimeric Aβ assemblies, as described in Methods (F). The mean (±SEM) of two assays is shown.

FIG. 2 provides graphs and immunocytochemical images corresponding to the experiments described in Example 6.3. MABT inhibits cytotoxicity of Aβ1-42 oligomers on primary mixed cortical cultures. Mixed cortical cells from P1 rats were treated with 2.5 or 5 μM Aβ1-42 oligomers with or without 100 μg/mL of MABT or an IgG control monoclonal antibody (A). An MTT assay was used to determine cell viability as described in the Methods section. The means (±SEM) of five independent experiments are shown. *P<0.05, **P<0.01. In a comparable assay, but measuring ATP production as a marker of metabolic activity, cells were treated with 10 μM of Aβ1-42 oligomers with or without 200 μg/mL of MABT (B). Results show the mean (±SEM) of two independent assays. Neurotoxicity following extended Aβ1-42 oligomer treatment was tested by morphological analyses (C). Cells as above were treated for 4 days with 10 μM Aβ1-42 oligomers, with or without 50 μg/mL of MABT, and then stained with TuJ1 and DAPI.

FIG. 3 provides graphs and immunocytochemical images corresponding to the experiments described in Example 6.4. Aβ1-42 oligomer binding to neurites was reduced by the anti-Aβ IgG4 monoclonal antibody. Mixed cortical cells from P1 rats were treated with 2 μM of Aβ1-42 oligomers, with or without 100 μg/mL of the MABT or an IgG control for 30 min (shown) or 18 h (not shown). Figures from left to right show: treatment with buffer control, Aβ1-42 oligomers, and Aβ1-42 oligomers with MABT (A). Green indicates staining with TuJ1, red indicates labeling with anti-Aβ (clone 6E10), and blue indicates staining with DAPI. The bottom row shows all three markers whereas the top row shows only Aβ and DAPI. The two insets illustrate the binding of Aβ1-42 oligomers to neurites (left) and the inhibition of this binding by the MABT monoclonal antibody (right). Quantitative measures of fluorescence are shown for 30 min treatment and 18 h treatment (B). Mean results (±SEM) of two experiments are shown. Aβ1-42 tagged with HyLite Fluor-488 verified that MABT inhibited binding of Aβ1-42 to neurites. Cortical cultures from P1 rats were treated as described for (A), except that Aβ1-42 tagged with HyLite Fluor-488 was used (C). Aβ1-42-labeled samples are shown in the upper panel and DAPI-stained samples are shown in the lower panel. One representative experiment is shown. Aβ1-42 fluorescence was quantified, with the mean (±SD) of the two independent experiments shown (D). Intracellular accumulation of Aβ1-42 was assayed by performing an ELISA for Aβ1-42 on trypsin-cleared cells as described in Methods (E). Mean results (±SEM) of three experiments are shown. Upon treatment with MABT, Aβ1 42 oligomers appeared to be taken up by cells resembling microglia, as shown in (F).

FIG. 4 provides graphs and confocal images corresponding to the experiments described in Example 6.5. Aβ1-42 oligomers were taken up via an FcR-mediated mechanism into microglia upon MABT treatment. Confocal imaging was used to show that Aβ1-42 oligomers complexed to MABT are taken up into microglia. Aβ1-42 oligomers are shown in red, and blue is DAPI staining of DNA to show the microglia itself (A). An apical-to-distal slice was obtained from a three-dimensional image rendered from Z-stacks. Confocal imaging was performed on mixed cortical cells labeled for Aβ (red) and stained with DAPI (blue) as described in the Example Section under Materials and Methods. Microglia were identified and scanned for the maximum fluorescence intensity through a series of confocal stacks representing intracellular locations (B), and the total area of fluorescent signal above a minimum threshold was quantified (C). Each mark on the graph represents the total area of Aβ stained within a single cell. A minimum of 20 cells were analyzed for each treatment condition. Data were compared using one-way ANOVA followed by Tukey post-hoc multiple comparison. Means (±SEM) are shown. Microglia (Iba1+) was verified as the cell-type taking up Aβ1-42 complexed to MABT (D). Red is Iba1 staining, green is HyLite Fluor-488-labeled Aβ1 42, and blue is DAPI staining. Aβ1-42 oligomer internalization by different IgG monoclonal antibodies correlates with FcγR-binding. Differential binding to FcγRIIIa-V158 was verified in a binding assay (E). An anti-Aβ monoclonal antibody requires FcγR-binding for full protective effect against Aβ1-42 oligomer toxicity. Mixed cortical cells from P1 rats were treated with Aβ1 42 oligomers, with or without MABT, MABT-IgG1-D265A, MABT-IgG1, or an IgG1 control mAb (F). The graph shows the mean (±SEM) % increase in cell survival compared to Aβ1-42 oligomer treated cells, from 5 independent experiments. Statistical analysis was done using one-way ANOVA followed by Tukey post-hoc multiple comparison.

FIG. 5 provides graphs and immunocytochemical images corresponding to the experiments described in Example 6.6. When complexed to Aβ1-42 oligomers, addition of the IgG1 with a wild-type backbone significantly increased p38 activation over that shown for Aβ1-42 oligomer-treated microglia. Mixed cortical cells from P1 rats were treated with 10 μM Aβ1-42 oligomers for 30 min with or without 100 μg/mL MABT, MABT-IgG1-D265A, or MABT-IgG1 wild-type. An IgG1 monoclonal antibody not binding to Aβ was used as control. The activity of p38MAP K was measured by a phospho-specific ELISA as described in Methods (A). The mean (±SEM) of 4 independent experiments is shown. Statistical analysis was done using one-way ANOVA followed by Tukey post-hoc multiple comparison. Activation of p38MAPK with Aβ1-42 oligomers complexed with monoclonal antibody was specific to microglia (B). Cells were treated as described above and then stained for phospho-p38MAP K (green), with Iba1 (red), and with DAPI (blue). Figures from left to right show; treatment with buffer control, Aβ1-42 oligomers, and Aβ1-42 oligomers with MABT. Pure microglia from CX3CR1-GFP mice were used to verify microglia-specific p38 activity (C). Red indicates staining for phospho-p38 and green is CX3CR1-GFP staining. p38MAP K activity was required for the full protective effect of MABT against Aβ1-42 oligomer toxicity. Mixed cortical cells from P1 rats were treated with 10 μM Aβ1-42 oligomers alone or together with 100 μg/ml MABT or MABT-IgG1-D265A, in the presence or absence of 1 μM SB239063, a p38-specific inhibitor (D). A cytotoxicity assay using the MTT readout was performed after 24 h. The mean (±SEM) of 4 experiments is shown. Statistical analysis was done using one-way ANOVA followed by Tukey post-hoc multiple comparison.

Figure 6:
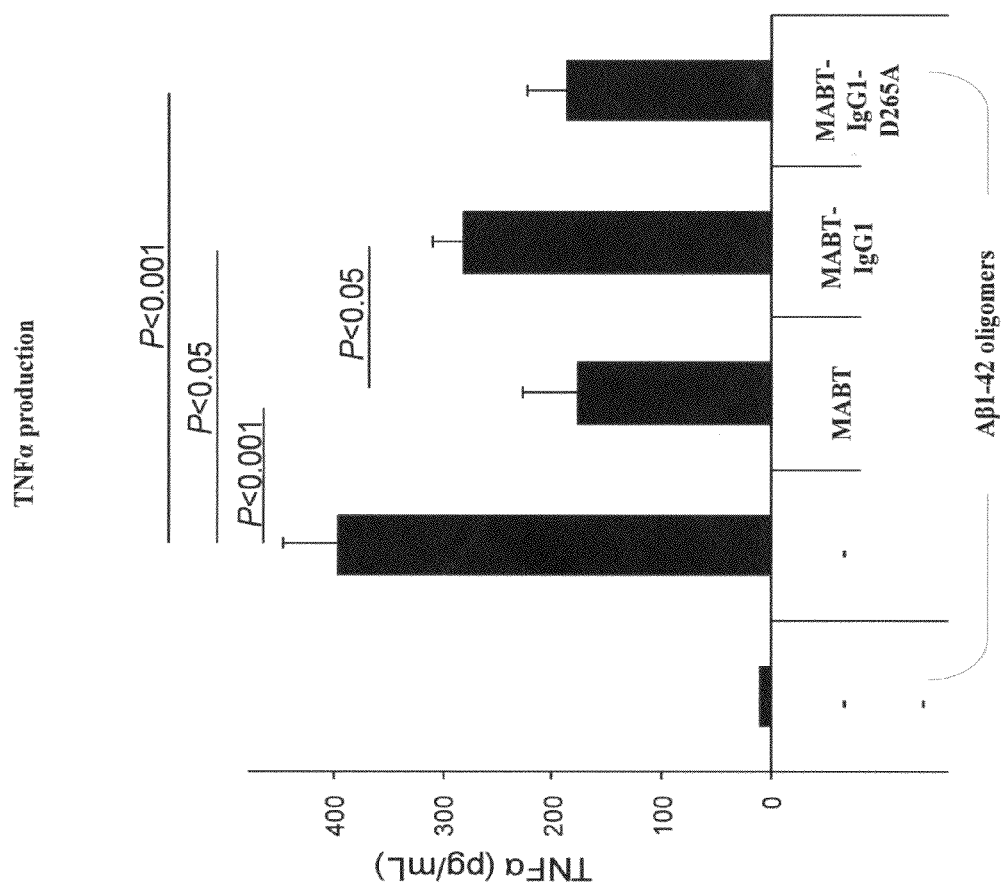

FIG. 6 provides a graph corresponding to the experiments described in Example 6.6. The high affinity of IgG1 to FcγRs makes it less effective in reducing Aβ1-42-mediated pro-inflammatory release by microglia. The release of TNFα by enriched microglia was measured following 24 h of treatment (see Methods). The mean (±SEM) of three independent experiments is shown. Statistical analysis was done using one-way ANOVA followed by Tukey post-hoc multiple comparison.

Figure 7:
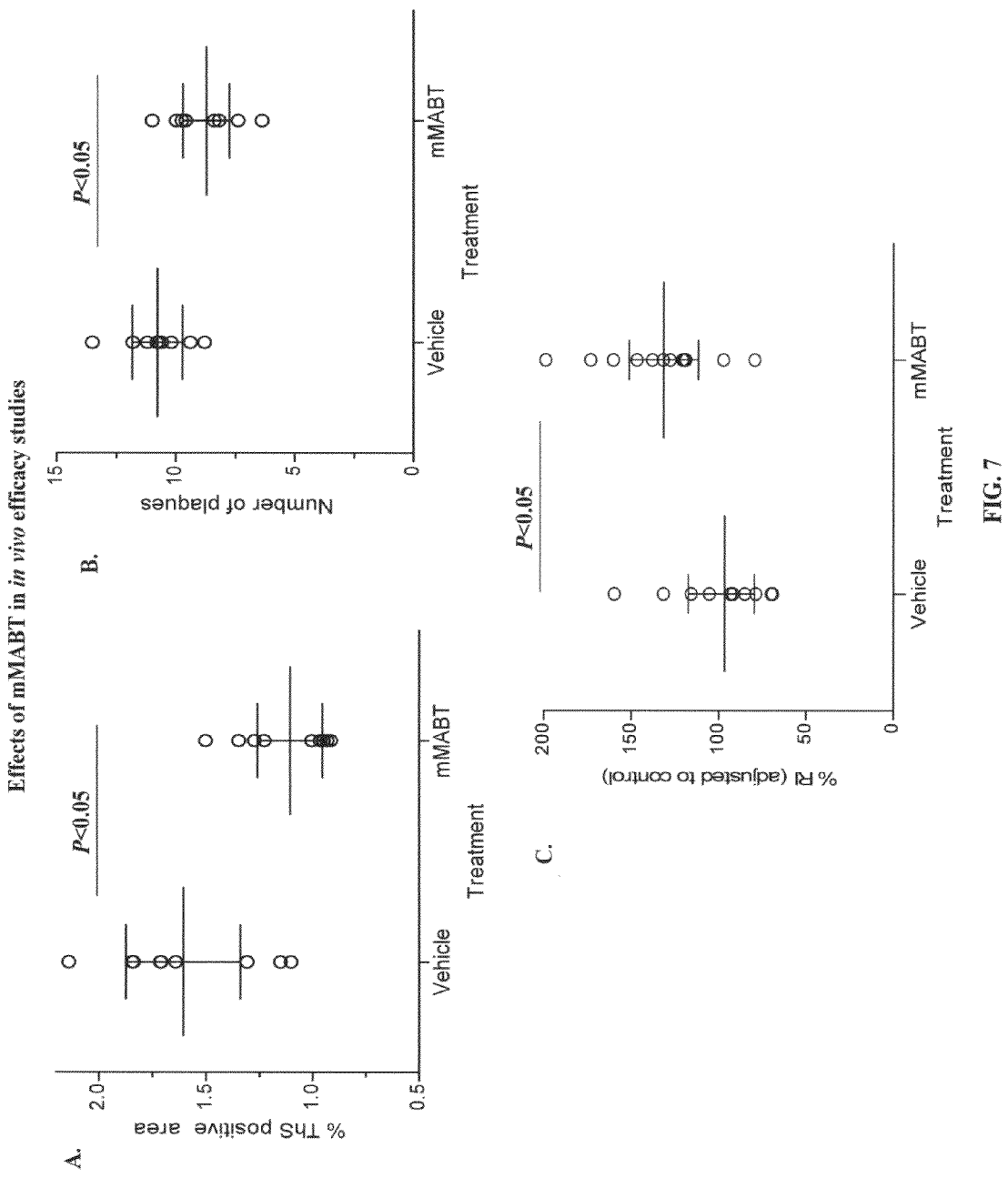

FIG. 7 provides graphs corresponding to the experiments described in Example 6.1. Reduced plaque-loads and improved non-spatial memory in the APP mouse model. Percentage plaque load (A) and mean number of plaques (B) in double APP/PS1 transgenic mice were measured after chronic passive immunization with mMABT, the mouse version of the MABT monoclonal antibody. Animals injected with PBS served as controls (PBS). Thioflavin-S (ThS) was used to stain dense plaques (see Methods). Functionality was demonstrated in single transgenic hAβ P mutant mice following two administrations of mMABT (C). Recognition index (RI), as a measure of recall memory, was studied using the novel object recognition test (see Methods). Animals injected with PBS served as controls (PBS). Each circle on the graph represents an individual mouse. Means (±SD) are shown, *P<0.01.

Figure 8:
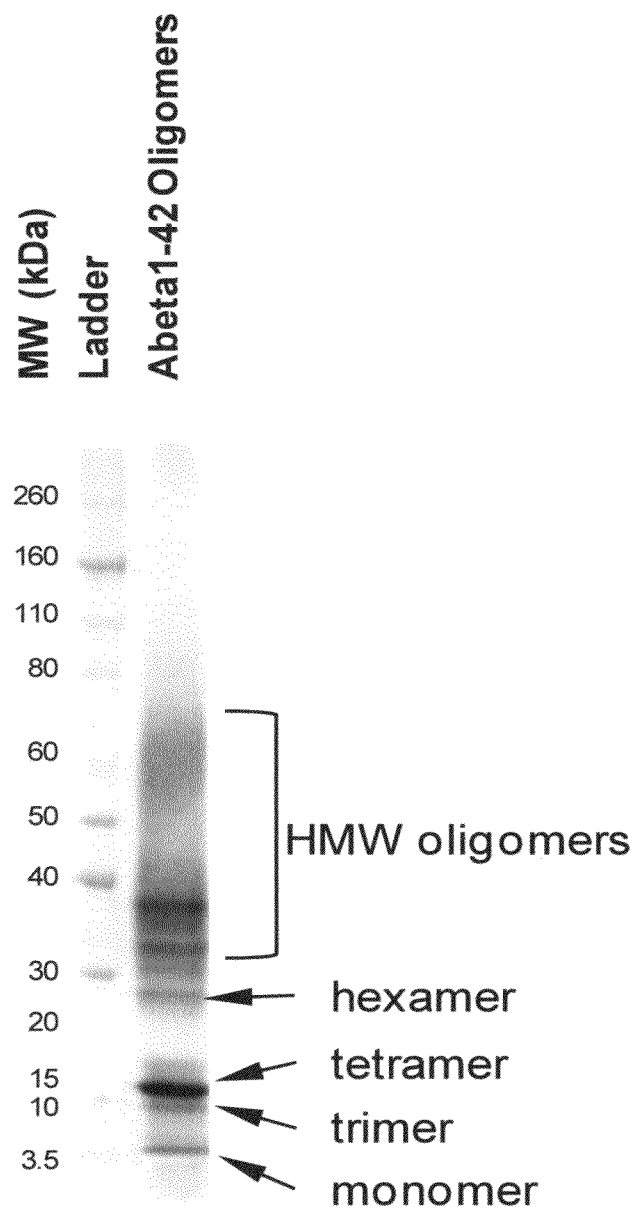

FIG. 8 provides a Western blot corresponding to the experiments described in Example 6.1. Neurotoxic Aβ1-42 is a mixture of low- and high-molecular weight oligomers. Neurotoxic Aβ1-42 oligomers were prepared (see Methods) and used for in vitro experiments assaying the effects of monoclonal antibody treatment on Aβ1-42 oligomer-mediated neurotoxicity. Aβ1-42 oligomers were run on a SDS/PAGE 4-12% gradient gel, transferred to a nitrocellulose membrane, and blotted with an anti-Aβ antibody (clone 6E10).

Figure 9:
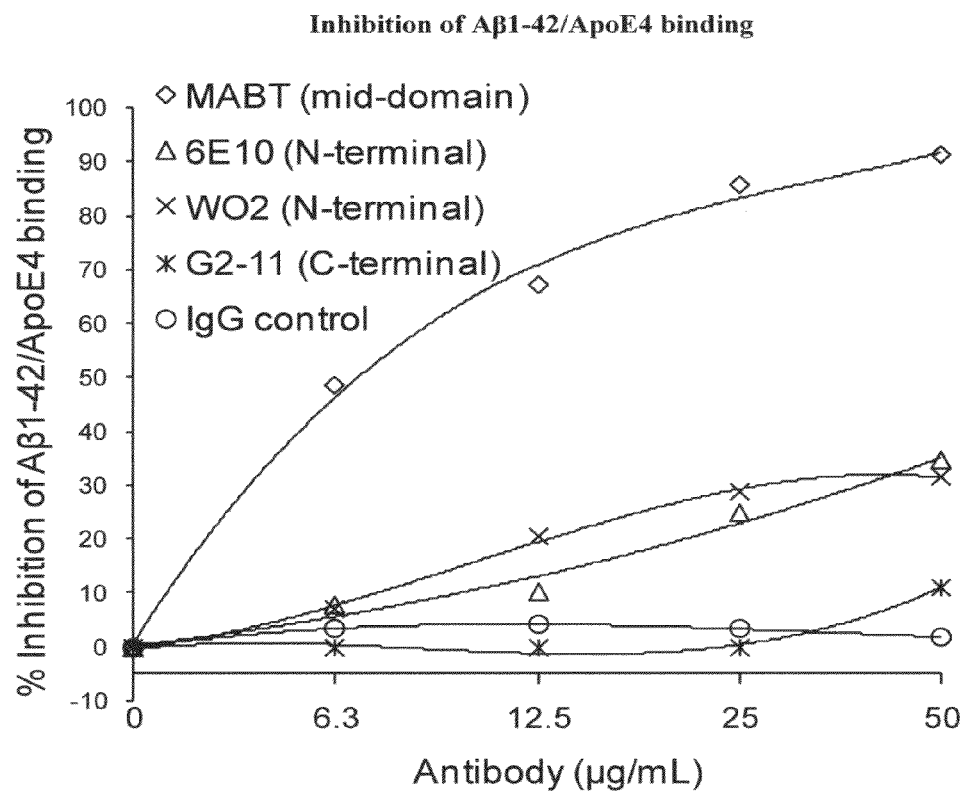

FIG. 9 provides a graph corresponding to the experiments described in Example 6.2. The mid-domain directed MABT inhibits the interaction of Aβ1-42 with ApoE4. An ELISA was used to assess the effect of anti-Aβ N-terminal (clones 6E10 and WO2), C-terminal (clone G2-11), or mid-domain (MABT) monoclonal antibodies on the binding of Aβ1-42 to recombinant human ApoE4. Percent inhibition of signal without an IgG monoclonal antibody is shown.

Figure 10:
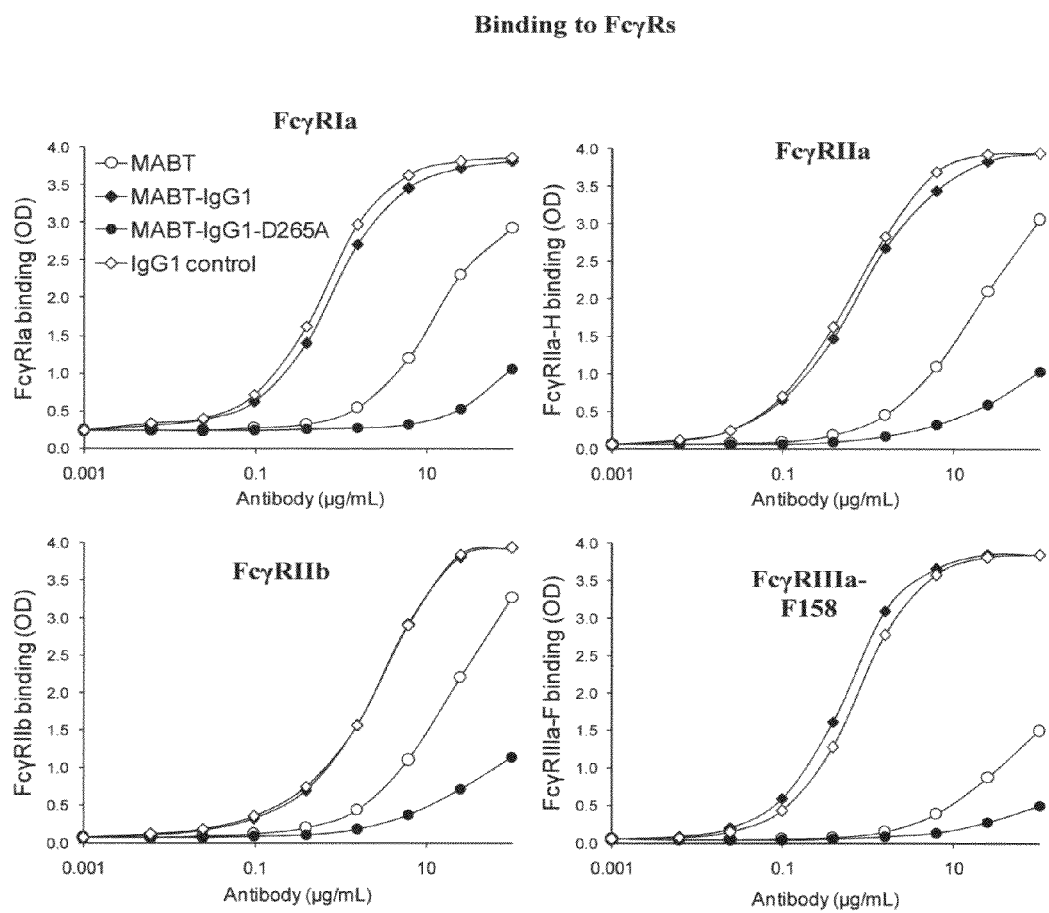

FIG. 10 provides graphs and immunocytochemical images corresponding to the experiments described in Example 6.5. Cross-linked MABT IgG4 monoclonal antibody had reduced binding activity when compared to IgG1 wild-type. Cross-linked anti-Aβ IgG1 wild-type bound to all FcRγ receptors with activities similar to the positive non-Aβ-binding IgG1 control. Both MABT and MABT-IgG1-D265A had substantially reduced binding to all the FcγRs as compared to MABT-Aβ IgG1 and the non-Aβ-binding IgG1 positive control. These findings are consistent with published data for human IgG4 antibodies (Gessner et al., 1998) and IgG1 antibodies carrying the D265A mutation (Shields et al., 2001).

Figure 11:
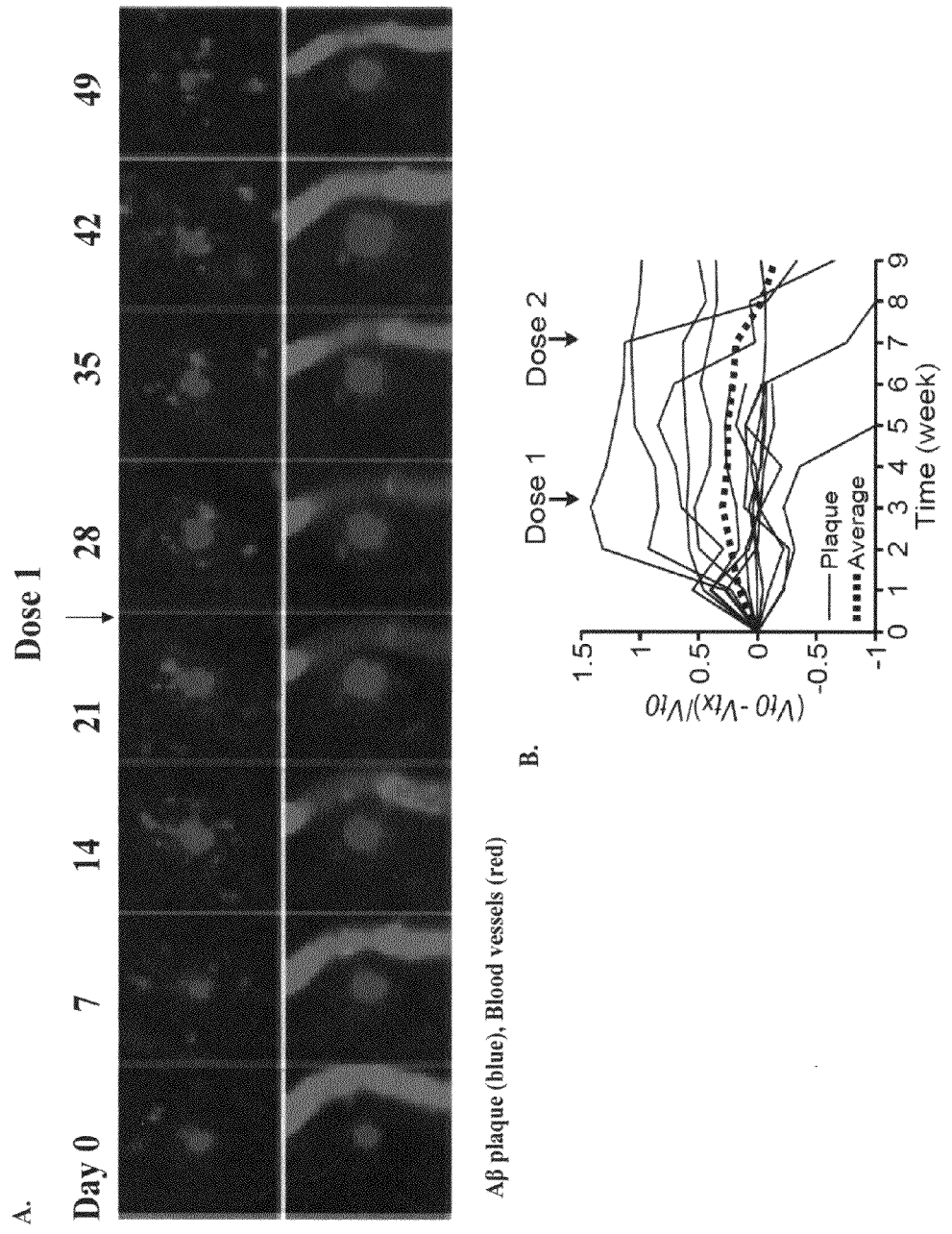

FIG. 11 provides In vivo imaging of Aβ plaques in APP/PS1 mice treated with anti-beta amyloid antibody was performed. Systemic dosing of MABT modulates individual amyloid plaques in vivo. Amyloid plaques in APP/PS1 animals were labeled with Methoxy-X04 injected I.P., visualized by in vivo two-photon microscopy and tracked over multiple weeks (A). The relative change in plaque volume over time plotted as fold-increase from the initial imaging session (B). On average, individual plaque size decreased in volume after systemic dosing with MABT (x plaques, 2 animals).

4.1 DESCRIPTION OF SEQUENCES

SEQ ID NO: 1 Amino acid sequence of MABT humanized heavy chain variable region (CDR1)
SEQ ID NO: 2 Amino acid sequence of MABT humanized heavy chain variable region (CDR2)
SEQ ID NO: 3 Amino acid sequence of MABT humanized heavy chain variable region (CDR3)
SEQ ID NO: 4 Amino acid sequence of MABT humanized light chain variable region (CDR1)
SEQ ID NO: 5 Amino acid sequence of MABT humanized light chain variable region (CDR2)
SEQ ID NO: 6 Amino acid sequence of MABT humanized light chain variable region (CDR3)
SEQ ID NO: 7 Amino acid sequence of MABT humanized light chain variable region
SEQ ID NO: 8 Amino acid sequence of MABT humanized light chain
SEQ ID NO: 9 Amino acid sequence of humanized MABT light chain constant region
SEQ ID NO: 10 Amino acid sequence of MABT humanized heavy chain variable region
SEQ ID NO: 11 Amino acid sequence of MABT humanized heavy chain
SEQ ID NO: 12: Amino acid sequence of IG GAMMA-4 CHAIN C REGION—modified
SEQ ID NO: 13: Nucleotide sequence of CDR2 of MABT humanised heavy chain variable region
SEQ ID NO: 14: Nucleotide sequence of CDR3 of MABT humanised heavy chain variable region
SEQ ID NO: 15: Nucleotide sequence of CDR1 of MABT humanised light chain variable region
SEQ ID NO: 16: Nucleotide sequence of MABT humanized light chain variable region
SEQ ID NO: 17: Nucleotide sequence of MABT humanized light chain
SEQ ID NO: 18: Nucleotide sequence of MABT humanized light chain constant region
SEQ ID NO: 19: Nucleotide sequence of MABT humanized heavy chain variable region
SEQ ID NO: 20: Nucleotide sequence of MABT humanized heavy chain
SEQ ID NO: 21: Nucleotide sequence of MABT humanized heavy chain constant region
SEQ ID NO: 22: Typical amino acid sequence preceding HCDR2
SEQ ID NO: 23 Alternate amino acid sequence of MABT humanized light chain variable region (CDR2)
SEQ ID NO: 24 Alternate amino acid sequence of MABT humanized light chain variable region (CDR2)

5. DETAILED DESCRIPTION

Described below are cell-based assay systems for testing anti-amyloid beta antibodies and methods for monitoring and adjusting treatment of a patient with anti-amyloid beta antibodies. Also described below are cell-based assay systems for testing the safety or efficacy of a neuroprotective agent and methods for monitoring and adjusting treatment of a patient with a neuroprotective agent. Further described below are safe and functional antibodies and methods for using such safe and functional antibodies for the treatment of Alzheimer's disease. Pharmaceutical preparations and modes of administration are also described.

5.1 Cell-Based Assay System

Provided herein are in vitro cell-based assay systems to test the safety and functionality of antibodies, or other agents, for the treatment of an amyloidosis. In certain embodiments, the cells that are affected by the amyloidosis ("target cells"), the amyloid protein in its pathological form, and immune effector cells (e.g., natural killer cells, macrophages, such as microglia cells, neutrophils, and mast cells) are incubated in the presence and absence of the test antibody. Parameters that can be measured to test the safety and functionality of the antibody include survival rate of the target cells, internalization of the amyloid protein into the immune effector cells, and activation of the p38 MAP kinase pathway in the immune effector cells. In certain embodiments, a safe and functional antibody results in maximal internalization and intermediate activation of the p38 MAP kinase pathway.

In more specific embodiments, the amyloidosis is Alzheimer's disease, the amyloid protein is beta amyloid, and the immune effector cells are microglia cells, and the target cells are neurons. In specific embodiments, the cells are obtained from existing cell lines to create a mixed culture. In other embodiments, the mixed cell culture is a primary cortical culture (Meberg & Miller 2003, Methods Cell Biol 71:111-127). In certain embodiments, the mixed cell culture is a primary cortical culture from a rat, mouse, or chimpanzee. In certain embodiments, the primary cortical culture is obtained by cortical biopsy or spinal biopsy from a human patient.

A mixed cell culture that includes neurons and microglia cells is incubated with beta amyloid protein. In one embodiment, the beta amyloid protein is provided as beta amyloid oligomer. The following parameters can be measured in this assay system: (1) the neuronal survival rate can be determined, e.g., by metabolic turnover, which metabolic turnover can be determined, e.g., by mitochondrial oxidation of 3-[4, 5-dimethylthiazol-2-yl]-2,5-diphenyltetrazolium bromide (MTT) or ATP release: (2) beta-amyloid oligomer internalization into microglia can be determined, e.g., by immunocytochemistry against beta amyloid protein or tagging and direct measurement and/or visualization of the beta amyloid protein; and (3) the activation of the p38 MAP K pathway can be determined, e.g., by ELISA against phosphorylated p38MAP K ("Phospho-p38").

In certain embodiments, the neuronal survival rate in the presence of beta amyloid and a safe and functional antibody is increased by at least 10%, 20%, 30%, 40%, 50%, 75%, 100%, 125%, 150%, 175%, 200%, 225%, 250%, 275%, 300%, 325%, 350%, 375%, 400%, 425%, 450%, 475%, or at least 500% as compared to the neuronal survival rate in the absence of the safe and functional antibody.

In certain embodiments, the internalization of beta amyloid into microglia in the presence of a safe and functional antibody is increased by at least 10%, 20%, 30%, 40%, 50%, 75%, 100%, 125%, 150%, 175%, 200%, 225%, 250%, 275%, 300%, 325%, 350%, 375%, 400%, 425%, 450%, 475%, or at least 500% as compared to the internalization rate in the absence of the safe and functional antibody.

In certain embodiments, the p38 MAP kinase activation in microglia in the presence of beta amyloid and a safe and functional antibody is increased by between 5%-15%; 10%-20%; 15%-25%; 20%-30%; 35%-45%; 40%-50%; or 45%-55% as compared to p38 MAP kinase activation in the presence of beta amyloid but the absence of a safe and functional antibody. In a more specific embodiment, the p38 MAP kinase activation in microglia in the presence of beta amyloid and a safe and functional antibody is increased by between 10%-30% as compared to p38 MAP kinase activation in the presence of beta amyloid but the absence of a safe and functional antibody. Further, the p38 MAP kinase activation in microglia in the presence of beta amyloid and a safe and functional antibody is increased by 5%-15%; 10%-20%; 15%-25%; 20%-30%; 35%-45%; 40%-50%; or 45%-55% less than p38 MAP kinase is activated in the presence of an IgG1 isotype anti beta amyloid antibody.

In certain embodiments, a pathological form of beta amyloid, e.g., oligomeric beta amyloid, a test antibody, and microglia cells are incubated to determine safety and functionality of the antibody. The following parameters can be measured in this assay system: (1) beta amyloid oligomer internalization into microglia can be determined, e.g., by immunocytochemistry against beta amyloid protein or tagging of the beta amyloid protein; and (2) the activation of the p38 MAP K pathway can be determined, e.g., by ELISA against Phospho-p38.

To determine p38 MAP kinase activation, any method known to one of ordinary skill in the art can be used. In certain embodiments, ELISA, Western blotting, or immunocytochemistry with an antibody that specifically binds to phosphorylated p38 MAP kinase is used to determine the levels of phosphorylated, i.e., activated, p38 MAP kinase. In certain embodiments, p38 MAP kinase activation is determined by immunocytochemistry using an antibody that specifically binds to p38 MAP kinase to determine the degree of nuclear localization of p38 MAP kinase. The higher the degree of nuclear localization of p38 MAP kinase, the higher the level of p38 MAP kinase activation.

In certain embodiments, the activation of other components in the p38 MAP kinase signaling pathway can be measured. In certain embodiments, expression levels of a downstream target of p38 MAP kinase can be measured to determine the p38 MAP kinase activation in the patient. Such downstream targets include, but are not limited to, 90-kDa ribosomal S6 kinase (pp90rsk); (RSK) family: RSK1, RSK2, MNK1/2 and MSK1/2; and nuclear translation factors such as Elk-1, ATF2, STAT3 and CREB. Expression levels of downstream targets can be determined by any method known to one of ordinary skill in the art, such as, but not limited to, Northern blotting, Western blotting, or polymerase chain reaction.

5.2 Monitoring and Adjustment of Treatment

In certain embodiments, p38 MAP kinase activation is monitored in immune effector cells, such as microglia cells, of a patient who is being treated with a safe and functional antibody that specifically binds to an amyloid protein, such as beta amyloid. Immune effector cells can be obtained from a patient by any method known to one of ordinary skill in the art. In specific embodiments, microglia cells are obtained by cortical biopsy or spinal biopsy. Immune effector cells can be maintained in culture by any method known to one of ordinary skill in the art.

In certain embodiments, p38 MAP kinase activation is monitored in immune effector cells, such as microglia cells, of a patient who is being treated with an agent, such as a neuroprotective agent. In certain, more specific embodiments, the patient is being treated for an amyloidosis, such as Alzheimer's Disease. In certain, even more specific embodiments, the patient is being treated with tacrine (COGNEX, Morris Plains, N.J.), donepezil (ARICEPT, Tokyo, JP), rivastigmine (EXELON, East Hanover, N.J.), galantamine (REMINYL, New Brunswick, N.J.), or memantine (NAMENDA, New York, N.Y.).

In certain embodiments, the administration dosage and/or administration regimen is adjusted for the patient such that p38 MAP kinase activation in microglia cells is at intermediate levels, i.e., higher than in the absence of the antibody but lower than in the presence of an IgG1 antibody that specifically binds beta amyloid in the presence of an beta amyloid oligomer. If p38 MAP kinase activation is above intermediate levels, the dosage is reduced and/or the administration frequency is reduced. If p38 MAP kinase activation is below intermediate levels, the dosage is increased and/or the administration frequency is increased.

In certain embodiments, a modulator of the p38 MAP kinase signaling pathway is co-administered with the safe and functional antibody to adjust p38 MAP kinase activation to intermediate levels. If p38 MAP kinase activation is above intermediate levels, an inhibitor of p38 MAP kinase signaling pathway can be co-administered. If p38 MAP kinase activation is below intermediate levels, an activator of p38 MAP kinase signaling pathway can be co-administered.

Illustrative inhibitors of the p38 MAP kinase signaling pathway include 4-[4-(4-Fluorophenyl)-5-(4-pyridinyl)-1H-imidazol-2-yl]phenol ("SB 202190"); 4-[5-(4-Fluorophenyl)-2-[4-(methylsulfonyl)phenyl]-1H-imidazol-4-yl]pyridine ("SB 203580"); and trans-4-[4-(4-Fluorophenyl)-5-(2-methoxy-4-pyrimidinyl)-1H-imidazol-1-yl]cyclohexanol ("SB 239063") and pharmaceutically suitable derivatives thereof.

Illustrative activators of the p38 MAP kinase signaling pathway include Anisomycin, MKK, Rac, Cdc42 and PAK1, IL-1, IL-1-receptor, TNF, LPS, TRAF6, and TAB1/2.

In certain embodiments, p38 MAP kinase intermediate activation levels are between 5%-15%; 10%-20%; 15%-25%; 20%-30%; 35%-45%; 40%-50%; or 45%-55% above p38 MAP kinase activation in microglia cells of the patient in the absence of the safe and functional antibody.

To determine p38 MAP kinase activation, any method known to one of ordinary skill in the art can be used. In certain embodiments, ELISA, Western blotting, or immunocytochemistry with an antibody that specifically binds to phosphorylated p38 MAP kinase is used to determine the levels of phosphorylated, i.e., activated, p38 MAP kinase. In certain embodiments, p38 MAP kinase activation is determined by immunocytochemistry using an antibody that specifically binds to p38 MAP kinase to determine the degree of nuclear localization of p38 MAP kinase. The higher the degree of nuclear localization of p38 MAP kinase, the higher the level of p38 MAP kinase activation.

In certain embodiments, the activation of other components in the p38 MAP kinase signaling pathway can be measured.

In certain embodiments, expression levels of a downstream target of p38 MAP kinase can be measured to determine the p38 MAP kinase activation in the patient. Such downstream targets include, but are not limited to, 90-kDa ribosomal S6 kinase (pp90rsk); (RSK) family: RSK1, RSK2, MNK1/2 and MSK1/2; and nuclear translation factors such as Elk-1, ATF2, STAT3 and CREB. Expression levels of downstream targets can be determined by any method known to one of ordinary skill in the art, such as, but not limited to, Northern blotting, Western blotting, or detection of gene transcripts by, e.g., RT-PCR.

Further, provided herein is a method for evaluating safety and functionality of an anti beta-amyloid antibody for the treatment of Alzheimer's disease in a patient. In certain embodiments, microglia cells can be obtained from the patient. In a specific embodiment, microglia cells can be obtained from the patient before treatment of the patient with the anti beta-amyloid antibody has begun. The microglia cells from the patient can be maintained in cell culture using standard art-known techniques.

In certain embodiments, the microglia cells from the patient are incubated with the anti beta-amyloid antibody and beta-amyloid oligomers. The following parameters can be determined: binding of the antibody—beta amyloid complex to the microglia cells; internalization of the antibody—beta amyloid complex into the microglia cells; and/or p38 MAP kinase activation in the microglia cells.

Controls can be performed by incubating the microglia cells from the patient with the anti beta-amyloid antibody alone (i.e., without beta-amyloid oligomer); and/or with beta-amyloid oligomers alone (i.e., without the antibody); and/or with an IgG1 anti beta-amyloid antibody in the presence of beta-amyloid oligomer. In certain embodiments, an anti beta-amyloid antibody is safe and functional if p38 MAP kinase activation is between 5%-15%; 10%-20%; 15%-25%; 20%-30%; 35%-45%; 40%-50%; or 45%-55% above p38 MAP kinase activation in control microglia cells of the patient in the presence of beta-amyloid oligomer but the absence of the safe and functional antibody. In certain embodiments, an anti beta-amyloid antibody is safe and functional if beta-amyloid internalization into microglia cells is between 5%-15%; 10%-20%; 15%-25%; 20%-30%; 35%-45%; 40%-50%; or 45%-55% above or below that of monoclonal antibody MABT (see Section 6).

5.3 Sate and Functional Antibodies

In certain embodiments, the constant region of an antibody that specifically binds the amyloid protein of the amyloidosis to be treated can be modified or replaced to provide a safe and functional antibody. In certain embodiments, the constant region of the resulting antibody binds with intermediate activity to the Fc receptor on the surface of immune effector cells such as natural killer cells, macrophages, neutrophils, and mast cells. In certain embodiments, the resulting antibody activates the p38 MAP K pathway in the immune effector cell at intermediate levels, i.e., above p38 MAP kinase activation in the absence of the antibody but below p38 MAP kinase activation in the presence of the same concentration of an IgG1 antibody with the same binding specificity. In certain embodiments the variable regions outside the complementarity determining regions ("CDR") can also be modified to provide a safe and functional antibody. Also provided herein are methods for generating such an antibody and pharmaceutical compositions comprising such an antibody.

Antigen binding specificity is provided by the complementarity determining regions ("CDR") that are embedded in the variable regions of an antibody's light chain and heavy chain, respectively. Antibody constant regions and the framework regions that surround the CDRs that can be used for the construction of the safe and functional antibodies provided herein include those described in Section 5.3.1. In certain embodiments, CDRs or variable regions that can be used for the construction of the safe and functional antibodies can be derived from the antibodies set forth in Table 2.

In certain embodiments, the CDRs of a known antibody that specifically binds human beta amyloid (see Table 2 below) are combined with the constant region of a human IgG4 and the framework regions between the CDRs of the antibody are replaced with the framework regions of a human IgG, such as IgG1, IgG2, IgG3, or IgG4. In certain embodiments, the variable regions of a known humanized anti-beta amyloid antibody, e.g., Bapineuzumab or Solanezumab, are combined with the constant region of a human IgG4.

5.3.1 Constant Regions

Antibody constant regions for the generation of the safe and functional antibodies provided herein can be derived from any isotype, including IgA, IgD, IgE, IgG and IgM. In certain embodiments, antibody constant regions for the generation of the safe and functional antibodies provided herein can be derived from subtype IgA1, IgA2, IgG1, IgG2, IgG3, and IgG4.

Similarly, framework regions of antibody heavy chain regions for the generation of the safe and functional antibodies provided herein can be derived from any isotype, including IgA, IgD, IgE, IgG and IgM. In certain embodiments, antibody framework regions for the generation of the safe and functional antibodies provided herein can be derived from subtype IgA1, IgA2, IgG1, IgG2, IgG3, and IgG4.

In a specific embodiment, the constant region for the generation of a safe and functional antibody provided herein can be derived from isotype IgG. In an even more specific embodiment, the constant region for the generation of a safe and functional antibody provided herein can be derived from isotype IgG4.

In a specific embodiment, the framework regions for the generation of a safe and functional antibody provided herein can be derived from isotype IgG. In an even more specific embodiment, the framework regions for the generation of a safe and functional antibody provided herein can be derived from isotype IgG4.

In certain embodiments, the constant region of the heavy chain of a safe and functional antibody is a chimeric constant region from different isotypes or subtypes. In a specific embodiment, the constant region of the heavy chain is a chimera between that portion of the IgG4 heavy chain constant region that is responsible for the effector function of IgG4 and a different subtype of IgG. In a specific embodiment, the constant region of the heavy chain is a chimera between the CH2 domain of a human IgG4 heavy chain constant region and a different subtype of IgG.

In certain embodiments, the chimeric constant region has an intermediate binding activity to Fcγ as described below. In certain embodiments, the chimeric constant region mediates the internalization into immune effector cells, such as microglia, such that p38 MAP kinase pathway activity is at an intermediate level as determined by a cell-based assay system described in Section 5.1.

In certain embodiments, a constant region is optimized by introducing mutations. Mutations can be introduced into the constant region using recombinant DNA technology. In certain embodiments, the resulting antibodies promote internalization of beta amyloid into microglia cells at high levels while activation of the p38 MAP kinase pathway is at intermediate levels. Rate of internalization and p38 MAP kinase activation can be determined using the cell-based assay system described in Section 5.1. In certain embodiments, the antibody with mutated constant region has an intermediate binding activity to an Fc receptor as described below.

In certain embodiments, a constant region is optimized by altering the glycosylation pattern. The glycosylation pattern can be altered by virtue of the expression system where the antibody is synthesized and/or mutating the amino acid that is being glycosylated (e.g., Asn297). In certain embodiments, the resulting antibodies promote internalization of beta amyloid into microglia cells at high levels while activation of the p38 MAP kinase pathway is at intermediate levels. Rate of internalization and p38 MAP kinase activation can be determined using the cell-based assay system described in Section 5.1. In certain embodiments, the antibody with constant region with altered glycosylation pattern has an intermediate binding activity to an Fc receptor as described below.

In certain embodiments, the constant region has an intermediate binding activity to its Fc receptor. Set forth in Table 1 are illustrative Fc receptors and their respective principal antibody ligand. Binding activity, between antibody ligand and Fc receptor can be determined using any method known to one of ordinary skill in the art. Exemplary methods of measuring binding affinity include but are not limited to ELISA assays and BIACORE analysis. In certain, more specific embodiments, the Fc receptor is an Fc receptor that mediates internalization of the antibody antigen complex into an immune effector cell. In certain, even more specific embodiments, the Fc receptor is an Fcγ receptor that is expressed on microglia cells.

TABLE 1

Illustrative isotypes or subtypes of antibodies and their respective Fc receptor

| Receptor Name | Principal Antibody Ligand |
|---|---|
| FcγRI (CD64) | IgG1 and IgG3 |
| FcγRIIA (CD32) | IgG |
| FcγRIIB1 (CD32) | IgG |
| FcγRIIB2 (CD32) | IgG |
| FcγRIIIA (CD16a) | IgG |
| FcγRIIIB (CD16b) | IgG |
| FceRI | IgE |
| FceRII (CD23) | IgE |
| FcαRI (CD89) | IgA |
| FcαRI/nR | IgA and IgM |
| FcRn | IgG |

In certain embodiments, the antibody constant region is of the isotype IgG and the Fc receptor is an Fcγ receptor. The constant region for generation of a safe and functional antibody has a binding activity to the Fcγ receptor that is between 10% and 30%; between 20% and 40%, between 30% and 50%, between 40% and 60%, between 50% and 70%, between 60% and 80%, or between 70% and 90% of the binding activity of IgG1 to the Fcγ receptor. In a specific embodiment, the constant region for the generation of a safe and functional antibody for the treatment of Alzheimer's disease is between 15% and 25%, or more specifically about 20%, of the binding activity of IgG1 to Fcγ.

In certain embodiments, the effector region of the anti-Aβ antibody is modified such that the effector function of the antibody is reduced or eliminated. The modification can be any genetic alteration resulting in an amino acid substitution and/or deletion. In more specific embodiments, the constant region is a modified IgG1 constant region with reduced or eliminated effector function. Such modifications can be introduced as described, e.g., in international patent application publication no. WO 00/42072 published on Jul. 20, 2000, which is incorporated herein in its entirety. In certain embodiments, the ability of the antibody with the modified constant region to bind to its Fc receptor is reduced relative to the unmodified constant region. In other embodiments, the binding between the constant region and its Fc receptor is not altered but effector functions such as cytotoxicity in the presence of effector cells, are reduced relative to the unmodified constant region.

5.3.2 Variable Regions

In certain embodiments, the variable regions of an antibody known to bind specifically to beta amyloid and/or its pathological form(s) can be used for the generation of a safe and functional antibody. In certain more specific embodiments, the variable regions of a humanized antibody known to bind specifically to beta amyloid and/or its pathological form(s) can be used for the generation of a safe and functional antibody. In certain embodiments, the variable regions are obtained from a non-IgG4 humanized antibody. In a specific embodiment, the variable regions are obtained from a non-IgG4 humanized antibody and an IgG4 constant region is used as constant region.

CDRs of antibodies known to bind to an amyloid protein of interest can be used for the generation of a safe and functional antibody useful in the methods described herein. In certain embodiments, CDRs of an antibody known to bind specifically to beta amyloid and/or its pathological form(s) can be used for the generation of such a safe and functional antibody.

Illustrative antibodies whose CDRs or variable regions can be used include, but are not limited to those set forth in Table 2.

TABLE 2

Illustrative anti-beta amyloid antibodies

| Antibody | Reference/Source |
|---|---|
| mACI-01-Ab7 | WO 2007/068412 published Jun. 21, 2007 |
| mACI-01-Ab7 | WO 2008/060364 published May 22, 2008 |
| mACI-02-Ab6 | WO 2007/068412 published Jun. 21, 2007 |
| mACI-11-Ab9 | WO 2007/068412 published Jun. 21, 2007 |
| mACI-12-Ab11 | WO 2007/068412 published Jun. 21, 2007 |
| mACI-24-Ab4 | WO 2007/068412 published Jun. 21, 2007 |
| ACI-24-Ab-3 | WO 2008/156621 published Dec. 24, 2008 |
| ACI-11-Ab-9 | WO 2008/156621 published Dec. 24, 2008 |
| ACI-12-Ab-11 | WO 2008/156621 published Dec. 24, 2008 |
| 20C2 | WO 2007/050359 published May 3, 2007 |
| 8F5 | WO 2007/064972 published Jun. 7, 2007 |
| 8C5 | WO 2007/064972 published Jun. 7, 2007 |
| 6E10 | Pirttilä et al. 1994, J Neurol Sci 127: 90-95 |
| 4G8 | Pirttilä et al. 1994, J Neurol Sci 127: 90-95 |
| MS-Roche#3 and MS-Roche#3 derived antibodies | WO 03/070760 published Aug. 28, 2003 |
| MS-Roche#7 and MS-Roche#7 derived antibodies | WO 03/070760 published Aug. 28, 2003 |
| MS-Roche#8 and MS-Roche#8 derived antibodies | WO 03/070760 published Aug. 28, 2003 |
| 3D6 | WO 02/46237 published Jun. 13, 2002 |
| 10D5 | WO 02/46237 published Jun. 13, 2002 |
| 12B4 | WO 2006/066171 published Jun. 22, 2006 |
| 12A11 | WO 2006/066171 published Jun. 22, 2006 |
| 6C6 | WO 2006/066171 published Jun. 22, 2006; Frenkel et al. 1999, J Neuroimmun 95: 136-142 |
| 9G8 | WO 2006/066171 published Jun. 22, 2006 |
| 1C2 | WO 2006/066171 published Jun. 22, 2006 |
| 2B1 | WO 2006/066171 published Jun. 22, 2006 |
| 3A3 | Bard et al. 2003, PNAS 100: 2023-2028 |
| 266 | US 2004/0043418 published Mar. 4, 2004 |
| 6H9 | WO 2006/066171 published Jun. 22, 2006 (FIG. 17 & 18) |
| 15C11 | WO 2006/066171 published Jun. 22, 2006 |
| 9G8 | WO 2006/066171 published Jun. 22, 2006 (FIG. 17 & 18) |
| 2H3 | Frenkel et al. 1999, J Neuroimmun 95: 136-142 |
| Fv1E1 | EP 1 741 783 A1 published Oct. 1, 2007 |
| Fv1E4 | EP 1 741 783 A1 published Oct. 1, 2007 |
| Fv1E7 | EP 1 741 783 A1 published Oct. 1, 2007 |
| Fv2A7 | EP 1 741 783 A1 published Oct. 1, 2007 |
| Fv2A8 | EP 1 741 783 A1 published Oct. 1, 2007 |
| Fv2B6 | EP 1 741 783 A1 published Oct. 1, 2007 |
| F10 | EP 1 741 783 A1 published Oct. 1, 2007 |
| B7 | EP 1 741 783 A1 published Oct. 1, 2007 |
| B6 | EP 1 741 783 A1 published Oct. 1, 2007 |
| D1 | EP 1 741 783 A1 published Oct. 1, 2007 |
| VLA2 | EP 1 741 783 A1 published Oct. 1, 2007 |
| H1v2 (scFv) | Liu et al. 2004, Biochemistry 43: 6959-6967 |

TABLE 2-continued

Illustrative anti-beta amyloid antibodies

| Antibody | Reference/Source |
| --- | --- |
| scFv59 (scFv) | Fukuchi et al. 2006, Biochem and Biophys Res Comm 344: 79-86 |
| R7CN | US 2003/0108551 published Jun. 12, 2003 |
| 6F/3D | Accurate Chemicals |
| AMY-33 | Zymed |
| IgM 508 | Frenkel et al. 2000, J Neuroimmunol 106: 23-31 |
| NU-1 | Lambert et al. 2007, J Neurochem 100: 23-35 |
| NU-2 | Lambert et al. 2007, J Neurochem 100: 23-35 |
| NU-4 | Lambert et al. 2007, J Neurochem 100: 23-35 |
| NU-6 | Lambert et al. 2007, J Neurochem 100: 23-35 |
| 2A10 | WO 2006/055178 published May 26, 2006 |
| 2B4 | WO 2006/055178 published May 26, 2006 |
| 2D6 | WO 2006/055178 published May 26, 2006 |
| 4C2 | WO 2006/055178 published May 26, 2006 |
| 4E2 | WO 2006/055178 published May 26, 2006 |
| 5F10 | WO 2006/055178 published May 26, 2006 |
| 5G12 | WO 2006/055178 published May 26, 2006 |
| 6B7 | WO 2006/055178 published May 26, 2006 |
| 6B11 | WO 2006/055178 published May 26, 2006 |
| 11B4 | WO 2006/055178 published May 26, 2006 |
| 11B5 | WO 2006/055178 published May 26, 2006 |
| 14A11 | WO 2006/055178 published May 26, 2006 |
| 15G6 | WO 2006/055178 published May 26, 2006 |
| 17G4 | WO 2006/055178 published May 26, 2006 |
| 3B7 | WO 2006/055178 published May 26, 2006 |
| 2H4 | WO 2006/055178 published May 26, 2006 |
| 3B3 | WO 2006/055178 published May 26, 2006 |
| 1F6 | WO 2006/055178 published May 26, 2006 |
| 1F4 | WO 2006/055178 published May 26, 2006 |
| 2E12 | WO 2006/055178 published May 26, 2006 |
| 26D6 | WO 2006/055178 published May 26, 2006 |
| 9TL and variants | WO 2008/110885 published Sep. 18, 2008 |
| 6G and variants | WO 2008/110885 published Sep. 18, 2008 |
| 5F7 | WO 2007/062852 published Jun. 7, 2007 |
| 10F11 | WO 2007/062852 published Jun. 7, 2007 |
| 7C6 | WO 2007/062852 published Jun. 7, 2007 |
| 4B7 | WO 2007/062852 published Jun. 7, 2007 |
| 2F2 | WO 2007/062852 published Jun. 7, 2007 |
| 6A2 | WO 2007/062852 published Jun. 7, 2007 |
| 4D10 | WO 2007/062852 published Jun. 7, 2007 |
| 7E5 | WO 2007/062852 published Jun. 7, 2007 |
| 10C1 | WO 2007/062852 published Jun. 7, 2007 |
| 3B10 | WO 2007/062852 published Jun. 7, 2007 |
| 10F4 | WO 2008/067464 published Jun. 5, 2008 |
| 3C5 | WO 2008/067464 published Jun. 5, 2008 |
| BAM10 | santa cruz biotechnology, inc. |
| 6G12 | santa cruz biotechnology, inc. |
| 20-1 | santa cruz biotechnology, inc. |
| 2B9 | santa cruz biotechnology, inc. |
| 2C8 | santa cruz biotechnology, inc. |
| 6A6 | santa cruz biotechnology, inc. |
| B-4 | santa cruz biotechnology, inc. |
| DE2B4 | santa cruz biotechnology, inc. |
| LN27 | santa cruz biotechnology, inc. |
| NAB228 | santa cruz biotechnology, inc. |
| 1304.1 | santa cruz biotechnology, inc. |
| 5C3 | santa cruz biotechnology, inc. |
| BDI350 | santa cruz biotechnology, inc. |
| KPI4.1 | santa cruz biotechnology, inc. |
| 11H3 | santa cruz biotechnology, inc. |
| 9F1 | santa cruz biotechnology, inc. |
| 19H11 | santa cruz biotechnology, inc. |
| 1B11F3 | santa cruz biotechnology, inc. |
| 310-03 | santa cruz biotechnology, inc. |
| 79010Y | santa cruz biotechnology, inc. |
| 16E9 | santa cruz biotechnology, inc. |
| 19B8 | santa cruz biotechnology, inc. |
| 3G5 | santa cruz biotechnology, inc. |
| Mcl | santa cruz biotechnology, inc. |
| 9C4 | santa cruz biotechnology, inc. |
| 3H2 | santa cruz biotechnology, inc. |
| 6E10 | santa cruz biotechnology, inc. |
| 4H309 | santa cruz biotechnology, inc. |
| 3H530 | santa cruz biotechnology, inc. |

In a specific embodiment, the CDRs of a safe and functional antibody of the invention are as follows: CDR1 of the heavy chain has the amino acid sequence of SEQ ID NO:1; CDR2 of the heavy chain has the amino acid sequence of SEQ ID NO:2; CDR3 of the heavy chain has the amino acid sequence of SEQ ID NO:3; CDR1 of the light chain has the amino acid sequence of SEQ ID NO:4; CDR2 of the light chain has the amino acid sequence of SEQ ID NO:5; and CDR3 of the light chain has the amino acid sequence of SEQ ID NO:6.

In another specific embodiment, the heavy chain variable region of a safe and functional antibody of the invention has an amino acid sequence that is at least 90%, 91%, 92%, 93%, 94%, 95%, 96%, 97%, 98%, or at least 99% identical to the amino acid sequence of SEQ ID NO:7. In a more specific embodiment, the heavy chain variable region of a safe and functional antibody of the invention has an amino acid sequence that is 100% identical to the amino acid sequence of SEQ ID NO:7.

In another specific embodiment, the light chain variable region of a safe and functional antibody of the invention has an amino acid sequence that is at least 90%, 91%, 92%, 93%, 94%, 95%, 96%, 97%, 98%, or at least 99% identical to the amino acid sequence of SEQ ID NO:10. In a more specific embodiment, the light chain variable region of a safe and functional antibody of the invention has an amino acid sequence that is 100% identical to the amino acid sequence of SEQ ID NO:10.

In an even more specific embodiment, the heavy chain variable region of a safe and functional antibody of the invention has an amino acid sequence that is at least 90%, 91%, 92%, 93%, 94%, 95%, 96%, 97%, 98%, or at least 99% identical to the amino acid sequence of SEQ ID NO:7 and the light chain variable region of the safe and functional antibody of the invention has an amino acid sequence that is at least 90%, 91%, 92%, 93%, 94%, 95%, 96%, 97%, 98%, or at least 99% identical to the amino acid sequence of SEQ ID NO:10.

In one embodiment, the heavy chain variable region of a safe and functional antibody of the invention has an amino acid sequence that is at 100% identical to the amino acid sequence of SEQ ID NO:7 and the light chain variable region of a safe and functional antibody of the invention has an amino acid sequence that is 100% identical to the amino acid sequence of SEQ ID NO:10.

The CDRL2 sequence ("KVSNRFS" (SEQ ID NO: 5)) of the mMABT antibody may be modified slightly without adversely affecting antibody activity. Conservative substitutions may be made through exchange of R for K at position 50 and S for N at position 53. The two alternative CDRL2 sequences are therefore "RVSNRFS" (SEQ ID NO: 23) and "KVSSRFS" (SEQ ID NO: 24), respectively. These are incorporated into the murine VK sequence with no other changes, as mMABT VK-R and mMABT VK-S, respectively.

5.3.3 Construction of Antibodies

In certain embodiments, the CDRs of an antibody that binds specifically to an amyloid protein or its pathological form, such as beta amyloid, are placed into an antibody with constant regions consistent with a safe and functional antibody of the invention (Section 5.3.1). In certain embodiments, the variable regions of an antibody that binds specifically to an amyloid protein or its pathological form, such as beta amyloid, are combined with constant regions consistent with a safe and functional antibody of the invention (Section 5.3.1).

Methods for constructing humanized antibodies are well-known in the art. For example, methods for generating humanized antibodies are described in International Patent Application No. PCT/US2007/073504 published as WO2008/011348, which is incorporated herein by reference in its entirety.

5.3.4 Tests for Safety

Side effects observed during treatment of Alzheimer's disease with anti-beta amyloid antibodies include inflammatory side effects, such as meningitis and meningoencephalitis, and fluid build up in the brain (cerebral edema). Other side effects include adverse immune reaction, i.e., an immune reaction by the patient against the administered anti-beta amyloid antibody.

5.3.4.1 Adverse Immune Reaction

One side effect that can be monitored in a patient that has received an anti-beta amyloid antibody is an antibody response to the antibody. Any technique known to one of ordinary skill in the art to detect, monitor, or quantify the extent of such an adverse immune reaction can be used. Such an antibody response occurs when an antibody binds the anti-beta amyloid antibody. When soluble antigens combine with antibodies in the vascular compartment, they may form circulating immune complexes that are trapped nonspecifically in the vascular beds of various organs, causing so-called immune complex diseases, such as serum sickness, vasculitis, nephritis systemic lupus erythematosus with vasculitis or glomerulonephritis.

Immune complex disease can be detected and/or monitored using any method known in the art. For example, an immune complex test can be used to demonstrate circulating immune complexes in the blood, to estimate the severity of immune complex disease. An immune complex test can be performed by any method known to one of skill in the art. In particular, an immune complex test can be performed using any one or more of the methods described in U.S. Pat. No. 4,141,965, U.S. Pat. No. 4,210,622, U.S. Pat. No. 4,210,622, U.S. Pat. No. 4,331,649, U.S. Pat. No. 4,544,640, U.S. Pat. No. 4,753,893, and U.S. Pat. No. 5,888,834, each of which is incorporated herein by reference in its entirety.

Another method is use of an immunoassay, such as an enzyme-linked immunosorbent assay (ELISA), to detect anti-idiotypic antibodies against the antibody. See, Gerostamoulos, J. et. al. (2001). The Use Of Elisa (Enzyme-Linked Immunosorbent Assay) Screening In Postmortem Blood. TIAFT, The International Association of Forensic Toxicologists; Clarke, W. and Dufour, D. R., Editors (2006). Contemporary Practice in Clinical Chemistry, AACC Press, Washington, D.C. Harris, N. and Winter, W; Presta U.S. Pat. No. 6,737,056; Harlow and Lane, Antibodies: A Laboratory Manual (Cold Spring Harbor Laboratory, New York 1988 555-612); WO96/13590; and WO96/29605.

5.3.4.2 Edema

One side effect that can be monitored in a patient that has received an anti-beta amyloid antibody is edema, in particular, cerebral edema, which may be assessed, e.g., by MRI scan, DCE-MRI scan, PET scan, and/or CT scan. Any technique known to one of ordinary skill in the art to detect, monitor, or quantify the extent of edema can be used. Edema may also be measured in an animal model of edema. In such methods, the edema volumes (hemisphere volume of the ipsilateral side hemisphere volume of contralateral one) are calculated.

On CT and T1-weighted MRI, brain edema can be visualized as a hypodense or hyperintense lesion. Brain edema and other structures with a high water content, such as cerebrospinal fluid, are hyperintense on T2-weighted MRI. Fluid-attenuated inversion-recovery MR images provide additive information since brain edema is clearly visualized as a hyperintense lesion against an iso- or hyperintense background.

5.3.4.3 Meningitis

One side effect that can be monitored in a patient that has received an anti-beta amyloid antibody is meningitis. Any technique known to one of ordinary skill in the art to detect, monitor, or quantify the extent of minigitis can be used. A neurological examination may also be conducted, involving a series of tests designed to assess: motor and sensory function; nerve function; hearing and speech; vision; coordination and balance; mental status; and changes in mood or behavior. The function of the nervous system may be assessed through tests of strength and sensation, with the aid of items such as a tuning fork, small light, reflex hammer, and pins.

Analyzing the cerebrospinal fluid that surrounds and protects the brain and spinal cord can detect acute and chronic inflammation. In a procedure known as a spinal tap (or lumbar puncture), a small amount of cerebrospinal fluid is removed by a special needle that is inserted into the lower back. The skin is numbed with a local anesthetic prior to the sampling. The fluid, which is completely clear in healthy people, is tested to detect the presence of bacteria or blood, as well as to measure glucose levels (a low glucose level is a sign of bacterial or fungal meningitis) and white blood cells (elevated white blood cell counts are also a sign of infection). The procedure is usually done in a hospital and takes about 45 minutes.

Noninvasive imaging procedures are routinely used to reach a meningitis diagnosis. Such computer-assisted imaging can reveal signs of brain inflammation; internal bleeding or hemorrhage; and other brain abnormalities that may be associated with meningitis. Computed tomography, also known as a CT scan, combines x-rays and computer technology to produce rapid, clear, two-dimensional images of bones, organs, and tissues. Occasionally a contrast dye is injected into the bloodstream to highlight the different tissues in the brain and to detect inflammation of the meninges. Magnetic resonance imaging (MRI) uses computer-generated radio waves and a strong magnet to produce detailed images of body structures, including tissues, organs, bones, and nerves. A contrast dye may be injected prior to the test to reveal more detail. Another imaging technique used to assist in meningitis diagnosis is ultrasound.

Electroencephalography, or EEG, can identify abnormal brain waves associated with meningitis by monitoring electrical activity in the brain through the skull. EEG is used to help diagnose inflammation of the brain.

5.3.5 Tests for Functionality

5.3.5.1 Neuropsychological Tests

The functionality of an Alzheimer's disease treatment described herein can be assessed using one or more neuropsychological tests. Exemplary neuropsychological tests are described below and include, without limitation, those established by The Consortium to Establish a Registry for Alzheimer's Disease ("CERAD"; see, e.g., Morris J C, Mohs R C, Rogers H, Fillenbaum G, Heyman A. Consortium to establish a registry for Alzheimer's disease (CERAD) clinical and neuropsychological assessment of Alzheimer's disease. Psychopharmacol Bull. 1988; 24(4):641-52; Morris J C, Heyman A, Mohs R C, Hughes J P, van Belle G, Fillenbaum G, Mellits E D, Clark C. The Consortium to Establish a Registry for Alzheimer's Disease (CERAD). Part I. Clinical and neuropsychological assessment of Alzheimer's disease. Neurology. 1989 September; 39(9):1159-65; and Welsh K, Butters N, Hughes J, Mohs R, Heyman A. Detection of abnormal memory decline in mild cases of Alzheimer's disease using CERAD neuropsychological measures. Arch Neurol. 1991 March; 48(3):278-81).

In one embodiment, the functionality of an Alzheimer's disease treatment described herein can be assessed using the Alzheimer Disease Assessment Scale-Cognitive test ("ADAS-Cog"; see, e.g., Rosen W G, Mohs R C, Davis K L. A new rating scale for Alzheimer's disease. Am J Psychiatry. 1984 November; 141(11):1356-64; Ihl R, Brinkmeyer J, Janner M, Kerdar M S. A comparison of ADAS and EEG in the discrimination of patients with dementia of the Alzheimer type from healthy controls. Neuropsychobiology. 2000 January; 41(2):102-7; and Weyer G, Erzigkeit H, Kanowski S, Ihl R, Hadler D. Alzheimer's Disease Assessment Scale: reliability and validity in a multicenter clinical trial. Int Psychogeriatr. 1997 June; 9(2):123-38).

In another embodiment, the functionality of an Alzheimer's disease treatment described herein can be assessed using the Behavioral Pathology in Alzheimer's Disease Rating Scale ("BEHAVE-AD"; see, e.g., Reisberg B, Borenstein J, Salob S P, Ferris S H, Franssen E, Georgotas A. Behavioral symptoms in Alzheimer's disease: phenomenology and treatment. J Clin Psychiatry. 1987 May; 48 Suppl:9-15).

In another embodiment, the functionality of an Alzheimer's disease treatment described herein can be assessed using the Blessed-Dementia Information-Memory-Concentration Test (see, e.g., Blessed G, Tomlinson B E, Roth M. The association between quantitative measures of dementia and of senile change in the cerebral grey matter of elderly subjects. Br J Psychiatry. 1968 July; 114(512):797-811).

In another embodiment, the functionality of an Alzheimer's disease treatment described herein can be assessed using the Cambridge Neuropsychological Test Automated Battery ("CANTAB"; see, e.g., Swainson R, Hodges J R, Galton C J, Semple J, Michael A, Dunn B D, Iddon J L, Robbins T W, Sahakian B J. Early detection and differential diagnosis of Alzheimer's disease and depression with neuropsychological tasks. Dement Geriatr Cogn Disord. 2001; 12:265-280; Fray P J, Robbins T W. CANTAB battery: proposed utility in neurotoxicology. Neurotoxicol Teratol. 1996 July-August; 18(4):499-504; and Robbins T W, James M, Owen A M, Sahakian B J, McInnes L, Rabbitt P. Cambridge Neuropsychological Test Automated Battery (CANTAB): a factor analytic study of a large sample of normal elderly volunteers. Dementia. 1994 September-October; 5(5):266-81).

In another embodiment, the functionality of an Alzheimer's disease treatment described herein can be assessed using the Clock Draw Test (see, e.g., Sunderland T, Hill J L, Mellow A M, Lawlor B A, Gundersheimer J, Newhouse P A, Grafman J H. Clock drawing in Alzheimer's disease. A novel measure of dementia severity. J Am Geriatr Soc. 1989 August; 37(8):725-9; and Lee H, Swanwick G R, Coen R F, Lawlor B A. Use of the clock drawing task in the diagnosis of mild and very mild Alzheimer's disease. Int Psychogeriatr. 1996 Fall; 8(3):469-76).

In another embodiment, the functionality of an Alzheimer's disease treatment described herein can be assessed using the Cornell Scale for Depression in Dementia ("CSDD"; Alexopoulos G S, Abrams R C, Young R C, Shamoian C A. Cornell Scale for Depression in Dementia. Biol Psychiatry. 1988 Feb. 1; 23(3):271-84).

In another embodiment, the functionality of an Alzheimer's disease treatment described herein can be assessed using the Geriatric Depression Scale ("GDS"; see, e.g., Burke W J, Roccaforte W H, Wengel S P. The short form of the Geriatric Depression Scale: a comparison with the 30-item form. J Geriatr Psychiatry Neurol. 1991 July-September; 4(3):173-8).

In another embodiment, the functionality of an Alzheimer's disease treatment described herein can be assessed using the Mini Mental State Exam ("MMSE"; see, e.g., Folstein M F, Folstein S E, and McHugh P R. "Mini-Mental State": a practical method for grading the cognitive state of patients for the clinician. J Psychiatr Res. 1975; 12:189-198; and Cockrell J R, and Folstein M F. Mini-Mental State Examination (MMSE). Psychopharm Bull. 1988; 24(4):689-692).

In another embodiment, the functionality of an Alzheimer's disease treatment described herein can be assessed using the Neuropsychiatric Inventory ("NPI"; Cummings J L, Mega M, Gray K, Rosenberg-Thompson S, Carusi D A, Gornbein J. The Neuropsychiatric Inventory: comprehensive assessment of psychopathology in dementia. Neurology. 1994 December; 44(12):2308-14; Cummings J L. The Neuropsychiatric Inventory: assessing psychopathology in dementia patients. Neurology. 1997 May; 48(5 Suppl 6):S10-6).

In another embodiment, the functionality of an Alzheimer's disease treatment described herein can be assessed using the 7 Minute Screen (see, e.g., Solomon P R, Pendlebury W W. Recognition of Alzheimer's disease: the 7 Minute Screen. Fam Med. 1998 April; 30(4):265-71; and Solomon P R, Hirschoff A, Kelly B, Relin M, Brush M, DeVeaux R D, Pendlebury W W. A 7 minute neurocognitive screening battery highly sensitive to Alzheimer's disease. Arch Neurol. 1998 March; 55(3):349-55).

5.3.5.2 In Vivo Imaging

The functionality of an Alzheimer's disease treatment described herein can be assessed using in vivo imaging in subjects.

Imaging reagents can be administered by intravenous injection into the body of the patient, or directly into the brain by intracranial injection or by drilling a hole through the skull. The dosage of reagent should be within the same ranges as for treatment methods. Typically, the reagent is labeled, although in some methods, the primary reagent with affinity is unlabeled and a secondary labeling agent is used to bind to the primary reagent. The choice of label depends on the means of detection. For example, a fluorescent label is suitable for optical detection. Use of paramagnetic labels is suitable for tomographic detection without surgical intervention. Radioactive labels can also be detected using positron emission tomography (PET) or single photon emission computed tomography (SPECT).

Functionality of treatment can be assessed by comparing the number, size and/or intensity of labeled loci to corresponding base line values. The base line values can represent the mean levels in a population of individuals that do not have Alzheimer's disease. Alternatively, base line values can represent previous levels determined in the same patient. For example, base line values can be determined in a patient before beginning treatment, and measured values thereafter compared with the base line values. A decrease in values relative to base line can signal a positive response to treatment.

Anti-beta-amyloid antibodies are also useful to determine whether truncated forms of Aβ are present in cerebrospinal fluid or other body tissues or fluids. Presence of such forms at lessened levels in a patient relative to the base line can signal a positive response to treatment.

(1) Positron Emission Tomography

In one embodiment, the functionality of an Alzheimer's disease treatment described herein can be assessed by using radioactively-labeled tracers as probes with Positron Emission Tomography (PET) to monitor the pathophysiology of Alzheimer's disease (see, e.g., Någren et al. 2009, European Journal of Nuclear Medicine and Molecular Imaging, Radiopharmaceuticals for positron emission tomography investigations of Alzheimer's disease, published online Dec. 22, 2009.) For example, Carbon-11-labeled Pittsburgh compound B can be used as a radiotracer with PET to image the amyloid plaque burden (see, e.g., Rinne 2010, Lancet Neurology 9:363-372). Other tracers for PET imaging of amyloid plaque burden include $^{18}$F-labeled Stilbenes and Styrylpyridines (see, e.g., Kung et al. 2010, Journal of Medicinal Chemistry 53:933-941); the $^{18}$F-labeled benzothiazole (BTA)-derivative 3'-$^{18}$FFPIB; an $^{11}$C- and an $^{18}$F-labeled version of Congo-Red derivative SB-13; and the amino-naphthylderivative $^{18}$FFDDNP (see, e.g., Henriksen et al. 2008, European Journal of Nuclear Medicine and Molecular Imaging Suppl 1:S75-81).

(2) Magnetic Resonance Imaging

In one embodiment, the functionality of an Alzheimer's disease treatment described herein can be assessed by using Magnetic resonance imaging (MRI). MRI can be used to assess volume changes in the central nervous system (see, e.g., Fagan et al. 2009, Annals of Neurology 65:176-183) and to quantify vasogenic edema (see, e.g., Black et al. 2010, Alzheimer Disease and Associated Disorders 24:198-203).

5.3.5.3 Animal Models

In some embodiments, the functionality of an Alzheimer's disease treatment described herein can be tested in vivo using an model of Alzheimer's disease. Such animal models Alzheimer's disease are well-known in the art and include, without limitation, models using mice rats, and primates.

An exemplary murine model of Alzheimer's disease includes TgCRND8 mice (see, e.g., Chishti, M. A. et al., Early-onset amyloid deposition and cognitive deficits in transgenic mice expressing a double mutant form of amyloid precursor protein 695. J. Biol Chem 276, 21562-21570 (2001); Janus, C. et al., Aβ peptide immunization reduces behavioural impairment and plaques in a model of Alzheimer's disease. Nature 408, 979-982 (2000)). TgCRND8 mice express a human amyloid precursor protein transgene (APP695) bearing two missense mutations known to cause Alzheimer's disease in humans (KM670/671NL and V717F). At about three months of age, these mice display progressive spatial learning deficits that are accompanied both by rising cerebral Aβ levels and by increasing numbers of cerebral extracellular amyloid plaques. By six months of age, the levels of Aβ and the morphology, density and distribution of the amyloid plaques in the brain of TgCRND8 mice are similar to those seen in the brains of humans with well-established Alzheimer's disease. As in human patients with Alzheimer's disease, the biochemical, behavioral and neuropathological features of the mouse model are accompanied by accelerated mortality. Other exemplary murine models of Alzheimer's disease are known in the art and such mice are commercially available (see, e.g., the Alzheimer's Disease Mouse Model Resource available on the website of The Jackson Laboratory).

Primate models for Alzheimer's disease are also known in the art (see, e.g., Wenk, 1993, Behavioural Brain Research 57(2):117-122; and Fainman et al., 2007, American Journal of Medical Genetics 144B(6):818-819).

After treatment of such Alzheimer's disease in animal models, the functionality of the treatment can be assessed using methods known in the art including, without limitation, those described below.

(1) Survival Census

The probability of survival of mice can be assessed using the Kaplan-Meier technique, computing the probability of survival at every occurrence of death, thus making it suitable for small sample sizes. For analyses of survival, mice can be grouped in a control group and a treatment group(s) and the comparison between the groups can be assessed using, e.g., the Tarone-Ware test.

(2) Morris Water Maze Test

Morris Water Maze testing can be performed as previously described (see, e.g., Morris, R. Development of a water-maze procedure for studying spatial learning in the rat. J. Neurosci Methods 11, 47-60 (1984)). In this procedure, a mouse can be placed in a circular pool filled with water, with an escape platform submerged just below the surface of the water. A visible marker can be placed on the platform so that the animal can find it by navigating toward a proximal visual cue. (Alternatively, a more complex form of the test in which there are no formal cues to mark the platform's location can be given to the mice. In this form, the mice must learn the platform's location relative to distal visual cues.) The length of time the mice remain in the water is inversely related to cognitive ability.

An exemplary test is as follows: mice enter the Morris water maze test with a hidden platform on day one without pre-training. The mice can be tested for 3 days with six trials per day. On the fourth day, the platform can be removed from the pool and each mouse is given one 30-second swim probe trial. On the last day, the mice can be administered a cue test in order to evaluate their swimming ability, eye sight and general cognition. The cue test can be composed with the platform being placed in a different quadrant than that used for testing and can be tagged with a flag. Animals can be allowed 60 seconds to find the platform. Animals that do not find the platform are not used in the final analyses of spatial memory. Behavioral data can be analyzed using a mixed model of factorial analysis of variance (ANOVA) with drug or genotype and training sessions as repeated measure factors.

(3) Locomotor Activity

Locomotor activity can be assessed using known approaches, e.g., using a rotarod (San Diego Instruments, San Diego, Calif.). For example, mice can be analyzed for 2 days in the rotarod as previously described (see, e.g., Masliah, et al. (2000)). In such analysis, on the first day mice can be trained for 5 trials: the first one at 10 rpm, the second at 20 rpm and the third to fifth at 40 rpm. On the second day, mice can be tested for 7 trials at 40 rpm each. During the trials, the mice can be placed individually on the cylinder and the speed of rotation is increased to the appropriate speed over a period of time. The length of time mice remain on the rod (fall Latency) can be recorded and used as a measure of motor function.

(4) Cerebral Amyloid Burden

Cerebral amyloid burden can be tested as follows: brains from test animals can be removed and one hemisphere can be fixed in 4% paraformaldehyde and embedded in paraffin wax in the mid sagittal plane. To generate sets of systematic uniform random sections, 5 micrometer serial sections can be collected across the entire hemisphere. Sets of sections at 50 micrometer intervals can be used for analyses (10-14 sections/set). Plaques can be identified after antigen retrieval with formic acid, and incubation with primary anti-beta amyloid antibody (e.g., Dako M-0872), followed by secondary antibody (e.g., Dako StreptABCcomplex/horseradish kit).

End products can be visualized with diaminobenzidine (DAB) and can be counter-stained with, e.g., luxol fast blue. Amyloid plaque burden can be assessed using, e.g., Leco IA-3001 image analysis software interfaced with Leica microscope and Hitachi KP-M1U CCD video camera. Openlab imaging software (Improvision, Lexington, Mass.) can then used to convert micrographs to binary images for plaque number and plaque area determinations.

(5) Plasma and Cerebral Amyloid Beta

Levels of amyloid beta can be determined in the plasma and brain as follows: Hemi-brain samples can be homogenized in a buffered sucrose solution, followed by either 0.4% diethylamine/100 mM NaCl for soluble amyloid beta levels or cold formic acid for the isolation of total A. After neutralization, the samples can be diluted and analyzed for Aβ using commercially available kits (e.g., those provided by BIOSOURCE International). Western blot analyses can performed on all fractions using urea gels for Aβ species (see, e.g., Wiltfang, J. et al., Highly conserved and disease-specific patterns of carboxyterminally truncated Abeta peptides 1-37/38/39 in addition to 1-40/42 in Alzheimer's disease and in patients with chronic neuroinflammation J Neurochem 81, 481-496 (2002)). Amyloid beta can be detected using, e.g., 6E10 (BIOSOURCE International) and Enhanced Chemiluminenscence (Amersham).

(6) Analysis of APP in the Brain

APP can be detected in the brain as follows: Mouse hemibrain samples can be homogenized and spun at 109,000×g, in 20 mM Tris (pH 7.4), 0.25M sucrose, 1 mM EDTA and 1 mM EGTA, and a protease inhibitor cocktail, mixed with 0.4% DEA (diethylamine)/100 mM NaCl. The supernatants can be analyzed for APP levels by Western blotting using monoclonal antibody, while the pellets can be analyzed for APP holoprotein with, e.g., monoclonal antibody C1/6.1 as previously described (see, e.g., Chishti, M. A. et al., Early-onset amyloid deposition and cognitive deficits in transgenic mice expressing a double mutant form of amyloid precursor protein 695. J. Biol Chem 276, 21562-21570 (2001); and Janus, C. et al., A.beta. peptide immunization reduces behavioural impairment and plaques in a model of Alzheimer's disease. Nature 408, 979-982 (2000)).

(7) Long Term Potentiation

Field potentials can be recorded in the CA1 division of the mouse hippocampus using standard procedures (see, e.g., Sarvey, J M, Burgard E C & Decker G. Long-term potentiation: studies in the hippocampal slice. J Neurosci Methods 28, 109-124 (1989); and Stanton, P K & Sarvey J M. Norepinephrine regulates long-term potentiation of both the population spike and dendritic EPSP in hippocampal dentate gyms. Brain Res Bull. 18, 115-119 (1987)). The brains of mice can be removed and the hippocampus from each hemisphere can be isolated, from which, sections can be prepared (e.g., 350 μm coronal sections can be made). The sections can be transferred to a holding chamber containing NaCl-CSF and allowed to recover for more than 1 hour. Once placed in the chamber, the sections can be continuously perfused by a closed loop containing 15 ml of ACSF to conserve the oligomeric Aβ. After 20 minutes of stable baseline, 1 ml of 15× concentrated 7PA2 conditioned medium can be added to the perfusion loop. A bipolar stimulating electrode (e.g., those provided by World Precision Inst.) can be placed in the Schaffer collaterals to deliver baseline stimuli and tetani. A borosilicate glass recording electrode containing ACSF can be positioned approximately 75-200 μm from the stimulating electrode. The intensity of the stimulus (typically between 10-20 μAmps) can be set to obtain 25-40% of the maximal field potential response. Test stimuli can be delivered at 0.05 Hz. To induce long term potentiation, 4 tetani (100 Hz for 1 second) can be delivered 5 minutes apart. Field potential responses can amplified 10 times using, e.g., an Axopatch 200B. The data can be sampled at 10 kHz and filtered at 2 kHz. Traces can be analyzed using, e.g., pClamp 9.2. The slope of the field potential can be estimated using approximately 10-60% of the total response.

(8) Synaptophysin Quantification

Synaptophysin immunohistochemical staining can be performed on 3 evenly spaced saggital sections of paraformaldehyde-fixed treated and control mice. Sections can be immunolabelled for synaptophysin with, e.g., anti-synaptophysin IgG (1:40; Roche, Laval, PQ). Digital images can be captured and analyzed. Within each section, three randomly chosen 100 $\mu m^2$ areas of the CA1 region of the hippocampus can be counted for synaptophysin reactive cell bodies and boutons. The results can be expressed as the mean of the number of reactive bodies and boutons per 100 $\mu m^2$ (see, e.g., Chen, F. et al. Carboxyl-terminal fragments of Alzheimer beta-amyloid precursor protein accumulate in restricted and unpredicted intracellular compartments in presenilin 1-deficient cells. J Biol. Chem. 275, 36794-36802 (2002); Phinney, A. et al., No hippocampal neuron or synaptic bouton loss in learning-impaired aged β-amyloid precursor protein-null mice. Neuroscience 90, 1207-1216 (1999)).

(9) Conditioned Taste Aversion

Conditioned taste aversion (CTA) is a very sensitive, well known, standard test used to test an animal's cognitive function before and after administration of treatment. CTA is used to test an animal's ability for learning to associate illness with a novel stimuli, such as taste, such that the animals avoid the novel taste upon subsequent re-exposure to the novel stimuli. CTA involves the brain at a variety of cortical and subcortical levels. The association which links ascending and descending information together producing aversive behavior can be either attenuated or strengthened by changes affecting any of the interconnecting units. As a form of associative learning, the strength of CTA is determined by a large number of variables including novelty of the oral stimulus (e.g., non-novel stimuli cannot be aversively conditioned), degree of "illness" produced (toxicity), number of repetitions (training), countering drives (such as thirst) to name a few. Although a wide variety of chemical and physical agents can produce CTA in a dose-dependent manner, lithium chloride reliably produces malaise and anorexia. Like a naturally occurring illness, lithium produces a CTA by stimulating the pathways described above, including cytokine release.

(10) Barnes Maze

The Barnes maze consists of a circular table with circular holes around the circumference of the table. Under each hole is a slot for a box, called the drop box. The goal of animal in the maze is to reach the drop box, which is a box that has an open top, and can be reached through one of the holes in the top of the table. Exposure on the surface of the table serves as negative reinforcement, motivating the test subject to seek shelter. The only shelter available is the drop box, to which the test subject must flee. In order to accustom the test subject to the maze, it is guided into the drop box by a sheltering hand. After four to five runs, a normal test subject can quickly make locate the drop hole. Fixed visual cues set up around the platform serve to orient the rodent during the trials.

Performance is typically measured by the number of errors the subject makes, i.e. the number of times it pokes its nose into, or hovers its head over a circular hole that does not contain the drop box. The rate of decline in the number of errors/trial is measured across subjects. Other performance values can also be measured, for example the strategy used by each rodent can be scored as random (randomly checking each hole), systematic (checking each hole in a pattern) or spatial (direct movement to the hole with the drop box).

(11) Delayed Matching to Sample

The Delayed Matching to Sample (DMTS) procedure is commonly used to evaluate spatial recognition memory in laboratory animals. In an exemplary protocol, a subject is placed in a chamber equipped with two retractable levers and a food pellet dispenser. After a time period, a sample lever is presented, and the subject has to press the lever to get the food. The lever is then retracted and, after a delay of different duration, both levers are presented again and the subject is required to choose. Under matching conditions, a correct response would constitute pressing the lever which has been presented before and is recompensed by the delivery of a food pellet. An incorrect response is punished with 5 second time-out period during which the house light is turned off. Working memory is determined by analyzing the number of correct and incorrect responses of the subject.

(12) Microglial Activation

Activation of microglia can serve a beneficial role in the treatment of Alzheimer's disease. Thus, the functionality of an Alzheimer's disease treatment described herein can be assessed using known methods for measuring microglial activation (see, e.g., Higuchi, 2009, Current Alzheimer Research 6:137-143). Such methods utilize imaging techniques such as those described above, including PET imaging, to determine levels of microglia activation of treated subjects as compared to that of control subjects.

5.4 Methods of Treatment

Provided herein are methods for the safe and functional treatment of an amyloidosis, including, but not limited to, Alzheimer's Disease, using safe and functional antibodies. In certain embodiments, methods comprise the administration of a non-IgG1 antibody that binds specifically to an amyloid protein and/or its pathological form, such as aggregates, using a dose and/or administration regimen such that p38 MAP kinase is activated at intermediate levels in immune effector cells. The term "intermediate levels" in connection with p38 MAP kinase activation as used in this section means levels higher than in the absence of the antibody but lower than in the presence of an antibody with the same binding specificity but with the constant region of an IgG1 antibody. The levels of p38 MAP kinase activation can be determined as set forth in Section 5.1.

In certain embodiments, a non-IgG1 antibody that binds specifically to an amyloid protein and/or its pathological form, such as aggregates, is administered using a dose and/or administration regimen that results in maximal internalization of the target antigen, such as amyloid beta protein, into immune effector cells, such as microglia cells, and p38 MAP kinase activation at intermediate levels. In certain embodiments, the antibody is administered in combination with a modulator of the p38 MAP kinase pathway such that p38 MAP kinase is activated at intermediate levels.

In certain embodiments, the non-IgG1 antibody to be used with the methods herein is an antibody with the constant region of a human IgG4 antibody. In certain embodiments, the non-IgG1 antibody has the constant region of an IgG antibody with the CH2 domain of a human IgG4 antibody. In certain embodiments, the CDRs of a known non-humanized antibody that specifically binds human beta amyloid (see Table 2 below) are combined with the constant region of a human IgG4 antibody and the framework regions between the CDRs of the antibody are replaced with the framework regions of a human IgG antibody, such as IgG1, IgG2, IgG3, or IgG4. In certain embodiments, the variable regions of a known humanized anti-beta amyloid antibody, e.g., Bapineuzumab or Solanezumab, are combined with the constant region of a human IgG4 antibody.

Beta amyloid internalization into microglia and p38 MAP kinase activation can be measured using any technique known to one of ordinary skill in the art. In certain embodiments, the dosage of a safe and functional antibody of the invention to be used in the treatment of an amyloidosis including, but not limited to, Alzheimer's Disease is determined using a cell-based assay system described in Section 5.1. In particular, the dosage is adjusted such that internalization of beta amyloid into microglia is maximized while activation of the p38 MAP kinase pathway is activated by 5%-15%; 10%-20%; 15%-25%; 20%-30%; 35%-45%; 40%-50%; or 45%-55% less than p38 MAP kinase is activated in the presence of an IgG1 isotype anti beta amyloid antibody.

In certain embodiments, the administration regime of a safe and functional antibody of the invention to be used in the treatment of an amyloidosis including, but not limited to, Alzheimer's Disease is determined using a cell-based assay system described in Section 5.1. In particular, the dosage is adjusted such that internalization of beta amyloid into microglia is maximized while activation of the p38 MAP kinase pathway is activated by 5%-15%; 10%-20%; 15%-25%; 20%-30%; 35%-45%; 40%-50%; or 45%-55% less than p38 MAP kinase is activated in the presence of an IgG1 isotype anti beta amyloid antibody.

In certain embodiments, the dosage of a safe and functional antibody of the invention is adjusted such that internalization of beta amyloid into microglia is maximized while activation of the p38 MAP kinase pathway is activated by 5%-15%; 10%-20%; 15%-25%; 20%-30%; 35%-45%; 40%-50%; or 45%-55% above p38 MAP kinase activation levels in the absence of the antibody.

In certain embodiments, the administration regime of a safe and functional antibody of the invention to be used in the treatment of an amyloidosis including, but not limited to, Alzheimer's Disease is determined using a cell-based assay system described in Section 5.1. In particular, the dosage is adjusted such that internalization of beta amyloid into microglia is maximized while activation of the p38 MAP kinase pathway is activated by 5%-15%; 10%-20%; 15%-25%; 20%-30%; 35%-45%; 40%-50%; or 45%-55% above p38 MAP kinase activation levels in the absence of the antibody.

In specific embodiments, the amyloidosis is Alzheimer's Disease, the amyloid protein is beta-amyloid, and the immune effector cells are microglia cells. While the methods and compositions are set forth in more detail specifically for Alzheimer's Disease, these methods and compositions are generally applicable to treatment and prevention of amyloidoses including, but not limited to, secondary amyloidosis and age-related amyloidosis such as diseases including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), adult onset diabetes, endocrine tumors, and senile cardiac amyloidosis; and various eye diseases including macular degeneration, drusen-related optic neuropathy, and cataract due to beta-amyloid deposition. In specific embodiments, the amyloidosis is Alzheimer's Disease and the patient is a human patient.

In certain embodiments, Alzheimer's disease is treated using a combination of a safe and functional antibody provided herein and one or more of the following drugs currently used for the treatment of Alzheimer's disease, such as tacrine (COGNEX, Morris Plains, N.J.), donepezil (ARICEPT, Tokyo, JP), rivastigmine (EXELON, East Hanover, N.J.), galantamine (REMINYL, New Brunswick, N.J.), and memantine (NAMENDA, New York, N.Y).

5.5 Pharmaceutical Preparation and Administration

A safe and functional antibody provided herein (Section 5.2) can be prepared in a physiologically acceptable formulation and may comprise a pharmaceutically acceptable carrier, diluent and/or excipient using known techniques. For example, a safe and functional antibody as described herein is combined with a pharmaceutically acceptable carrier, diluent and/or excipient to form a therapeutic composition. Suitable pharmaceutical carriers, diluents and/or excipients are well known in the art and include, for example, phosphate buffered saline solutions, water, emulsions such as oil/water emulsions, various types of wetting agents, sterile solutions, etc.

Formulation of the pharmaceutical compositions provided herein can be accomplished according to standard methodologies known to one of ordinary skill in the art.

A pharmaceutical composition provided herein may be administered to a subject in the form of a solid, liquid or aerosol at a suitable, pharmaceutically functional dose. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal, interdermal, intraperitoneal, or parenteral (for example, intravenous, subcutaneous, or intramuscular) routes. In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. Commonly employed biodegradable matrices for the purposes of the invention include, but are not limited to a matrix of one of either polylactide, polyglycolide, or polylactide co-glycolide (co-polymers of lactic acid and glycolic acid).

It is well known to one of ordinary skill in the art that the dosage of the composition will depend on various factors such as, for example, the condition being treated, the particular composition used, and other clinical factors such as weight, size, sex and the general health condition of the patient, body surface area, the particular compound or composition to be administered, other drugs being administered concurrently, and the route of administration.

The composition may be administered in combination with other compositions comprising an biologically active substance or compound, particularly at least one compound selected from the group consisting of compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), α-secretase activators, β- and γ-secretase inhibitors, tau proteins, neurotransmitter, β-sheet breakers, attractants for beta amyloid clearing/depleting cellular components, inhibitors of N-terminal truncated beta amyloid including pyroglutamated amyloid beta 3-42, anti-inflammatory molecules, "atypical antipsychotics" such as, for example clozapine, ziprasidone, risperidone, aripiprazole or olanzapine or cholinesterase inhibitors (ChEIs) such as tacrine, rivastigmine, donepezil, and/or galantamine, M1 agonists and other drugs including any amyloid or tau modifying drug and nutritive supplements such as, for example, vitamin B12, cysteine, a precursor of acetylcholine, lecithin, choline, *Ginkgo biloba*, acetyl-L-carnitine, idebenone, propentofylline, or a xanthine derivative, together with an antibody according to the present invention and, optionally, a pharmaceutically acceptable carrier and/or a diluent and/or an excipient and procedures for the treatment of diseases.

Administration will generally be parenterally, e.g., intravenously. Preparations for parenteral administration include sterile aqueous or non-aqueous solutions, suspensions and emulsions. Non-aqueous solvents include, but are not limited to, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, anti-oxidants, chelating agents, inert gases, etc.

The pharmaceutical composition may further comprise proteinaceous carriers such as, for example, serum albumin or immunoglobulin, particularly of human origin. Further biologically active agents may be present in the pharmaceutical composition of the invention, depending on its intended use.

When the binding target is located in the brain, certain embodiments of the invention provide for the antibody or active fragment thereof to traverse the blood-brain barrier. Certain neurodegenerative diseases are associated with an increase in permeability of the blood-brain barrier, such that the antibody or active fragment thereof can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the antibody or active fragment thereof across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., Gene Therapy 9: 398-406 (2002)) and implanting a delivery device in the brain (see, e.g., Gill et al., Nature Med. 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Vols 1 & 2, Plenum Press, N.Y. (1989))), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the antibody or antigen-binding fragment (see, e.g., U.S. Patent Publication No. 2003/0083299).

Lipid-based methods of transporting the antibody or active fragment thereof across the blood-brain barrier include, but are not limited to, encapsulating the antibody or active fragment thereof in liposomes that are coupled to antibody binding fragments that bind to receptors on the vascular endothelium of the blood-brain barrier (see, e.g., U.S. Patent Application Publication No. 20020025313), and coating the antibody or active fragment thereof in low-density lipoprotein particles (see, e.g., U.S. Patent Application Publication No. 20040204354) or apolipoprotein E (see, e.g., U.S. Patent Application Publication No. 20040131692).

Receptor and channel-based methods of transporting the antibody or active fragment thereof across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

One of ordinary skill in the art will recognize or be able to ascertain, using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to one of ordinary skill in the art from the foregoing description and accompanying figures. Such modifications are intended to fall within the scope of the appended claims.

6. EXAMPLES

6.1 Identification of a Humanized IgG4 Antibody that Binds Equally to Multiple Aβ Conformation Murine anti-Aβ monoclonal antibodies were generated by immunizing mice with an Aβ peptide antigen using a liposomal vaccine formulation as previously described (Muhs et al., 2007). Several criteria were used to select candidate antibodies, including the ability to bind multiple Aβ species and to inhibit Aβ1-42 assembly into small cytotoxic peptide aggregates. A monoclonal murine mAb with an IgG2b backbone (mMABT) was selected for in vivo functionality studies using both single-transgenic murine mutant human APP and double-transgenic murine mutant human APP/PS1 models of Alzheimer's Disease. Treatment with mMABT improved memory and reduced plaque load (see FIG. 7). The mMABT was further affinity matured and humanized onto a human IgG4 backbone (the resulting antibody is also referred to as "MABT"). To test the binding of MABT to Aβ in vitro, a series of different Aβ1-42 preparations were made and characterized. These ranged from monomeric and oligomeric Aβ1-42 fractions isolated by size-exclusion chromatography (SEC), mature Aβ1-42 fibers, to a more complex mixture of highly neurotoxic Aβ1-42 oligomer assemblies, ranging in size from dimers and trimers to higher molecular-weight multimers (see FIG. 8). The binding of the MABT to different Aβ1-42 peptide preparations was measured by an ELISA, and similar to the mABT, was shown to be highly comparable among the different Aβ1-42 assembly states (FIG. 1A-C).

MABT was subsequently tested for binding to Aβ plaques in the brains of transgenic mice expressing the human amyloid precursor protein (hAPP) and to amyloid plaques in human AD brain sections. Amyloid plaques in both hAPP transgenic mice (FIG. 1D top) and in AD brain (FIG. 1D bottom) were immunodecorated with the MABT monoclonal antibody. Taken together, these data provide strong evidence of MABT binding to both soluble neurotoxic Aβ oligomers and Aβ assemblies present in AD brains.

6.2 Inhibition of Pathological Aβ Assembly and Disaggregation of Pre-Formed Protofibrillar Aβ1-42 Peptides In vitro data has demonstrated that anti-Aβ antibodies when combined with Aβ can prevent the formation of pathological higher-order Aβ assemblies and reverse pre-formed Aβ aggregates (Legleiter et al., 2004; Solomon et al., 1997). The binding epitope of the MABT monoclonal antibody was mapped to amino acids 14 to 23 of Aβ1-42, and therefore overlaps with the main hydrophobic cationic segment of Aβ1-42 responsible for the self-association, subsequent oligomerization, and the core of Aβ1-42 β-sheet assembly (Pike et al., 1993; Esler et al., 1996; Haass and Selkoe, 2007). The effects of MABT on in vitro Aβ1-42 aggregation were tested using thioflavin-T (ThT), a dye that does not impede amyloid assembly but fluoresces upon binding to small amyloid aggregates rich in β-sheets (Levine, III, 1993). When compared to a control anti-Aβ monoclonal antibody directed against the N-terminus of Aβ1-42, (and thus not overlapping with the core amino acids that form the self-assembly domain), MABT demonstrated a strong inhibitory effect on Aβ1-42 aggregation (FIG. 1E left panel), and the dissipation of pre-aggregated Aβ1-42 peptide (FIG. 1E right panel). The control monoclonal antibody, directed against the N-terminus of Aβ, had about half the inhibitory activity compared to the anti-mid-domain MABT monoclonal antibody in both assays. Similar results were obtained when the MABT was compared to an anti-C-terminal anti-Aβ monoclonal antibody (not shown). These in vitro assays are based on the ability of ThT to bind to extended β-sheets of the Abeta1-42 peptide (Levine, III, 1993). Therefore, to verify that this was not an artifact due to potential monoclonal antibody-mediated displacement of ThT binding to β-sheet rich Aβ1-42, an assay which does not rely on ThT fluorescence, but rather on the capacity of labeled Aβ1-42 to aggregate or self-assemble onto immobilized un-labeled Aβ1-42 was performed. Comparable results were obtained in this assay, namely that the MABT prevented the self-assembly of Aβ1-42 in a dose-dependent manner (FIG. 1F). These data demonstrate that an antibody directed against the mid-domain of Aβ such as MABT provides the most robust inhibitory effect on Aβ1-42 fibril elongation and/or aggregation relative to antibodies targeting other domains of Aβ in this assay.

The ability of soluble Aβ1-42 oligomers to bind other proteins, both soluble and membrane-bound, has been shown to contribute to its toxicity (Strittmatter et al., 1993; Liu et al., 2009). The interaction site of ApoE4 with Aβ1-42 requires amino acids 18 to 28 (Strittmatter et al., 1993). The effect of MABT on Aβ1-42 binding to recombinant human ApoE4 was tested in vitro, and compared to monoclonal antibodies specific for the N- or C-terminus of Aβ1-42. Under conditions where saturating concentrations of ApoE4 and Aβ1-42 were used, MABT inhibited over 80% of the Aβ1-42 and ApoE4 interaction, greater than with any of the other monoclonal antibodies tested (see FIG. 9). To summarize, these data show that MABT prevents further oligomerization of Aβ1-42 into toxic biologically active assembly states and dissipates already aggregated or plaque-bound Aβ1-42. Furthermore, with a centrally located binding epitope, MABT can compete for the interaction of Aβ peptides to other proteins, such as ApoE, thus blocking interactions with Aβ that require amino acids in the Aβ central domain, including self-association.

6.3 MABT-Mediated Neutralization of the Neurotoxic Effects of Aβ1-42 Oligomers in Vitro With both biochemical and in vivo functionality data showing a therapeutic functionality for the MABT monoclonal antibody, the effects of MABT monoclonal antibody in a primary cell-culture model were tested using cytotoxic Aβ1-42 oligomers. Primary cortical cultures from P1 rats were grown and treated with free Aβ1-42 oligomers or oligomers complexed to MABT. A non-specific IgG monoclonal antibody was used as a control in all experiments. Treatment of cortical cultures with 2.5 or 5 µM Aβ1-42 oligomers over 24 h resulted in a reduction in metabolic turnover as measured by mitochondrial oxidation of MTT (FIG. 2A), an indicator of cell viability. A complete rescue from toxicity was observed for Aβ1-42 oligomer concentration up to 5 µM in the presence of MABT (MABT to Aβ1-42 oligomer molar ratio of 1:7.5). To confirm these results, ATP release was measured using a luminescence assay, and also showed similar cytoprotective effect of MABT (FIG. 2B). To further assess the effect of MABT on Aβ1-42-mediated neuronal cell death, mouse embryonic cortical neurons were kept in culture for six days, and treated with Aβ1-42 with or without MABT for four days. Control cultures showed healthy morphology (FIG. 2C, leftmost panel). Treatment with Aβ1-42 for four days resulted in axon degeneration and caused a decrease in the total number of axons (FIG. 2C, center panel). Cells treated with the combination of Aβ1-42 and MABT appeared similar to control cells (FIG. 2C, rightmost panel). These results demonstrate that the anti-Aβ MABT monoclonal antibody was able to protect both rat cortical cultures from acute Aβ1-42 oligomer-mediated loss of viability and embryonic mouse cortical neurons from Aβ1-42-induced degeneration.

6.4 Aβ1-42 Oligomer Interaction with Cell-Membranes is Inhibited by Anti-Aβ MABT mAb Aβ peptides, especially aggregation intermediates (Bateman et al., 2007), are known to associate with various lipids and proteins present in cell membranes. Whether MABT may exert its neuroprotective effects by reducing or even blocking the binding of Aβ1-42 oligomers to neurons was tested. An immunofluorescence staining for membrane-bound Aβ was performed. Aβ1-42 oligomers were applied to mixed cortical cultures for 30 min or 18 h, after which cultures were stained for Aβ and with an antibody to the neuron-specific class III β-tubulin, TuJ1. Treatment of cortical neurons with Aβ1-42 oligomers resulted in a strong association of Aβ with neurons, in particular with neuritic processes (FIG. 3A, middle panels and insets). Co-treatment with MABT blocked the interaction of Aβ1-42 oligomers with neurons, especially binding to neuronal processes. This effect was readily apparent as early as 30 min (FIGS. 3A and 3B) and remained for at least 18 h of treatment (FIG. 3B). Although an N-terminal anti-Aβ mAb (clone 6E10) was used in our assay to stain for Aβ1-42 oligomers (FIG. 3A), thus reducing the potential for interference between MABT and the detection monoclonal antibody used for the staining, these results were confirmed using HiLyte Fluor-488 fluorescently labeled Aβ1-42. Treating cortical cultures with this directly labeled Aβ1-42 peptide further supported the conclusion that the MABT reduced binding of Aβ1-42 to neuronal processes in primary cortical cultures (FIGS. 3C and 3D).

The buildup of intraneuronal Aβ1 42 has been shown to significantly contribute to neuronal dysfunction (Casas et al., 2004; Wirths et al., 2001; Cleary et al., 2005; Oddo et al., 2003). The intracellular accumulation of Aβ1-42 was determined in trypsin-cleared cells using an ELISA assay. This analysis demonstrated that MABT reduced Aβ1-42 oligomer internalization by more than 60% (FIG. 3E). Unexpectedly, observations from immunofluorescence studies also indicated that in the presence of MABT, there was a shift in Aβ1-42 oligomer association away from neuronal processes toward cellular profiles that resembled microglia (FIG. 3F).

6.5 Microglial Uptake of Aβ1-42 Oligomers

The relationship between MABT/Aβ1-42 complex formation and microglial uptake of Aβ1-42 was investigated. To verify that Aβ1-42 oligomers complexed to MABT are taken up by microglia, confocal imaging on treated mixed neuronal cultures was performed. When compared to cells treated with Aβ1-42 oligomers alone, it was found that MABT mediated rapid uptake of Aβ1-42 oligomers into cellular profiles likely to be microglia (FIG. 4A). This was readily apparent as early as 30 minutes following treatment. Microglia play a crucial role in uptake and degradation of Aβ, a function that is compromised in APP mice (Hickman et al., 2008). Relative to anti-Aβ immunotherapy, it has been proposed that one possible mechanism whereby Aβ plaques are cleared is through the FcγR-binding properties of anti-Aβ bound to Aβ (Koenigsknecht-Talboo et al., 2008). However, uptake of anti-Aβ/Aβ complexes by microglia and FcγR activation may trigger these cells to become activated.

In addition to overcoming the direct cytotoxicity of Aβ1-42 oligomers on neurons, a therapeutic anti-Aβ antibody ideally would have a significantly reduced proinflammatory response with a significantly reduction in the negative consequences resulting from such a proinflammatory response. Therefore MABT was compared to antibodies carrying the same antigen binding sequences, but harboring different IgG backbones with variable FcγR binding affinities, and therefore, different microglia activating potential. These included a human IgG1 wild-type with full FcγR-binding capacity (MABT-IgG1), and a human IgG1 backbone carrying a D265A mutation (MABT-IgG1-D265A) that dramatically reduces FcγR-binding (Shields et al., 2001). All of the backbone variants tested bound with similar affinity to Aβ1-42, as verified using surface plasmon resonance.

The ability of these different monoclonal antibody backbones to internalize Aβ1-42 oligomers into microglia was then compared using confocal imaging on Aβ1-42 oligomer treated primary cortical microglia. It was found that Aβ1-42 oligomer internalization correlated well with FcγR-binding, with MABT-IgG1>MABT>MABT-IgG1-D265A (FIGS. 4B and 4C). To verify that microglia are indeed the cells taking up Aβ1-42 complexed to monoclonal antibodies, the study was repeated using HiLyte Fluor-488 tagged Aβ1-42 and co-stained for the microglial marker Iba1. Upon binding to either MABT or the MABT-IgG1 monoclonal antibody, tagged Aβ1-42 became enriched in Iba1+ microglia (FIG. 4D). In cell cultures treated with Aβ1-42 in combination with the MABT-IgG1 monoclonal antibody, microglia had more condensed nuclei and brighter Iba1 staining, features suggesting greater antigen/antibody-mediated microglial activation. To verify the FcγR-binding differences, the binding of the different cross-linked IgG mAb to the low-affinity FcγRIIIa-V158 was measured, and a hierarchy of binding was identified wherein MABT-IgG>MABT>MABT-IgG1-D265A (FIG. 4E). Binding to other members of the FcγR family is shown in FIG. 10.

The different IgG monoclonal antibody backbones were tested for their ability to reverse Aβ1 42 oligomer-mediated toxicity in mixed primary cortical cultures. Functional FcγR binding activity, present for both the MABT and MABT-IgG1 monoclonal antibodies was required for full reversal of Aβ1-42 oligomer-mediated toxicity (FIG. 4F). The MABT-IgG1-D265A monoclonal antibody, which lacks FcγR binding functionality, showed only a non-significant trend towards reversal of Aβ1-42 oligomer-mediated cellular toxicity. Surprisingly, the MABT-IgG1 wild-type monoclonal antibody, which bears greater FcγR-binding affinity compared to the IgG4 MABT monoclonal antibody, trended towards a smaller protective effect when compared to MABT. Thus, while binding to microglial FcγRs is needed for full rescue, the enhanced binding of the MABT-IgG1 backbone to FcγRs as compared to that of a MABT may result in undesired microglia activation, which may translate into reduced overall protection against Aβ1-42 oligomer-mediated neurotoxicity.

6.6 the MABT-IgG1 Wild-Type Backbone Leads to Pro-Inflammatory Microglia Response In efforts to identify downstream mediators of Aβ1-42 oligomer-induced toxicity whose activation states are altered by the anti-Aβ monoclonal antibodies, several candidate signaling pathways were examined. The role of p38MAPK in contributing to neurotoxicity and microglial activation has been widely documented (Li et al., 2004; Wang et al., 2004). p38MAPK activation was examined in primary mixed cortical cultures treated with Aβ1-42 oligomers alone or in combination with the anti-Aβ MABT, MABT-IgG1, MABT-IgG1-D265A, or a control IgG1 that does not bind to Aβ1-42 oligomers. When cells were treated with Aβ1-42 oligomers, p38MAPK was activated within 15 min (not shown) and reached a maximum at 30 min. Upon combination with the different monoclonal antibodies, only MABT-IgG1, carrying the IgG1 wild-type backbone and having the greatest binding affinity to FcγR, increased the Aβ1-42 oligomer-induced p38MAPK activity even further as shown by a phospho-p38MAPK-specific ELISA (FIG. 5A). Since the various anti-Aβ antibodies bind with similar affinity to Aβ1-42, the MABT-IgG1 monoclonal antibody should neutralize toxic Aβ1-42 oligomers to the same degree as MABT. However, the greater FcγR-binding affinity of the IgG1 backbone may result in microglia activation that can be detrimental to cells that are highly susceptible to the actions of Aβ1-42 oligomers, such as neurons. The MABT monoclonal antibody complexed to Aβ1-42 oligomers did not reduce the Aβ1-42 oligomer-induced p38MAPK activity, but rather showed a trend towards higher activity, reflecting the partial FcγR activation by this antibody.

As these initial assays measured the total p38MAPK activity in mixed cortical cultures, including both neuronal and glial cells, the question whether the p38MAPK activity detected when cells were treated with the combination of Aβ1-42 oligomers and MABT was specific to microglia was tested. Cells were treated as previously, but this time phospho-p38MAPK activity was examined by immunofluorescence staining along with the microglia marker Iba1. Upon treatment with Aβ1-42 oligomers complexed to MABT or MABT-IgG1 monoclonal antibodies, approximately 93% of cells staining positive for phospho-p38MAPK were Iba1+ (FIG. 5B). To confirm the activation of p38MAPK in microglia, purified microglia were treated in the same way. Under these conditions, Aβ1-42/IgG complex-mediated p38MAPK activation in microglia was readily identified (FIG. 5C).

To address the contribution of p38MAPK activation to Aβ1-42 oligomer-mediated neurotoxicity, cells were treated with a second generation p38MAPK-specific inhibitor, and then with Aβ1-42 oligomers alone or in combination with either the MABT or the low-FcγR-binding MABT-IgG1-D265A monoclonal antibody. Unexpectedly, the MABT-mediated increase in MTT signal was reduced to that of MABT-IgG1-D265A in presence of the p38MAPK inhibitor, indicating a reduction in MABT-mediated rescue function upon p38MAPK inhibition (FIG. 5D). p38MAPK inhibition had no effect on cells treated with Aβ1-42 oligomers complexed with the MABT-IgG1-D265A monoclonal antibody. These results demonstrate that although the MABT monoclonal antibody does not significantly induce p38MAPK levels over those seen with Aβ-1-42 oligomers alone, p38MAPK activation does play a role in MABT-mediated neuroprotection. Without being bound by theory, the cellular targets of this activity in the mixed culture system are microglia cells.

To link the increased microglia activity more directly to a downstream pro-inflammatory readout, the TNFα release by primary cell cultures enriched for microglia was measured (>61% Iba1+, not shown). The release of pro-inflammatory TNFα by enriched microglia when treated with Aβ1-42 oligomers was reduced in the presence of all anti-Aβ monoclonal antibodies tested (FIG. 6). However, the greatest effect was observed in the presence of MABT. Thus, an anti-Aβ IgG4 monoclonal antibody may have a more desirable profile as compared to an anti-Aβ IgG1 monoclonal antibody, combining neuroprotective effects and ability to promote Aβ engulfment by microglia with limited microglial activation.

6.7 Materials and Methods

6.7.1 Cell-Culture Preparation

Rat primary cortical cultures were prepared from Sprague-Dawley rats (Charles River Laboratories L'Arbresle, France) at post-natal day 1, as described by Meberg and Miller (Meberg and Miller, 2003). Cerebellum and meninges were removed, and cortices were cut into small pieces and dissociated with enzymatic disruption at 37° C. in dissociation buffer (papaine, $CaCl_2$, EDTA, and HEPES; all from Invitrogen, Carlsbad, Calif.). DNase (Invitrogen) was added for 10 min. Following dissociation, dispersed cortical neurons were plated onto poly-L-lysine (0.01%; mol. wt 150,000-300,000; Sigma) coated 6-well, 24-well, or 96-well tissue culture plates. For immunocytochemistry, cells were grown on coated glass coverslips, into 24-well plates. Cells were maintained in Neurobasal media (Invitrogen) without phenol-red, with the addition of L-glutamine (2 mM; Sigma), B27 supplement (Invitrogen), and penicillin/streptomycin (Sigma) in a humidified incubator at 37° C. and 5% $CO_2$. Following 1 h and 30 min in culture, the media was replaced with astrocyte-conditioned medium. After a further 4 days in culture, cell proliferation was blocked by treatment with cytosine arabinoside (Ara-C) at 2.5 µM (Invitrogen). Under these culture conditions, 20% of cells were identified as neurons by NeuN/DAPI staining (not shown). Experiments using mixed cortical cultures were generally performed at days-in-vitro ("DIV") 6 unless stated otherwise. Enriched microglia prepared from cortex and hippocampus were harvested as described for cortical cultures above. Cortex and hippocampus were put in DMEM containing high glucose and homogenized by pipetting with a 10 mL pipette and then with a syringe. The homogenate was centrifuged for 3 min at 1,000×g, and then resuspended in pre-warmed DMEM containing high glucose containing 10% FCS and penicillin/streptomycin (microglia media). The cell suspension was next transferred to a T75 tissue-culture flask and kept in a humidified incubator at 37° C. and 5% $CO_2$ for 1 week. The flask was shaken to separate microglia from adherent cells, and collected and washed in DMEM. The resulting cells were resuspended in 1 mL microglia media, counted, and plated at $5 \times 10^4$ cells/well. To verify microglial enrichment, cells were stained with the astroglial and microglial markers GFAP and Iba1, respectively. Greater than 60% of cells stained positive for Iba1, with no cells staining for both GFAP and Iba1. Pure microglia were prepared from post-natal day 3 CX3CR1-GFP mice (Jackson Laboratories). Cortex and hippocampus were dissected and triturated in DMEM containing high glucose using a 10 mL pipette, and then with an 18 gauge needle. The homogenate was centrifuged for 3 min at 1,000 g, and then resuspended in pre-warmed DMEM containing high glucose, 10% FBS and penicillin/streptomycin (microglia media). The cell suspension was next transferred to a T75 tissue-culture flask and kept in a humidified incubator at 37° C. and 5% $CO_2$ for 7-10 d. Microglia were isolated by shaking, collected and washed in DMEM. The resulting cells were resuspended in 1 mL microglia media, counted, and plated on tissue culture treated glass chamber slides at $5 \times 10^4$ cells/well for use in experiments.

6.7.2 Generation of Anti-Aβ Antibodies

The IgG4 anti-Aβ monoclonal antibody MABT is a humanized form of mouse IgG2b monoclonal antibody (mMABT) generated by immunizing mice with a vaccine prepared as previously described (Muhs et al., 2007).

6.7.3 FcγR Binding

The binding of test antibodies to a panel of human Fcγ receptors (FcγRs) was measured using enzyme-linked immunosorbent assay (ELISA). Human FcγRs (Genentech, Inc., CA) are fusion proteins containing the extracellular domain of the receptor γ-chain with a Gly/6xHis/glutathione S transferase (GST) polypeptide tag at the C terminus. A monoclonal antibody with human IgG1 framework was used as the positive control (IgG1 control) in this experiment. Plates were coated with a mouse monoclonal anti GST antibody (Genentech, Inc.) in a 0.05 M sodium carbonate buffer (pH 9.6) overnight at 4° C. After blocking with an assay buffer containing phosphate buffered saline (PBS), 0.5% BSA, and 0.05% Tween-20, the plates were incubated with FcγRs at room temperature for 1 h. Human FcγRs were immobilized to the plate via interaction with the anti-GST coating. Serial dilutions of anti-Aβ MABT, MABT-IgG1, MABT-IgG1-D265A, or IgG1 control monoclonal antibodies were prepared in the assay buffer containing 10% Blocker Casein in PBS (Pierce; Rockford, Ill.). Diluted samples were applied as monomeric forms for the high affinity receptor (FcγRIa), or multimeric forms for the low affinity receptors (FcγRIIa, FcγRIIb, and FcγRIIIa). The multimeric forms of test antibodies were generated by cross linking $F(ab')_2$ fragment of goat anti human κ-chain (MP Biomedicals, Solon, Ohio), with test monoclonal antibody at an approximate molar ratio of 3:1. The plates were incubated with FcγRs at room temperature for 2 h. Plates were washed three times with wash buffer containing PBS and 0.05% tween-20 after each incubation step. The antibodies bound to the FcγRs were detected with horseradish peroxidase (HRP)-conjugated F(ab')2 fragment of goat anti human $F(ab')_2$ (Jackson ImmunoResearch Laboratories; West Grove, Pa.). Tetramethylbenzidine (TMB; Kirkegaard & Perry Laboratories, Gaithersburg, Md.) served as a substrate. Plates were incubated at room temperature for 15 to 20 min to allow color development. The reaction was terminated with 1 M H3PO4, and absorbance at 450 nm with reference at 650 nm was measured on a plate reader (Molecular Devices, Sunnyvale, Calif.). Binding curves were generated by plotting the mean absorbance values from duplicates of sample dilutions against the respective sample absorbance.

6.7.4. In Vivo Functionality Studies

Two studies were performed for in vivo functionality assessments. To measure recall memory, 12 mutant human APP mice per group received two i.p. injections of MABT monoclonal antibody or vehicle control (PBS). One day after the second injection, recall memory was studied using the novel object recognition task (ORT) as described (Dewachter et al., 2002). Recognition index (RI) was defined as the ratio of the time spent exploring a novel object over the time spent exploring both a novel and an object observed 3 h previously, a measure of nonspatial memory engaging the hippocampus. In a separate study, double transgenic amyloid-plaque positive mutant human APP/PS1 mice were used to measure the effect of monoclonal antibody administration on cortical plaque load. Mice were injected i.p. weekly with 500 µg MABT monoclonal antibody over a 16 week period, after which cortical plaque load was measured. Brains were dissected and the right cerebral hemisphere was immersion fixed in 4% paraformaldehyde in PBS overnight and sagittal vibratome sections (40 µm) were cut for free floating incubations and stored at 4° C. in PBS with 0.1% sodium azide until staining. Five sections at different levels were stained for dense plaques with thioflavin-S. Sections were randomized for staining and blind quantification. Images were acquired with a Leica DMR microscope equipped with a Sony DXC- 9100P camera and analyzed with a computer using Leica Q-Win software. Light intensity and condenser settings for the microscope were kept constant throughout the image acquisition process. The area of the subiculum was selected for automatic quantification of the amyloid load in the thioflavin-S staining.

6.7.5 Preparation of Toxic Aβ1-42 Oligomers

Aβ1-42 peptide (Bachem) was dissolved in HFIP, sonicated and shaken overnight at room temperature. Aliquots were then dried under a flow of argon, vacuum dried and stored at −80° C. as monomeric Aβ1-42 peptide film until use. A 165 µg aliquot of peptide film was resuspended in 7 µL DMSO, 85 µL PBS, and 9 µL of 2% SDS and incubated for 6 h at 37° C. Then, 300 µL of water was added, and after an overnight incubation at 37° C., Aβ1-42 oligomers were precipitated with 900 µL of 33% methanol 4% acetic acid solution for 1 h at 4° C., centrifuged at 16,200 g for 10 min. Supernatant was removed and Aβ1-42 oligomers were dried before being resuspended in $Na_2HPO_4$/NaCl solution for a final concentration of 1 µg/µL.

6.7.6 Aβ1-42 Cytotoxicity Assays

The cytotoxicity of Aβ1-42 oligomers was tested on mixed cortical cultures at DIV 5. All antibodies, at a final concentration of 100 µg/mL, were co-incubated with Aβ1-42 oligomers for 30 min in serum-free cell culture medium at 37° C. before treatment of cells. For some experiments, mixed cortical cultures were pre-treated for 1 h with 1 µM SB239063, a potent second-generation p38 inhibitor, before treatment with Aβ1-42 oligomers. To evaluate cell viability, standardized 3-(4,5-dimethylthiazol-2-yl)-2,5-diphenyltetrazolium bromide (MTT) reduction assays (Promega, Madison, Wis., USA) were carried out, following the manufacturer's instructions. To evaluate cell viability in response to various treatments, standardized 3-(4,5-dimethylthiazol-2-yl)-2,5-diphenyltetrazolium bromide (MTT) reduction assays (Promega, Madison, Wis., USA) were carried out. Briefly, for the last 3 h of treatment, cells grown in 96-well plates (Costar) were incubated with the MTT dye solution and the generation of a blue formazan product was measured by reading absorbance at 570 and 690 nm using a plate reader (Tecan). Results are presented as a percentage increase in survival over Aβ1-42 oligomer-treated cells. The ability of the MABT monoclonal antibody to protect neurons from Aβ1-42 oligomer-induced degeneration was also assessed in an in vitro assay using immunofluorescence. Embryonic day 17.5 mouse cortical neurons were isolated, dissociated, and cultured in vitro in Neurobasal media with B27 supplement. Aβ1-42 was prepared as described above for Aβ-42 monomeric peptide film, after which 10 µL of DMSO was added to dissolve the peptide. Then, 78.6 µL of Ham's-F12 media was added and the Aβ1-42 peptide solution at 25 µM was incubated at 4° C. for 48 h before cell treatment. Cells were grown for nine days in total, and were fed on day 3 and on the day of treatment. For treatment, Aβ1-42 at 2 µM with or without MABT at 50 µg/mL was added at day 5 or day 6, with DMSO-F12 alone at the same volume was used as vehicle control. On day 9, following 3 or 4 days of treatment, neurons were fixed and stained with TuJ1, an anti-β-tubulin antibody. A FITC-labeled secondary antibody was used to visualize microtubules using fluorescence microscopy.

6.7.7 Immunohistochemistry

Paraffin mounted temporal lobe brain sections (20 µm) from an AD patient and from an age-matched non-AD control (Tissue Solutions, Clydebank, UK) were used for immunohistochemistry staining. Deparaffinized sections were subjected to antigen retrieval using formic acid and then labeled with 50 µg/mL MABT as the primary antibody. A goat-anti-human biotinylated IgG was used as a secondary antibody. Staining was done with diaminobenzidin (Dako, Glostrup, Denmark) and mounting using Eukitt mounting medium. Images were acquired on a LSM 700 inverted microscope from Zeiss.

6.7.8 Aβ1-42 ELISA

To measure intracellular Aβ1-42 accumulation by ELISA, primary cortical cultures were treated in 6-well cell-culture plates (Costar) after which they were washed and trypsin-cleared (Bateman et al., 2007) before lysis in cell-lysis buffer consisting of 50 mM Tris-HCl (pH 8.0), 150 mM NaCl, 5 mM EDTA, 1 mM sodium orthovanadate, 1% Triton X-100, and containing protease- and phosphatase-inhibitor cocktails. Protein concentration was determined by the BCA assay (Pierce). A high-sensitive Aβ1-42-specific ELISA (The Genetics Company, Inc., Zurich, Switzerland) was used to measure cell-lysate Aβ1-42 according to the manufacturer's instructions.

6.7.9 Immunocytochemistry and Confocal Imaging

Cells were grown on a glass coverslips. Following treatment, cells were quickly washed with PBS and then fixed with 4% paraformaldehyde for 20 min. After thorough washes, cells were immersed in 100% methanol for 10 min at −20° C. They were then washed again and incubated in a blocking solution, PBS containing 10% normal goat serum for 1 h at room temperature. After an overnight incubation with the primary antibody, cells were washed and incubated for 2 h with the secondary antibody, then washed and mounted on glass slides using ProLong Gold antifade reagent (Invitrogen). Epifluorescence and confocal images were acquired on a LSM 700 inverted microscope from Zeiss, using a 63× lens. Fluorescence intensity was measured in cell bodies delineated by saturated epifluorescence pictures. Z-stacks were rendered into a three-dimensional image using ImageJ 1.42 (National Institutes of Health, freeware) from which an apical to distal slice containing the labeled proteins was obtained. Cells treated with HyLite Fluor-488-tagged Aβ1-42 were treated in the same way except no primary or secondary antibodies were used to label for Aβ1-42.

6.7.10 Phospho-p38 ELISA

Rat cortical cultures were seeded onto poly-L-lysine coated 6-well cell-culture plates (Costar, Cambridge, Mass., USA) and used at DIV 5. Unless otherwise indicated, cells were treated with 2 µM Aβ1-42 oligomers with or without monoclonal antibody at 100 µg/mL for 30 min. In some assays, cells were pre-treated for 1 h with the second-generation p38 inhibitor SB239063. Anisomycin was used as a positive control. Treatments were stopped by placing cells on ice and aspirating the medium. Cells were washed with ice-cold PBS, harvested using a cell scraper, and lysed in lysis buffer consisting of 50 mM Tris-HCl (pH 8.0), 150 mM NaCl, 5 mM EDTA, 1 mM sodium orthovanadate, 1% Triton X-100, and containing protease- and phosphatase-inhibitor cocktails. Protein concentration was determined by the BCA assay (Pierce, Rockford, Ill., USA). For semi-quantitative measure of p38MAPK activation, a rat phospho-p38MAPK colorimetric ELISA kit was used (Cell Signaling Technology, Beverly, Mass., USA), following the manufacturer's instructions. Plates were read on a spectrophotometric microplate reader (Tecan) at a 370 nm. For some experiments, phospho-p38 was assayed using immunocytochemistry.

6.7.11 TNFα Release

Rat cortical cultures enriched for microglia (>60% Iba1[+] of total DAPI[+] cells) were treated with 10 µM Aβ1-42 oligomers with or without 100 µg/mL antibodies for 6 h and 24 h. LPS (Sigma) at 1 µg/mL was used as a positive control stimulus. Cell supernatants were removed at the indicated time-points, passed through a 0.2 µm filter, and tested for TNFα with a Quantikine rat TNFα/TNFSF1A (R&D Systems), following the manufacturer's instructions.

Further, pure microglial cultures from CX3CR1-GFP P3 pups are treated with 1 µg/ml LPS, 10 µM Aβ1-42 oligomers alone or in combination with 100 µg/ml anti-Aβ MABT, MABT-IgG1, MABT-IgG1-D265A, control IgG1, or antibodies alone for 24 hours. Cell supernatants are harvested, passed through a 0.2 µm filter, and run on a Bio-Plex mouse 23-plex assay (Bio-Rad, Hercules, Calif., USA).

6.7.12 Statistical Analysis

All statistical analyses were done using GraphPad Prism version 5 (GraphPad Software, San Diego, Calif., USA). Data are presented as means±standard deviation (SD) or standard error of the mean (SEM), as indicated. Data were analyzed by Student's t-test, one-way ANOVA followed by Tukey post-hoc multiple comparisons, or Wilcoxon rank-sum non-parametric test when appropriate. A P-value of <0.05 was taken to indicate a statistically significant difference.

6.7.13 In Vivo Imaging of Amyloid Plaques

Cranial windows were implanted above the somatosensory cortex of 10-month old APP hAPP(V717I)/PS1 mice, as previously described (Trachtenberg et al 2002, Holtmaat et al 2009), 2 weeks before the initial imaging session. Twenty-four hours prior to each imaging session animals were injected with 10 mg/kg Methoxy-X04 I.P. to visualize individual amyloid plaques (Klunk et al 2002) and immediately prior to imaging injected I.V. with AngioSense680 (VisEn Medical) to visualize blood vessels. For each imaging session animals were anesthetized with an isoflurane-oxygen mixture and mounted to the microscope using a head post. Images were collected via a two-photon laser scanning microscope (Ultima in vivo; Prairie Technologies) using a Ti:sapphire laser (MaiTai DeepSee; Spectra Physics) tuned to 820 nm delivering ~30 mW to the back-focal plane of a 40× NA 0.8 objective lens (Olympus). The pattern of the vasculature was used to reproducibly position the mouse relative to the objective from day-to-day enabling individual amyloid plaques to be imaged over many weeks. The volumes of individual plaques were estimated by summing the number of pixels above background within a region of interest drawn around a given plaque. Background is defined as the mean pixel intensity plus two standard deviations within a region of interest drawn adjacent to an amyloid plaque. Following the fourth and eighth imaging session, animals were dosed I.P. with 60 mg/kg MABT.

REFERENCES

Bandyopadhyay S, Hartley D M, Cahill C M, Lahiri D K, Chattopadhyay N, Rogers J T (2006) Interleukin-1 alpha stimulates non-amyloidogenic pathway by alpha-secretase (ADAM-10 and ADAM-17) cleavage of APP in human astrocytic cells involving p38 MAP kinase. J Neurosci Res 84:106-118.

Bateman D A, McLaurin J, Chakrabartty A (2007) Requirement of aggregation propensity of Alzheimer amyloid peptides for neuronal cell surface binding. BMC Neurosci 8:29.

Bitan G, Kirkitadze M D, Lomakin A, Vollers S S, Benedek G B, Teplow D B (2003) Amyloid beta-protein (Abeta) assembly: Abeta 40 and Abeta 42 oligomerize through distinct pathways. Proc Natl Acad Sci USA 100:330-335.

Casas C, Sergeant N, Itier J M, Blanchard V, Wirths O, van der K N, Vingtdeux V, van de S E, Ret G, Canton T, Drobecq H, Clark A, Bonici B, Delacourte A, Benavides J, Schmitz C, Tremp G, Bayer T A, Benoit P, Pradier L (2004) Massive CA1/2 neuronal loss with intraneuronal and N-terminal truncated Abeta42 accumulation in a novel Alzheimer transgenic model. Am J Pathol 165:1289-1300.

Clark M R (1997) IgG effector mechanisms. Chem Immunol 65:88-110.

Cleary J P, Walsh D M, Hofmeister J J, Shankar G M, Kuskowski M A, Selkoe D J, Ashe K H (2005) Natural oligomers of the amyloid-beta protein specifically disrupt cognitive function. Nat Neurosci 8:79-84.

Dewachter I, Reverse D, Caluwaerts N, Ris L, Kuiperi C, Van den H C, Spittaels K, Umans L, Serneels L, Thiry E, Moechars D, Mercken M, Godaux E, Van L F (2002) Neuronal deficiency of presenilin 1 inhibits amyloid plaque formation and corrects hippocampal long-term potentiation but not a cognitive defect of amyloid precursor protein [V717I] transgenic mice. J Neurosci 22:3445-3453.

Doyle S E, O'Connell R M, Miranda G A, Vaidya S A, Chow E K, Liu P T, Suzuki S, Suzuki N, Modlin R L, Yeh W C, Lane T F, Cheng G (2004) Toll-like receptors induce a phagocytic gene program through p38. J Exp Med 199:81-90.

Esler W P, Stimson E R, Ghilardi J R, Lu Y A, Felix A M, Vinters H V, Mantyh P W, Lee J P, Maggio J E (1996) Point substitution in the central hydrophobic cluster of a human beta-amyloid congener disrupts peptide folding and abolishes plaque competence. Biochemistry 35:13914-13921.

Gallagher T F, et al. (1997) Regulation of stress-induced cytokine production by pyridinylimidazoles; inhibition of CSBP kinase. Bioorg Med Chem 5:49-64.

Gessner J E, Heiken H, Tamm A, Schmidt R E (1998) The IgG Fc receptor family. Ann Hematol 76:231-248.

Gouras G K, Tsai J, Naslund J, Vincent B, Edgar M, Checler F, Greenfield J P, Haroutunian V, Buxbaum J D, Xu H, Greengard P, Relkin N R (2000) Intraneuronal Abeta42 accumulation in human brain. Am J Pathol 156:15-20.

Haass C, Selkoe D J (2007) Soluble protein oligomers in neurodegeneration: lessons from the Alzheimer's amyloid beta-peptide. pp 101-112.

Hickman S E, Allison E K, El K J (2008) Microglial dysfunction and defective beta-amyloid clearance pathways in aging Alzheimer's disease mice. J Neurosci 28:8354-8360.

Holmes C, Boche D, Wilkinson D, Yadegarfar G, Hopkins V, Bayer A, Jones R W, Bullock R, Love S, Neal J W, Zotova E, Nicoll J A (2008) Long-term effects of Abeta42 immunisation in Alzheimer's disease: follow-up of a randomised, placebo-controlled phase I trial. Lancet 372:216-223.

Kayed R, Head E, Thompson J L, McIntire T M, Milton S C, Cotman C W, Glabe C G (2003) Common structure of soluble amyloid oligomers implies common mechanism of pathogenesis. Science 300:486-489.

Koenigsknecht-Talboo J, Meyer-Luehmann M, Parsadanian M, Garcia-Alloza M, Finn M B, Hyman B T, Bacskai B J, Holtzman D M (2008) Rapid Microglial Response Around Amyloid Pathology after Systemic Anti-A{beta} Antibody Administration in PDAPP Mice. J Neurosci 28:14156-14164.

Lambert M P, Barlow A K, Chromy B A, Edwards C, Freed R, Liosatos M, Morgan T E, Rozovsky I, Trommer B, Viola K L, Wals P, Zhang C, Finch C E, Krafft G A, Klein W L (1998) Diffusible, nonfibrillar ligands derived from Abeta1-42 are potent central nervous system neurotoxins. Proc Natl Acad Sci USA 95:6448-6453.

Lee E B, Leng L Z, Lee V M, Trojanowski J Q (2005) Meningoencephalitis associated with passive immunization of a transgenic murine model of Alzheimer's amyloidosis. FEBS Lett 579:2564-2568.

Lee E B, Leng L Z, Zhang B, Kwong L, Trojanowski J Q, Abel T, Lee V M (2006) Targeting amyloid-beta peptide (Abeta) oligomers by passive immunization with a conformation-selective monoclonal antibody improves learning and memory in Abeta precursor protein (APP) transgenic mice. J Biol Chem 281:4292-4299.

Lee J C, Laydon J T, McDonnell P C, Gallagher T F, Kumar S, Green D, McNulty D, Blumenthal M J, Heys J R, Landvatter S W (1994) A protein kinase involved in the regulation of inflammatory cytokine biosynthesis. Nature 372: 739-746.

Lee Y B, Schrader J W, Kim S U (2000) p38 map kinase regulates TNF-alpha production in human astrocytes and microglia by multiple mechanisms. Cytokine 12:874-880.

Legleiter J, Czilli D L, Gitter B, DeMattos R B, Holtzman D M, Kowalewski T (2004) Effect of different anti-Abeta antibodies on Abeta fibrillogenesis as assessed by atomic force microscopy. J Mol Biol 335:997-1006.

Levine H, III (1993) Thioflavine T interaction with synthetic Alzheimer's disease beta-amyloid peptides: detection of amyloid aggregation in solution. Protein Sci 2:404-410.

Li R, Yang L, Lindholm K, Konishi Y, Yue X, Hampel H, Zhang D, Shen Y (2004) Tumor necrosis factor death receptor signaling cascade is required for amyloid-beta protein-induced neuron death. J Neurosci 24:1760-1771.

Ling Y, Morgan K, Kalsheker N (2003) Amyloid precursor protein (APP) and the biology of proteolytic processing: relevance to Alzheimer's disease. Int J Biochem Cell Biol 35:1505-1535.

Liu Q, Huang Y, Xue F, Simard A, DeChon J, Li G, Zhang J, Lucero L, Wang M, Sierks M, Hu G, Chang Y, Lukas R J, Wu J (2009) A novel nicotinic acetylcholine receptor subtype in basal forebrain cholinergic neurons with high sensitivity to amyloid peptides. J Neurosci 29:918-929.

Meberg P J, Miller M W (2003) Culturing hippocampal and cortical neurons. Methods Cell Biol 71:111-127.

Muhs A, Hickman D T, Pihlgren M, Chuard N, Giriens V, Meerschman C, Van dA, I, Van L F, Sugawara M, Weingertner M C, Bechinger B, Greferath R, Kolonko N, Nagel-Steger L, Riesner D, Brady R O, Pfeifer A, Nicolau C (2007) Liposomal vaccines with conformation-specific amyloid peptide antigens define immune response and efficacy in APP transgenic mice. Proc Natl Acad Sci USA 104:9810-9815.

Nimmerjahn F, Ravetch J V (2006) Fcgamma receptors: old friends and new family members. Immunity 24:19-28.

Oddo S, Caccamo A, Shepherd J D, Murphy M P, Golde T E, Kayed R, Metherate R, Mattson M P, Akbari Y, Laferla F M (2003) Triple-transgenic model of Alzheimer's disease with plaques and tangles: intracellular Abeta and synaptic dysfunction. Neuron 39:409-421.

Orgogozo J M, Gilman S, Dartigues J F, Laurent B, Puel M, Kirby L C, Jouanny P, Dubois B, Eisner L, Flitman S, Michel B F, Boada M, Frank A, Hock C (2003) Subacute meningoencephalitis in a subset of patients with AD after Abeta42 immunization. Neurology 61:46-54.

Perry R T, Collins J S, Wiener H, Acton R, Go R C (2001) The role of TNF and its receptors in Alzheimer's disease. Neurobiol Aging 22:873-883.

Pike C J, Burdick D, Walencewicz A J, Glabe C G, Cotman C W (1993) Neurodegeneration induced by beta-amyloid peptides in vitro: the role of peptide assembly state. J Neurosci 13:1676-1687.

Poduslo J F, Gilles E J, Ramakrishnan M, Howell K G, Wengenack T M, Curran G L, Kandimalla K K (2010) HH domain of Alzheimer's disease Abeta provides structural basis for neuronal binding in PC12 and mouse cortical/hippocampal neurons. PLoS One 5:e8813.

Poling A, Morgan-Paisley K, Panos J J, Kim E M, O'Hare E, Cleary J P, Lesne S, Ashe K H, Porritt M, Baker L E (2008) Oligomers of the amyloid-beta protein disrupt working memory: confirmation with two behavioral procedures. Behav Brain Res 193:230-234.

Ransohoff R M, Perry V H (2009) Microglial physiology: unique stimuli, specialized responses. Annu Rev Immunol 27:119-145.

Salloway S, Sperling R, Gilman S, Fox N C, Blennow K, Raskind M, Sabbagh M, Honig L S, Doody R, van Dyck C H, Mulnard R, Barakos J, Gregg K M, Liu E, Lieberburg I, Schenk D, Black R, Grundman M (2009) A phase 2 multiple ascending dose trial of bapineuzumab in mild to moderate Alzheimer disease. Neurology 73:2061-2070.

Selkoe D J (2002) Alzheimer's disease is a synaptic failure. Science 298(5594):789-791.

Shankar G M, Bloodgood B L, Townsend M, Walsh D M, Selkoe D J, Sabatini B L (2007) Natural oligomers of the Alzheimer amyloid-beta protein induce reversible synapse loss by modulating an NMDA-type glutamate receptor-dependent signaling pathway. J Neurosci 27:2866-2875.

Shields R L, Namenuk A K, Hong K, Meng Y G, Rae J, Briggs J, Xie D, Lai J, Stadlen A, Li B, Fox J A, Presta L G (2001) High resolution mapping of the binding site on human IgG1 for Fc gamma RI, Fc gamma RII, Fc gamma RIII and FcRn and design of IgG1 variants with improved binding to the Fc gamma R. J Biol Chem 276:6591-6604.

Simon P L, Laydon J T, Lee J C (1985) A modified assay for interleukin-1 (IL-1). J Immunol Methods 84:85-94.

Solomon B, Koppel R, Frankel D, Hanan-Aharon E (1997) Disaggregation of Alzheimer beta-amyloid by site-directed mAb. Proc Natl Acad Sci USA 94:4109-4112.

Spires-Jones T L, Mielke M L, Rozkalne A, Meyer-Luehmann M, de C A, Bacskai B J, Schenk D, Hyman B T (2009) Passive immunotherapy rapidly increases structural plasticity in a mouse model of Alzheimer disease. Neurobiol Dis 33:213-220.

Strittmatter W J, Saunders A M, Schmechel D, Pericak-Vance M, Enghild J, Salvesen G S, Roses A D (1993) Apolipoprotein E: high-avidity binding to beta-amyloid and increased frequency of type 4 allele in late-onset familial Alzheimer disease. Proc Natl Acad Sci USA 90:1977-1981.

The International Federation of Alzheimer's Disease and Related Disorders Societies I (2009) World Alzeheimer Report—2009 Executive Summary. (Prince M, Jackson J, eds), pp 1-21. Illinois, USA: Alzheimer's Disease International: The International Federation of Alzheimer's Disease and Related Disorders Societies, Inc.

Townsend M, Shankar G M, Mehta T, Walsh D M, Selkoe D J (2006) Effects of secreted oligomers of amyloid beta-protein on hippocampal synaptic plasticity: a potent role for trimers. J Physiol 572:477-492.

Vellas B, Black R, Thal L J, Fox N C, Daniels M, McLennan G, Tompkins C, Leibman C, Pomfret M, Grundman M (2009) Long-term follow-up of patients immunized with AN1792: reduced functional decline in antibody responders. Curr Alzheimer Res 6:144-151.

Walsh D M, Klyubin I, Fadeeva J V, Cullen W K, Anwyl R, Wolfe M S, Rowan M J, Selkoe D J (2002) Naturally secreted oligomers of amyloid beta protein potently inhibit hippocampal long-term potentiation in vivo. Nature 416: 535-539.

Walsh D M, Klyubin I, Shankar G M, Townsend M, Fadeeva J V, Betts V, Podlisny M B, Cleary J P, Ashe K H, Rowan M J, Selkoe D J (2005) The role of cell-derived oligomers of Abeta in Alzheimer's disease and avenues for therapeutic intervention. Biochem Soc Trans 33:1087-1090.

Wang Q, Walsh D M, Rowan M J, Selkoe D J, Anwyl R (2004) Block of long-term potentiation by naturally secreted and synthetic amyloid beta-peptide in hippocampal slices is mediated via activation of the kinases c-Jun N-terminal kinase, cyclin-dependent kinase 5, and p38 mitogen-activated protein kinase as well as metabotropic glutamate receptor type 5. J Neurosci 24:3370-3378.

Wirths O, Multhaup G, Czech C, Blanchard V, Moussaoui S, Tremp G, Pradier L, Beyreuther K, Bayer T A (2001) Intraneuronal Abeta accumulation precedes plaque formation in beta-amyloid precursor protein and presenilin-1 double-transgenic mice. Neurosci Lett 306:116-120.

Barghorn S, Nimmrich V, Striebinger A, Krantz C, Keller P, Janson B, Bahr M, Schmidt M, Bitner R S, Harlan J, Barlow E, Ebert U, Hillen H (2005) Globular amyloid beta-peptide oligomer—a homogenous and stable neuropathological protein in Alzheimer's disease. J Neurochem 95:834-847.

Blond and Goldberg, 1987, PNAS Mar. 1, 1987 Vol. 84|no. 5|1147-1151

Cox J P L, Tomlinson I M and Winter G. Eur. J. Immunol. 1994; 24: 827-836. A directory of human germ-line V kappa segments reveals a strong bias in their usage.

Hieter P A, Max E E, Seidman J G, Maizel J V Jr, Leder P. Cloned human and mouse kappa immunoglobulin constant and J region genes conserve homology in functional segments. Cell. 1980 November; 22(1 Pt 1):197-207.

Kabat E A, Wu T T, Perry H M, Gottesman K S, Foeller C. Sequences of proteins of Immunological Interest, US Department of Health and Human Services, 1991.

Klein W L (2002) Abeta toxicity in Alzheimer's disease: globular soluble polymeric amyloid beta (ADDLs) as new vaccine and drug targets. Neurochem Int 41(5):345-352.

Langdon S D, Inaioki M, Kelsoe G. and Tedder T F. Immunogenetics 2000; 51: 241-245. Germline sequences of V(H)7183 gene family members in C57BL/6 mice demonstrate natural selection of particular sequences during recent evolution Mulligan R C and Berg P. Science 1980; 209: 1422-1427. Expression of a bacterial gene in mammalian cells.

Riechmann L, Clark M, Waldmann H, Winter G, Nature 1988; 332: 323-327. Reshaping human antibodies for therapy.

Schable K F, Thiebe R, Bensch A, Brensing-Kueppers J, Heim V, Kirschbaum T, Lamm R, Ohnrich M, Pourrajabi S, Roschenthaler F, Schwendinger J, Wichelhaus D, Zocher I and Zachau H G. Eur. J. Immunol. 1999; 29: 2082-2086. Characteristics of the immunoglobulin V kappa genes, pseudogenes, relics and orphons in the mouse genome.

Tomlinson I M, Walter G, Marks J D, Llewelyn M B and Winter G. J. Mol. Biol. 1992; 227: 776-798. The repertoire of human germline VH sequences reveals about 50 groups of VH segments with different hypervariable loops

---

What is claimed is:

1. A method for identifying an anti-beta amyloid antibody having neuroprotective activity, wherein the method comprises:
   a. incubating microglia cells with beta amyloid oligomer and the anti-beta amyloid antibody; and
   b. measuring the uptake of beta amyloid oligomer by microglia cells; and
   c. measuring p38 MAP kinase activation in the microglia cells, and
   d. identifying the uptake of beta amyloid oligomer into the microglia cells and an intermediate level of p38 MAP kinase activation in the microglia cells incubated with the anti-beta amyloid antibody as an indication of an anti-beta amyloid antibody having neuroprotective activity,
wherein the intermediate level of p38 MAP kinase activation is a level higher than a level of activation of p38 MAP kinase in the presence of beta amyloid oligomer without the anti-beta amyloid antibody, but lower than a level of activation of p38 MAP kinase in the presence of beta amyloid oligomer and an IgG1 antibody that specifically binds beta amyloid oligomer, and wherein the IgG1 antibody comprises a human IgG1 constant region.

2. A method for testing the safety of an anti-beta amyloid antibody, wherein the method comprises:
   a. incubating microglia cells with beta amyloid oligomer in the presence and the absence of a anti-beta amyloid antibody; and
   b. measuring p38 MAP kinase activation in microglia cells in the presence and the absence of the anti-beta amyloid antibody; and
   c. identifying the anti-beta amyloid antibody as safe if the anti-beta amyloid antibody is capable of inducing an intermediate level of p38 MAP kinase activation in the microglia cells, wherein the intermediate level of p38 MAP kinase activation is a level higher than a level of activation of p38 MAP kinase in the presence of beta amyloid oligomer without the anti-beta amyloid antibody, but lower than a level of activation of p38 MAP kinase in the presence of beta amyloid oligomer and an IgG1 antibody that specifically binds beta amyloid oligomer, and wherein the IgG1 antibody comprises a human IgG1 constant region.

3. The method of claim 2, wherein the IgG1 antibody comprises a light chain variable region comprising the amino acid sequence of SEQ ID NO: 7 and a heavy chain variable region comprising the amino acid sequence of SEQ ID NO: 10.

4. The method of claim 1 or 2, wherein the intermediate activation of p38 MAP kinase in microglia cells is between 5%-15%; 10%-20%; 15%-25%; 20%-30%; 35%-45%; 40%-50%; or 45%-55% above p38 MAP kinase activation in microglia cells in the presence of beta amyloid oligomer without the anti-beta amyloid antibody.

5. The method of claim 1 or 2, wherein the anti-beta amyloid antibody comprises:
   a. a light chain variable region complementarity determining region (CDR)1 having the amino acid sequence of the light chain variable region CDR1 of an anti-beta amyloid antibody listed in Table 2;
   b. a light chain variable region CDR2 having the amino acid sequence of the light chain variable region CDR2 of an anti-beta amyloid antibody listed in Table 2; and
   c. a light chain variable region CDR3 having the amino acid sequence of the light chain variable region CDR3 of an anti-beta amyloid antibody listed in Table 2.

6. The method of claim 5, wherein the anti-beta amyloid antibody further comprises:
   a. a heavy chain variable region CDR1 having the amino acid sequence of the heavy chain variable region CDR1 of an anti-beta amyloid antibody listed in Table 2;
   b. a heavy chain variable region CDR2 having the amino acid sequence of the heavy chain variable region CDR2 of an anti-beta amyloid antibody listed in Table 2; and
   c. a heavy chain variable region CDR3 having the amino acid sequence of the heavy chain variable region CDR3 of an anti-beta amyloid antibody listed in Table 2.

7. The method of claim 6, wherein the CDR1, CDR2, and CDR3 of the light chain variable region and the CDR1, CDR2, and CDR3 of the heavy chain variable region are all derived from the same anti-beta amyloid antibody listed in Table 2.

8. The method of claim 5, wherein the CDR1, CDR2, and CDR3 of the light chain variable region are all derived from the same anti-beta amyloid antibody listed in Table 2.

9. The method of claim 1 or 2, wherein the anti-beta amyloid antibody comprises:
   a. a heavy chain variable region CDR1 having the amino acid sequence of the heavy chain variable region CDR1 of an anti-beta amyloid antibody listed in Table 2;
   b. a heavy chain variable region CDR2 having the amino acid sequence of the heavy chain variable region CDR2 of an anti-beta amyloid antibody listed in Table 2; and
   c. a heavy chain variable region CDR3 having the amino acid sequence of the heavy chain variable region CDR3 of an anti-beta amyloid antibody listed in Table 2.

10. The method of claim 9, wherein the CDR1, CDR2, and CDR3 of the heavy chain variable region are all derived from the same anti-beta amyloid antibody listed in Table 2.

11. The method of claim 1 or 2, wherein the intermediate level of p38 MAP kinase activation is determined by the step of: comparing the levels of p38 MAP kinase activation in microglia cells by beta amyloid oligomer in the presence and absence of the anti-beta amyloid antibody, wherein if the level of p38 MAP kinase activation by beta amyloid oligomer in the presence of the anti-beta amyloid antibody is greater than the level of p38 MAP kinase activation by beta-amyloid oligomer in the absence of the anti-beta amyloid antibody, but less than the level of p38 MAP kinase activation by beta-amyloid oligomer and an IgG1 anti-beta amyloid antibody comprising a human IgG1 constant region, then the level of p38 MAP kinase activation is determined to be an intermediate level.

12. The method of claim 1 or 2, wherein the anti-beta amyloid antibody is safe and functional for the treatment of an amyloidosis associated with beta-amyloid deposits.

13. The method of claim 12, wherein the amyloidosis is Alzheimer's Disease.

14. The method of claim 1 or 2, wherein the anti-beta amyloid antibody has the effector region of an IgG4 antibody.

15. The method of claim 1 or 2, wherein the anti-beta amyloid antibody is a non-IgG1 antibody which does not comprise a human IgG1 constant region.

16. The method of claim 1 or 2, wherein the anti-beta amyloid antibody comprises a heavy chain CDR1 comprising the amino acid sequence of SEQ ID NO: 1, a heavy chain CDR2 comprising the amino acid sequence of SEQ ID NO: 2, and a heavy chain CDR3 comprising the amino acid sequence of SEQ ID NO: 3, and a light chain CDR1 comprising the amino acid sequence of SEQ ID NO: 4, a light chain CDR2 comprising the amino acid sequence of SEQ ID NO: 5, SEQ ID NO: 23 or SEQ ID NO: 24, and a light chain CDR3 comprising the amino acid sequence of SEQ ID NO: 6.

17. The method of claim 1 or 2, wherein the anti-beta amyloid antibody comprises a heavy chain variable region comprising the amino acid sequence of SEQ ID NO: 7.

18. The method of claim 1 or 2, wherein the anti-beta amyloid antibody comprises a light chain variable region comprising the amino acid sequence of SEQ ID NO: 10.

19. The method of claim 1 or 2, wherein the anti-beta amyloid antibody comprises a heavy chain variable region comprising the amino acid sequence of SEQ ID NO: 7 and a light chain variable region comprising the amino acid sequence of SEQ ID NO: 10.

20. A method for testing the safety and neuroprotective activity of an anti-beta amyloid antibody, wherein the method comprises:
   a. incubating microglia cells with beta amyloid oligomer in the presence and absence of the anti-beta amyloid antibody;
   b. measuring uptake of beta amyloid oligomer by the microglia cells in the presence and absence of the anti-beta amyloid antibody;
   c. measuring p38 MAP kinase activation in microglia cells in the presence and absence of the anti-beta amyloid antibody, wherein if (i) the presence of the anti-beta amyloid antibody increases uptake of beta amyloid oligomer by microglia cells as compared to uptake of beta amyloid oligomer by microglia cells in the absence of the anti-beta amyloid antibody, and (ii) the level of p38 MAP kinase activation in microglia cells by beta-amyloid oligomer in the presence of the anti-beta amyloid antibody is greater than the level of p38 MAP kinase activation by beta-amyloid oligomer in the absence of the anti-beta amyloid antibody, but less than the level of p38 MAP kinase activation by beta amyloid oligomer and an IgG1 anti-beta amyloid antibody comprising a human IgG1 constant region, then the anti-beta amyloid antibody is identified as a safe and neuroprotective anti-beta amyloid antibody.

21. The method of claim 20, wherein the anti-beta amyloid antibody is safe and functional for the treatment of an amyloidosis associated with beta-amyloid deposits.

22. The method of claim 21, wherein the antibody is a non-IgG1 antibody which does not comprise a human IgG1 constant region.

23. The method of claim 20, wherein the amyloidosis is Alzheimer's Disease.

24. The method of claim 20, wherein the anti-beta amyloid antibody has the effector region of an IgG4 antibody.

25. The method of claim 20, wherein the anti-beta amyloid antibody is a human IgG4 isotype and the IgG1 antibody is the same anti-beta amyloid antibody having a human IgG1 isotype.

26. The method of claim 1, 2, or 20, wherein the beta amyloid oligomer in step a. is beta amyloid 1-42 oligomers.

* * * * *